(12) United States Patent
Watt et al.

(10) Patent No.: US 9,132,102 B2
(45) Date of Patent: Sep. 15, 2015

(54) STILBENE ANALOGS AND METHODS OF TREATING CANCER

(71) Applicant: UNIVERSITY OF KENTUCKY RESEARCH FOUNDATION, Lexington, KY (US)

(72) Inventors: David Watt, Lexington, KY (US); Chunming Liu, Lexington, KY (US); Vitaliy M. Sviripa, Lexington, KY (US); Wen Zhang, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 14/192,616

(22) Filed: Feb. 27, 2014

(65) Prior Publication Data
US 2014/0249161 A1 Sep. 4, 2014

Related U.S. Application Data

(62) Division of application No. 13/360,109, filed on Jan. 27, 2012, now Pat. No. 8,664,273.

(60) Provisional application No. 61/437,341, filed on Jan. 28, 2011, provisional application No. 61/439,118, filed on Feb. 3, 2011.

(51) Int. Cl.
| | |
|---|---|
| *A61K 31/03* | (2006.01) |
| *A61K 31/44* | (2006.01) |
| *C07C 211/48* | (2006.01) |
| *C07C 211/52* | (2006.01) |
| *C07C 291/04* | (2006.01) |
| *C07D 233/64* | (2006.01) |
| *C07D 295/073* | (2006.01) |
| *C07D 495/04* | (2006.01) |
| *G01N 33/574* | (2006.01) |
| *G01N 33/58* | (2006.01) |
| *C07C 39/21* | (2006.01) |
| *C07C 43/23* | (2006.01) |

(52) U.S. Cl.
CPC ............ *A61K 31/03* (2013.01); *A61K 31/44* (2013.01); *C07C 39/21* (2013.01); *C07C 43/23* (2013.01); *C07C 211/48* (2013.01); *C07C 211/52* (2013.01); *C07C 291/04* (2013.01); *C07D 233/64* (2013.01); *C07D 295/073* (2013.01); *C07D 495/04* (2013.01); *G01N 33/57484* (2013.01); *G01N 33/582* (2013.01); *G01N 2800/52* (2013.01)

(58) Field of Classification Search
CPC .... C07C 211/52; C07C 291/04; C07C 39/21; C07C 43/23; C07D 233/64; C07D 295/073; C07D 495/04; A61K 31/03; A61K 31/44
See application file for complete search history.

(56) References Cited

U.S. PATENT DOCUMENTS

| | | | |
|---|---|---|---|
| 4,683,087 A | 7/1987 | Witiak et al. | |
| 5,430,062 A | 7/1995 | Cushman et al. | |
| 5,674,906 A | 10/1997 | Hatanaka et al. | |
| 6,552,085 B2 | 4/2003 | Inman et al. | |
| 6,562,834 B2 | 5/2003 | Bissery | |
| 6,790,869 B2 | 9/2004 | Ghai et al. | |
| 6,919,324 B2 | 7/2005 | Chaplin et al. | |
| 6,992,106 B2 | 1/2006 | Morinaga et al. | |
| 7,655,696 B2 | 2/2010 | Morinaga et al. | |
| 2003/0203908 A1 | 10/2003 | Lowe | |
| 2004/0147788 A1 | 7/2004 | Savouret et al. | |
| 2005/0096384 A1 | 5/2005 | Forman et al. | |
| 2006/0094716 A1* | 5/2006 | Aissaoui et al. | ........... 514/232.5 |
| 2007/0249647 A1 | 10/2007 | Vander Jagt et al. | |
| 2008/0096973 A1 | 4/2008 | Liou et al. | |
| 2008/0108840 A1 | 5/2008 | Kung et al. | |
| 2008/0261982 A1 | 10/2008 | Lee et al. | |
| 2009/0136431 A1 | 5/2009 | Srinivas et al. | |
| 2009/0221666 A1 | 9/2009 | Pettit et al. | |
| 2010/0056463 A1 | 3/2010 | Raederstorff et al. | |
| 2010/0119499 A1 | 5/2010 | Kneller et al. | |

FOREIGN PATENT DOCUMENTS

| | | |
|---|---|---|
| CN | 1143629 A | 2/1997 |
| CN | 100482638 C | 4/2009 |
| JP | 02-085828 A | 3/1990 |
| JP | 05-249517 A | 9/1993 |
| WO | 03/099763 A1 | 12/2003 |
| WO | 2008-070872 A1 | 6/2008 |

OTHER PUBLICATIONS

Cancer definition in MedicineNet.com 2004.*
"Adult Brain Tumors Treatment", National Cancer Institute, pp. 1-21 (Jan. 24, 2013).*
"Types of Brain Cancer" at http://www.cancercenter.com/brain-cancer/types-of-brain-cancer.cfm (Mar. 12, 2013).*
"Colorectal Cancer" at cancer.net (published Sep. 2012), pp. 1-2.*
"Types of Breast Cancer", published in breastcancer.org (Sep. 30, 2012); p. 1.*
Stomach cancer—Mayoclinic.com—2012.*
Schafer et al. Drug discovery Today 2008, 13 (21/22), 913-916.*
Luo et al. (Cell 136, Mar. 6, 2009; 823-837).*
Wang et al. (BMC Cancer 2014, 14:196).*
International Search Report and the Written Opinion of the International Searching Authority issued in International Patent Application No. PCT/US2012/022938 dated Aug. 3, 2012.

(Continued)

*Primary Examiner* — Valerie Rodriguez-Garcia
(74) *Attorney, Agent, or Firm* — McDermott Will & Emery LLP

(57) ABSTRACT

Stilbene analogs and pharmaceutical compositions that are useful for the treatment of various cancers, including without limitation, colorectal cancer (CRC) and breast cancer are disclosed. The halogenated stilbene analogs include nitrogen heteroaryl groups and/or amino groups on the stilbene ring.

7 Claims, 18 Drawing Sheets

(56) References Cited

OTHER PUBLICATIONS

Mohammad, S. "A Quantum Mechanical Approach to the Theory of Cancer from Polynuclear Compounds". Molecular Pharmacology an International Journal. Jan. 1985. vol. 27. pp. 148-155.

Reid, E. "Carcinogenic Action of 2-Chloro-4-Dimethylaminostilbene, In Relation to (A) Possible Effects of Growth Hormone, and (B) Composition of Liver Cytoplasm". British Journal of Cancer. Mar. 1956. pp. 123-128.

Gu, B. et al. "Epithelial Stem Cells: An Epigenetic and Wnt-Centic Perspective." Journal of Cellular Biochemistry. 110:1279-1287. 2010.

Zhang, W. et al. "Fluorinated N,N-Dialkylaminostilbenes for Wnt Pathway Inhibition and Colon Cancer Repression." Journal of Medicinal Chemistry. vol. 54. pp. 1288-1297. 2011.

Hotchkiss, P. et al. "Modification of the Surface Properties of Indium Tin Oxide with Benzylphosphonic Acids: A Joint Experimental and Theoretical Study." Advanced Materials. vol. 21. pp. 4496-4501. 2009.

Ito, K. et al. "Correlation Between the Expression of Methionine Adenosyltransferase and the Stages of Human Colorectal Carcinoma." Surgery Today. vol. 30. pp. 706-710. Mar. 24, 2000.

Liu, Q. et al. "The X Protein of Hepatitis B Virus Inhibits Apoptosis in Hepatoma Cells through Enhancing the Methionine Adenosyltransferase 2A Gene Expression and Reducing S-Adenosylmethionine Production." Journal of Biological Chemistry. vol. 286. No. 19. pp. 17168-17180. May 13, 2011.

Cantoni, G.L. et al. "S-Adenosylmethionine; a new intermediate formed enzymatically from L-methionine and adenosinetriphosphate." Received for Publication: Mar. 23, 1953. pp. 403-416.

Cai, J. et al. "Changes in S-Adenosylmethionine Synthetase in Human Liver Cancer: Molecular Characterization and Significance." Hepatology. vol. 24. No. 5. pp. 1090-1097. 1996.

International Preliminary Report and Written Opinion issued in corresponding PCT Application No. PCT/US2012/022938, mailed Aug. 5, 2013.

Huang et al.: J. Phys Chem. C 2007, 111, 10672-10681).

International Search Report and the Written Opinion of the International Searching Authority issued in International Patent Application No. PCT/US2012/022938 dated Jan. 27, 2012.

Rimando, Agnes, et al., "Biological/Chemopreventative Activity of Stilbenes and their Effect on Colon Cancer", Planta Med, 2008, pp. 1635-1643, Georg Thieme Verlag KG.

Supplementary European Search Report EP 12 73 9698 dated May 26, 2014.

Tanvi S. Jani et al., "Inhibition of methionine adenosyltransferase II induces FasL expression, Fas-DISC formation and caspase-8-dependent apoptotic death in T leukemic cells", Cell Research (2009) vol. 19, No. 3, pp. 358-369.

Chinese Office Action issued in Chinese Patent Application No. 201280013655.1 dated Sep. 22, 2014 w/English translation.

Notification of the Second Office Action, Chinese Patent Application No. 201280013655.1 dated May 11, 2015 with full English translation.

\* cited by examiner

A

B

A

B

A

B

C

D

STILBENE ANALOGS AND METHODS OF TREATING CANCER

CROSS-REFERENCE TO RELATED APPLICATION

This application is a Divisional of U.S. application Ser. No. 13/360,109, filed on Jan. 27, 2012, which claims the benefit of both U.S. Provisional Application No. 61/437,341 filed Jan. 28, 2011 and U.S. Provisional Application No. 61/439,118, filed Feb. 3, 2011, the entire disclosures of which are incorporated by reference herein.

SEQUENCE LISTING

The application contains a Sequence Listing which has been submitted in ASCII format via EFS-Web and is hereby incorporated by reference in its entirety. The Sequence Listing was previously submitted in parent application Ser. No. 13/360,109. Said ASCII copy, created on May 14, 2014, is named SequenceListing_050229_0626.txt, and it is 5,375 bytes in size.

STATEMENT REGARDING FEDERALLY SPONSORED RESEARCH

This invention was made with government support under 2P20 RR020171 awarded by The National Institutes of Health. The government has certain rights in the invention.

TECHNICAL FIELD

The present disclosure is directed to compounds having antineoplastic activity. In particular, the disclosure is directed to halogenated stilbene analogs and methods of identifying the specific molecular target of the stilbene analogs and inhibiting cancer cell growth in a patient by administering the stilbene analogs to the patient. Additionally, the present disclosure is directed to the direct target of stilbene analogs, methionine adenosyltransferase 2A (MAT2A), and methods of detecting the levels of MAT2A in a complex protein mixture.

BACKGROUND

Resveratrol (trans- or (E)-3,5,4'-trihydroxystilbene (1)) (FIG. 1) is a phytoalexin produced in plants and popularized as a beneficial ingredient of red wine. Resveratrol, its cis- or (Z)-isomer (2), and another stilbene derivative, pterostilbene (3), exhibit some anti-cancer activity. (FIG. 1) Recently, we found that resveratrol and pterostilbene, a stilbene found in blueberries, inhibit colon cancer cells at least partially through inhibiting Wnt/β-catenin signaling. Zhang, W. et al., *J Med Chem* 2011, 54, 1288-97.

Wnt/β-catenin signaling plays an important role in development and tumorigenesis, and the deregulation of Wnt signaling results in formation of tumors. Over 90% of colorectal cancers contain a mutation in APC or β-catenin, and these mutations stabilize β-catenin and activate Wnt signaling. Cells containing these mutations constitutively activate Wnt signaling and undergo strong proliferation that ultimately leads to cancer. Intercepting and blocking the Wnt/β-catenin pathway at various points in the signaling cascade is an attractive target for colon cancer chemoprevention and therapeutics.

Several Wnt inhibitors have been identified that target the upstream signaling of β-catenin and promote β-catenin degradation. Although these agents inhibit Wnt signaling in normal cells and some APC-mutated colon cancer cells, they may not be effective in colon cancer cells containing β-catenin mutations. Several other Wnt inhibitors have also been reported. However, side effects limit their potential use in humans. Natural products found in foods are potentially ideal chemopreventive and therapeutic agents for cancer if they possess sufficient potency and minimal toxicity.

Therefore, there is an ongoing need for compounds that are more potent than resveratrol and pterostilbene and that can be used to treat cancer and other ailments. There is also a particular need for compounds that do not exhibit deleterious side effects.

SUMMARY OF THE DISCLOSURE

Advantages of the present disclosure include halogenated stilbene analogs and compositions having antineoplastic activity and methods of inhibiting cancer cell growth and/or treating cancer in a patient by administering one or more of the halogenated stilbene analogs or compositions.

One aspect of the present disclosure is directed to halogenated stilbene analogs that are useful for killing hyperproliferating cells such as cancer cells for the treatment of human malignant and benign cancers, including without limitation, colorectal cancer (CRC), liver and breast cancer. In this aspect of the disclosure, there are provided certain halogenated stilbene analogs having anti-neoplastic activity against cancerous cells. The halogenated stilbene analogs of the present disclosure include compounds according to formula (I):

$$X-Ar_1-CR^a=CR^b-Ar_2 \quad (I)$$

wherein $R^a$ and $R^b$ are independently H, alkyl, halo, alkoxy, cyano; X represents at least one halogen, e.g., a fluorine, chlorine, bromine, or iodine substituent, on $Ar_1$; each of $Ar_1$ and $Ar_2$ are aryl, e.g., phenyl, naphthyl, and heteroaryl, e.g., pyridyl, pyrolidyl, piperidyl, pyrimidyl, indolyl, thienyl, which can be further substituted with halo, amino, alkylamino, dialkylamino, arylalkylamino, N-oxides of dialkylamino, trialkylammonium, mercapto, alkylthio, alkanoyl, nitro, nitrosyl, cyano, alkoxy, alkenyloxy, aryl, heteroaryl, sulfonyl, sulfonamide, $CONR_{11}R_{12}$, $NR_{11}CO(R_{13})$, $NR_{11}COO(R_{13})$, $NR_{11}CONR_{12}R_{13}$ where $R_{11}$, $R_{12}$, $R_{13}$, are independently, H, alkyl, aryl, heteroaryl or a fluorine; provided that $Ar_2$ contains at least one nitrogen atom in the aryl ring or at least one nitrogen substituent on the aryl ring; e.g., an $NR^cR^dZ$ substituent where $R^c$ is H, alkyl, alkoxy, aryl, heteroaryl, $R^d$ is an alkyl group, Z is a an unshared pair of electrons, H, alkyl, oxygen; or a pharmaceutically acceptable salt thereof.

In another embodiment of the present disclosure, the halogenated stilbene analogs include compounds of formula (II):

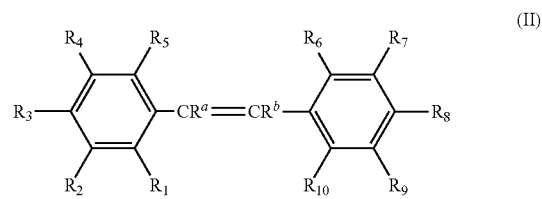

(II)

or a pharmaceutically acceptable salt thereof, wherein each of $R^a$ and $R^b$ are as defined above;

$R_1$ to $R_{10}$ are independently H, halo, amino, alkylamino, dialkylamino, N-oxides of dialkylamino, arylalkylamino, dialkyloxyamino, trialkylammonium, mercapto, alkylthio, alkanoyl, nitro, nitrosyl, cyano, alkoxy, alkenyloxy, aryl, heteroaryl, sulfonyl, sulfonamide, $CONR_{11}R_{12}$, $NR_{11}CO(R_{13})$, $NR_{11}COO(R_{13})$, $NR_{11}CONR_{12}R_{13}$ where $R_{11}$, $R_{12}$, $R_{13}$, are independently, H, alkyl, aryl, heteroaryl or a fluorine; provided at least one of $R_1$ to $R_5$ is a halogen, e.g. a fluorine and/or chlorine; and at least one of $R_6$ to $R_{10}$ is a nitrogen containing substituent, e.g., an $NR^cR^dZ$ substituent where $R^c$ is H, alkyl, alkoxy, aryl, heteroaryl, $R^d$ is an alkyl group, Z is a an unshared pair of electrons, H, alkyl, oxygen.

In another embodiment of the present disclosure, the halogenated stilbene analogs include compounds according to formula (III):

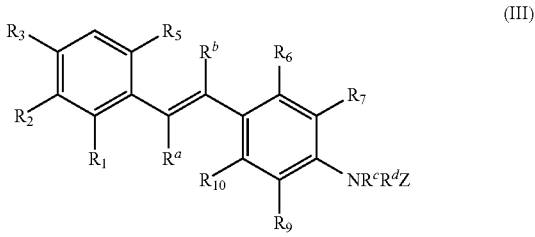

(III)

or a pharmaceutically acceptable salt thereof, where, $R_2$, $R_3$, $R_5$, $R_6$, $R_7$, $R_9$, $R_{10}$, $R^a$, $R^b$ and $NR^cR^dZ$ are the same as defined above.

The present disclosure also encompasses biotinylated derivates of the halogenated stilbene analogs and metabolites of the halogenated stilbene analogs.

The present disclosure further encompasses pharmaceutical compositions of the halogenated stilbene analogs, e.g., one or more compounds of formula (I), formula (II) and/or formula (III) and/or one or more pharmaceutically acceptable salts of compounds according to formulas (I), (II) and/or (III), in combination with a pharmaceutical carrier. In one aspect of the present disclosure, the pharmaceutical compositions comprise an effective amount of at least one halogenated stilbene analog.

The present disclosure is further directed to methods of treating cancer, e.g., inhibiting cancer cell growth and/or inhibiting tumor growth in a mammal, such as a human, or treating diseases associated with hyperproliferating cells. In one embodiment of this aspect of the disclosure, a therapeutically effective amount of one or more halogenated stilbene analogs, pharmaceutical salts and/or compositions thereof is administered to a patient in need of treatment of cancer sufficient to treat/inhibit cancer cell growth in the patient.

In another embodiment of this aspect of the disclosure, a therapeutically effective amount of one or more halogenated stilbene analogs, pharmaceutical salts and/or compositions thereof sufficient to inhibit the cancer cell growth in a patient is administered to a patient suffering from colorectal cancer. In another embodiment, a therapeutically effective amount of one or more halogenated stilbene analogs, pharmaceutical salts and/or compositions thereof sufficient to inhibit or treat breast cancer.

In yet another embodiment, a therapeutically effective amount of one or more halogenated stilbene analogs, pharmaceutical salts and/or compositions thereof sufficient to inhibit the cancer cell growth in a patient is administered to a patient suffering from age-related cancer. Non-limiting examples of age-related cancers include prostate, breast, lung and colorectal cancers, which tend to occur more in older individuals, e.g., 65 years or older.

In another aspect of the present disclosure, there is provided a method for disrupting Wnt signaling and/or other pathways using inhibitors of the enzyme, methionine S-adenosyltransferase, in a cell by treating the cell with an effective amount of a halogenated stilbene analog. These analogs can inhibit methionine adenosyltransferase 2A (MAT2A) and reduce cellular S-adenosyl-methionine (SAM), which is a major donor of DNA methylation and protein methylation that regulate gene expression and tumor growth. SAM is also a key factor in metabolic pathways. Thus, the halogenated stilbene analogs described in the present disclosure are also drug candidates for treatment of metabolic diseases, such as diabetes.

The present disclosure further encompasses a pharmaceutical composition including one or more compounds of formula (I), formula (II) and/or formula (III) and/or one or more pharmaceutically acceptable salt, solvate, hydrate, prodrug or metabolite thereof, for treatment of a disorder associated with an increased MAT2A biological activity or levels. In a related embodiment, the disorder associated with an increased MAT2A biological activity or levels is cancer. In another embodiment, the cancer is colon cancer, breast cancer, lung cancer, prostate cancer or liver cancer.

The present disclosure is also directed to a method of treating a disorder associated with an increased methionine adenosyltransferase 2A (MAT2A) biological activity or levels in a subject including administering to the subject an effective amount of one or more compounds of formula (I)-(III) and/or one or more pharmaceutically acceptable salt, solvate, hydrate, prodrug or metabolite thereof. In another embodiment, the present disclosure is directed to a method of treating a disorder associated with an increased MAT2A biological activity or levels in a subject including administering to the subject an effective amount of a composition including one or more compounds of formula (I)-(III) and/or one or more pharmaceutically acceptable salt, solvate, hydrate, prodrug or metabolite thereof. In a related embodiment, the disorder associated with an increased MAT2A biological activity or levels is cancer. In another related embodiment, the cancer is colon cancer, breast cancer, lung cancer, prostate cancer or liver cancer.

The present disclosure is also directed to a method of modulating MAT2A activity in a subject, the method including administering to the subject an effective amount of one or more compounds of formula (I), formula (II) and/or formula (III) and/or one or more pharmaceutically acceptable salt, solvate, hydrate, prodrug or metabolite thereof. In a related embodiment, the modulation of MAT2A activity includes decreasing MAT2A biological activity or level in a subject. In another related embodiment, the modulation of MAT2A activity includes decreasing SAM and/or S-adenosylhomocysteine (SAH) synthesis.

The present disclosure is also directed to a method of detecting the levels of MAT2A in a complex protein sample, said method includes contacting a detectably labeled compound of formula (I)-(III) to said complex protein mixture under conditions whereby said labeled compound binds to MAT2A present in the sample; isolating the bound MAT2A; removing any unbound proteins and detecting the level of the MAT2A bound to the detectably labeled compound in the sample. In a related embodiment, the isolation of the bound MAT2A is carried out by an affinity-based separation method. In another related embodiment, the compound of (I)-(III) is biotinylated. In another related embodiment, the detection is conducted by western blot, HPLC, FPLC, ion exchange, size exclusion, fluorescence spectroscopy, UV-Vis spectrometry or mass spectrometry.

The present disclosure is further directed to a method of diagnosing cancer in a subject, including: (1) obtaining a sample comprising protein from the subject, (2) contacting a detectably labeled compound of formula (I)-(III) with proteins in the sample to bind to MATA2 and detect the level of MAT2A in said sample; and (3) comparing the levels of MAT2A in the sample to that of a normal reference, whereupon if the level of MAT2A in the sample is statistically higher than that of the normal reference, a diagnosis of cancer is indicated. In a related embodiment, the detection in step (2) is carried out according to the method described in the preceeding paragraph. In another related embodiment, the sample obtained from a subject is a biopsy sample including cancer cells selected from breast, prostate, colorectal, lung, colon, bladder, head and neck, intestine, ovarian, or skin cancer cells.

The present disclosure further relates to a method of identifying a subject who is a candidate for receiving treatment with one or more compounds of formula (I), formula (II) or formula (III) or one or more pharmaceutically acceptable salt, solvate, hydrate, prodrug or metabolite thereof; said method includes (1) obtaining a protein sample from the subject, (2) contacting a detectably labeled compound of formula (I)-(III) with proteins in the sample to bind to MATA2 and detect the level of MAT2A in said sample; and (3) comparing the level of MAT2A in the sample to that in a normal reference, whereupon if the level of MAT2A in the sample is statistically higher than that of the normal reference, the candidacy of the subject for treatment with compounds of formula (I), formula (II) or formula (III) or one or more pharmaceutically acceptable salt, solvate, hydrate, prodrug or metabolite thereof is indicated. In a related embodiment, the detection in step (2) is carried out according to the method described in the above paragraph describing detecting the levels of MAT2A in complex protein sample.

The present disclosure is further directed to kit including the compounds of the present disclosure. In a related embodiment, the kit includes one or more compounds of formula (I)-(III). I another embodiment, the kit includes a composition including one or more compounds of formula (I)-(III) and/or one or more pharmaceutically acceptable salt, solvate, hydrate, prodrug or metabolite thereof. In a related embodiment, the kit includes one or more other therapeutic compounds or compositions for use in combination therapies.

In another embodiment, the kit can be a diagnostic kit including a detectably labeled compound of formula (I)-(III) for use as a diagnostic reagent. In another related embodiment, the labeled compound is biotinylated derivative of one or more compounds of formula (I), formula (II) and/or formula (III). In another embodiment, the kit includes a binding partner of the label of the labeled compound of formula (I)-(III).

Additional advantages of the present disclosure will become readily apparent to those skilled in this art from the following detailed description, wherein only the preferred embodiment of the disclosure is shown and described, simply by way of illustration of the best mode contemplated of carrying out the disclosure. As will be realized, the disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein:

FIG. 7(A) is a graph showing inhibition of CRC cell proliferation at 0.1, 0.3 and 1 µM of various compounds of the disclosure. FIG. 7(B) shows representative nude mice treated with compound 4r or corn oil after injection with LS174 CRC cells ($2\times10^6$) subcutaneously into both flanks. FIG. 7(C) is a graph of the body weights of nude mice treated with compound 4r and corn oil. FIG. 7(D) is a graph of tumor volume in mice treated with compound 4r or corn oil. Statistical significance was calculated by the student's t test (*$p<0.05$).

FIG. 9(A) shows a biotinylated derivative 13 of a halogenated stilbene analog of the present disclosure. FIG.

9(B) shows silver staining of protein markers (1), elutions from Biotin-stilbene analog-beads (2), Streptavidin beads alone (3) and unrelated biotin-labeled beads (4).

Figure 10:
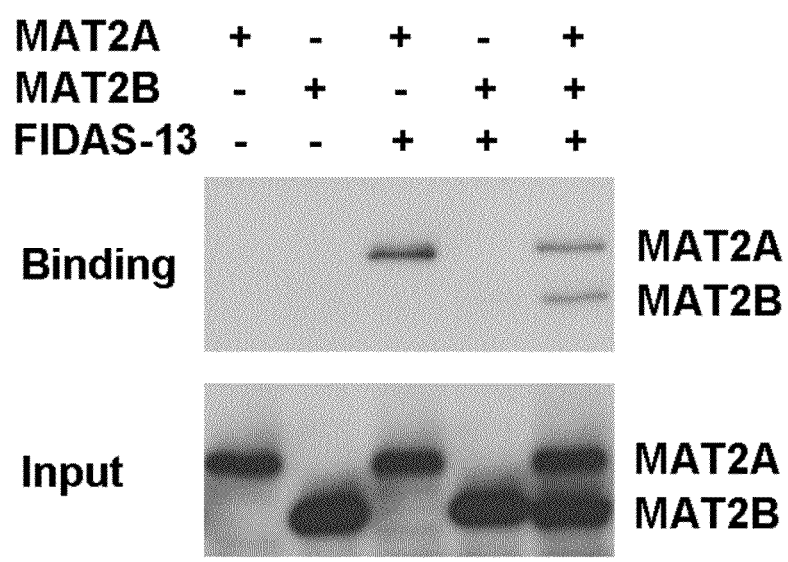

FIG. 10 shows halogenated stilbene analogs of the present disclosure directly interacted with MAT2A. GST-MAT2A and GST-MAT2B fusion proteins were expressed and purified from *E. coli*. These proteins were incubated with streptavidin beads with or without biotinylated derivative 13. The binding proteins were eluted by 2.5 mM D-biotin and analyzed by Western blot with an anti-GST-Ab.

Figure 11:
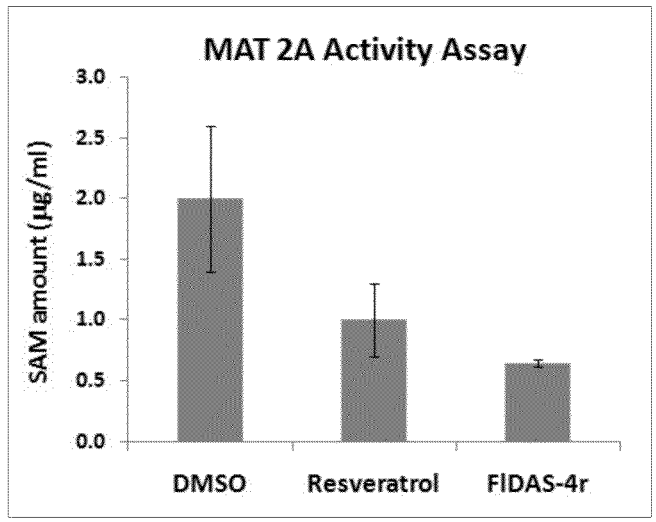
Figure 11:
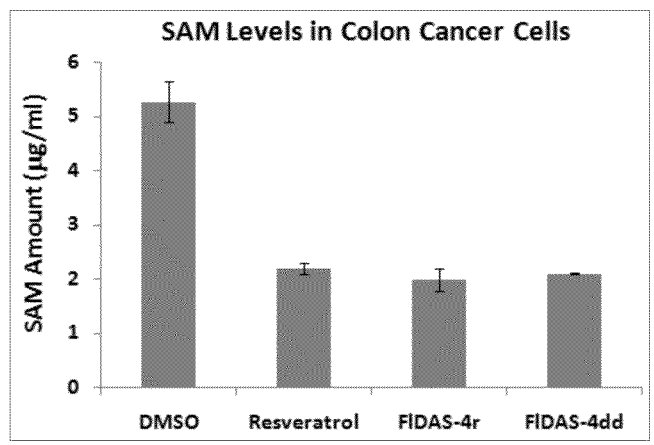
Figure 11:
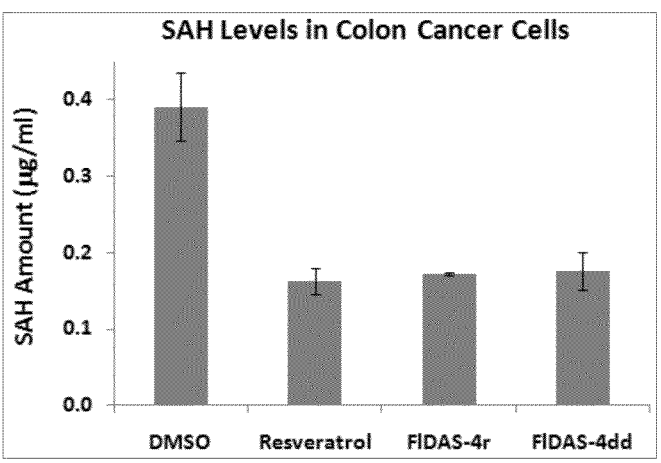

FIG. 11 shows that halogenated stilbenes are more potent than resveratrol in inhibiting the MAT2A activity in producing SAM and SAH. FIG. 11A shows the effects of 10 μM of compound 4r versus 30 μM of resveratrol on SAM levels in LS174 colon cancer cells. FIG. 11B shows the effects of 3 μM of compound 4dd and 10 μM of compound 4r versus 30 μM of resveratrol on SAM levels in colon cancer cells. FIG. 11C shows the effects of 3 μM of compound 4dd and 10 μM of compound 4r versus 30 μM of resveratrol on SAH levels in colon cancer cells.

Figure 12:
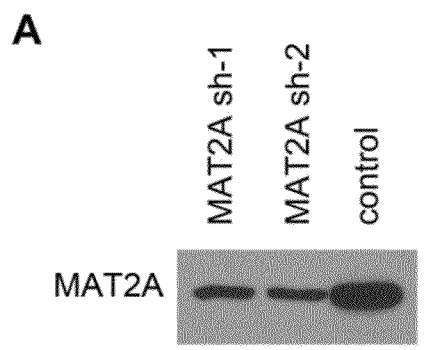
Figure 12:
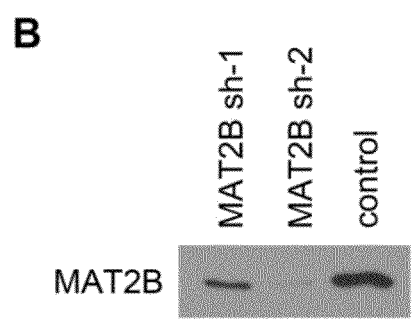
Figure 12:
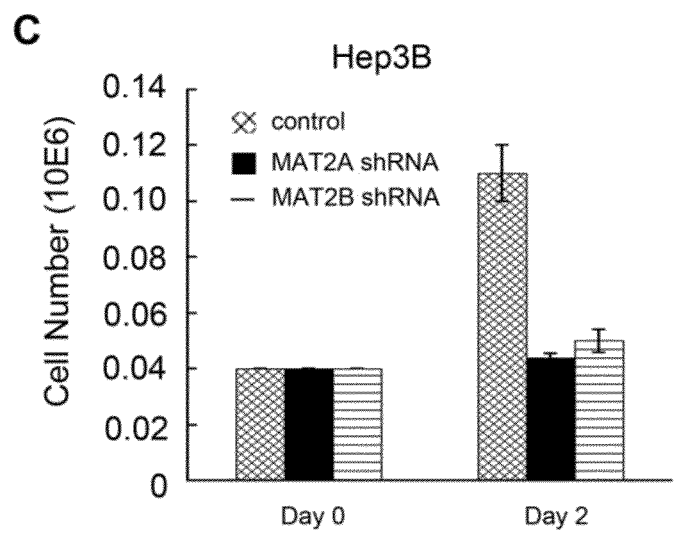

FIG. 12 shows that MAT2A and MAT2B are essential for cancer cell proliferation and their inhibition at a transcription level reduces cancer cell proliferation. Knocking down MAT2A gene (12A) and MAT2B gene (12B) with shRNAs are shown to inhibit proliferation of liver cancer cell line Hep3B (12C).

Figure 13:
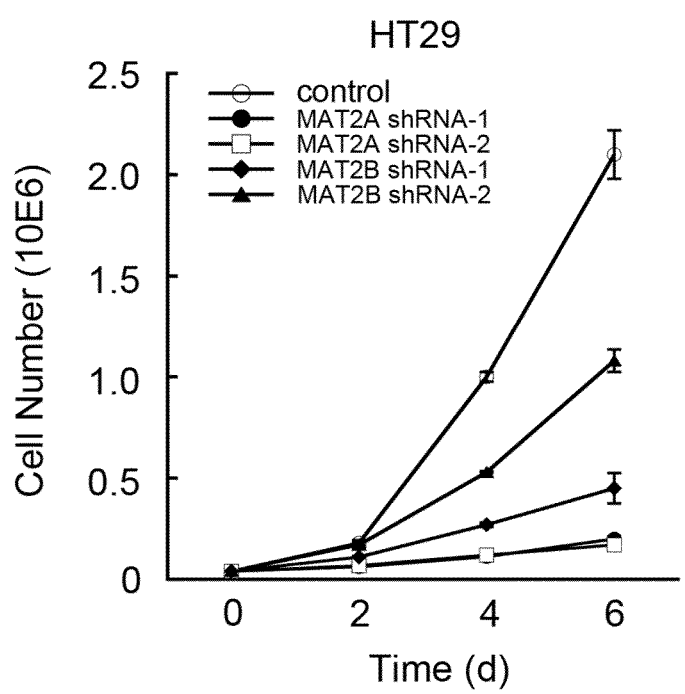
Figure 13:
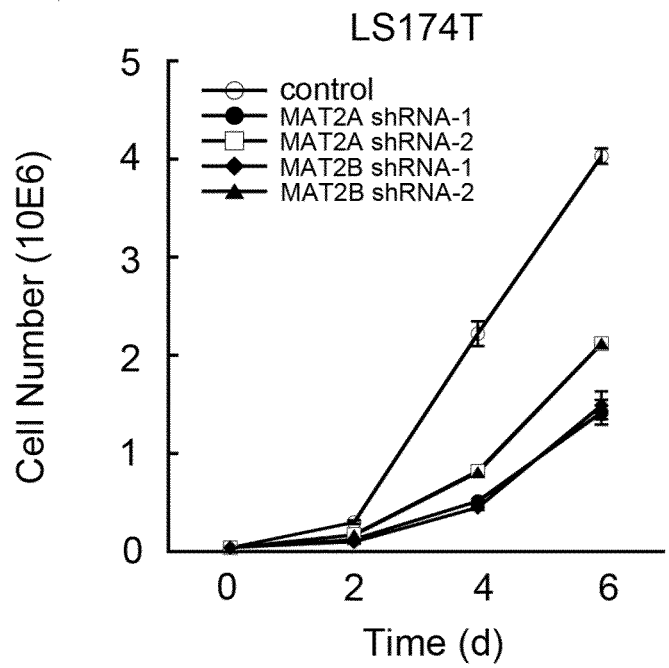

FIG. 13 shows a time-course study for the effects of the MAT2A and MAT2B genes inhibition on the proliferation of colon cancer cells. FIG. 13A shows inhibition of the HT29 cell proliferation by MAT2A and MAT2B shRNAs. FIG. 13B shows inhibition of the LS 174T cell proliferation by MAT2A and MAT2B shRNAs.

Figure 14:
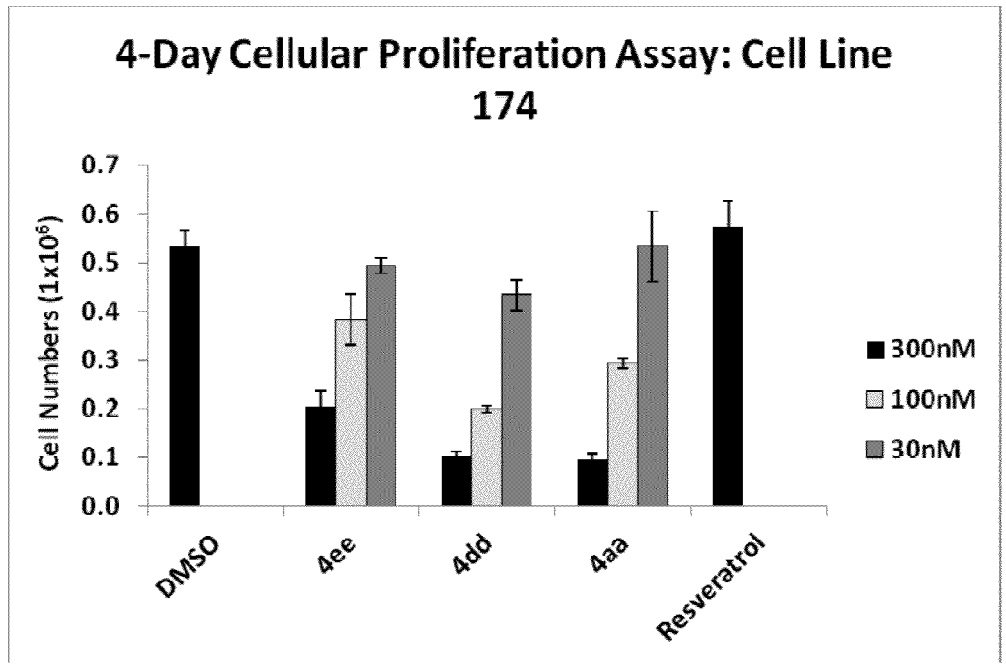

FIG. 14 is a chart showing that the halogenated stilbene analogs of the present disclosure inhibit proliferation of colon cancer cells.

Figure 15:
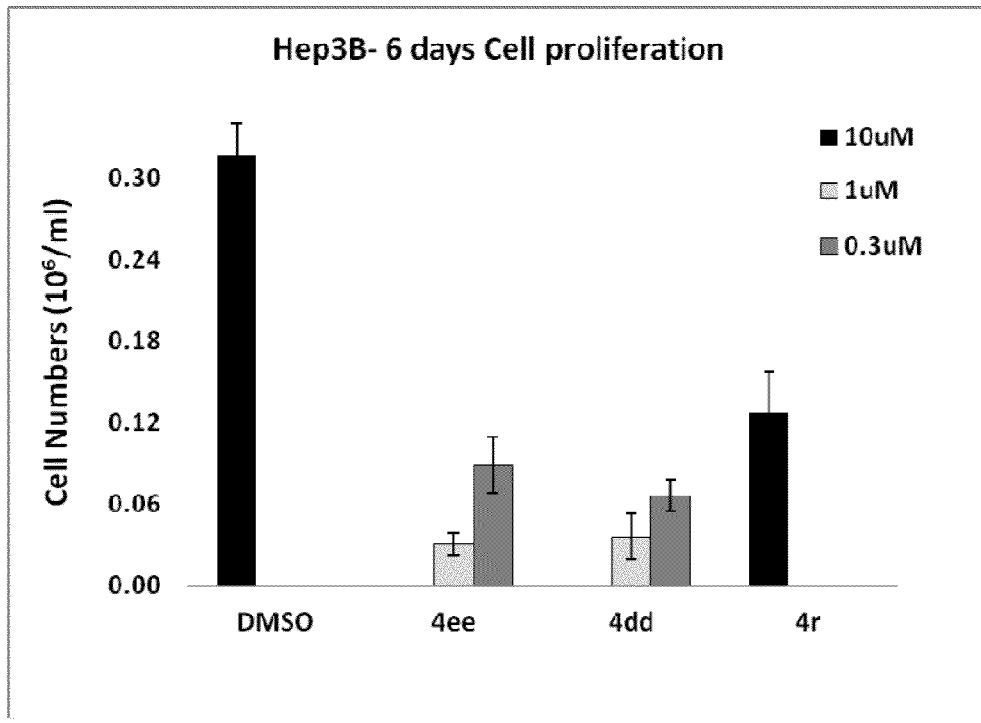

FIG. 15 is a chart illustrating that the halogenated stilbene analogs of the present disclosure inhibit proliferation of liver cancer cells.

Figure 16:
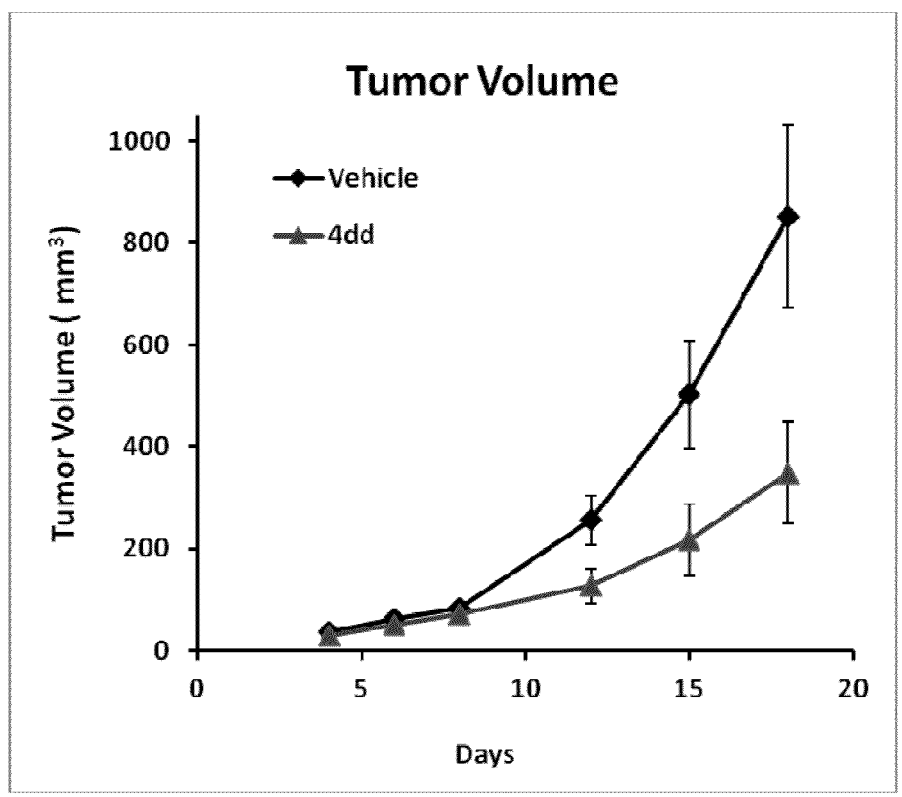

FIG. 16 is a chart showing the effect of the halogenated stilbene 4dd toward inhibition of xenograft tumors in nude mice.

Figure 17:
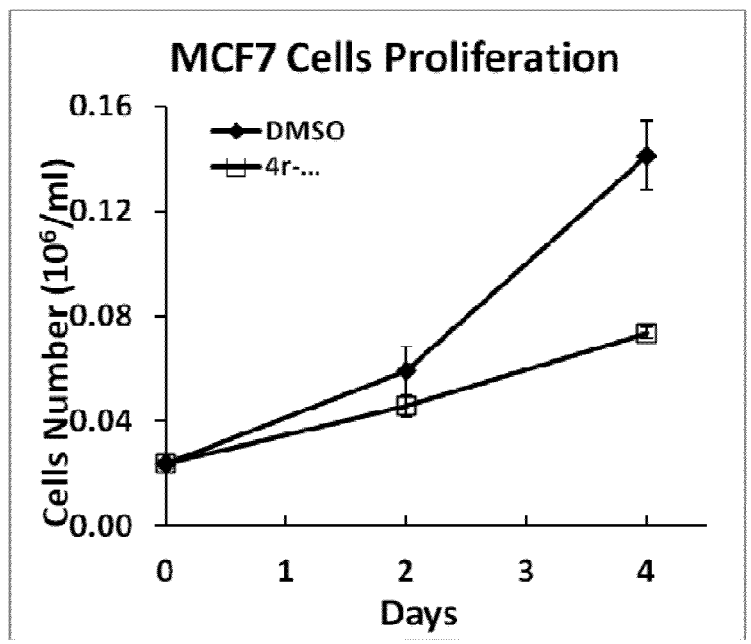
Figure 17:
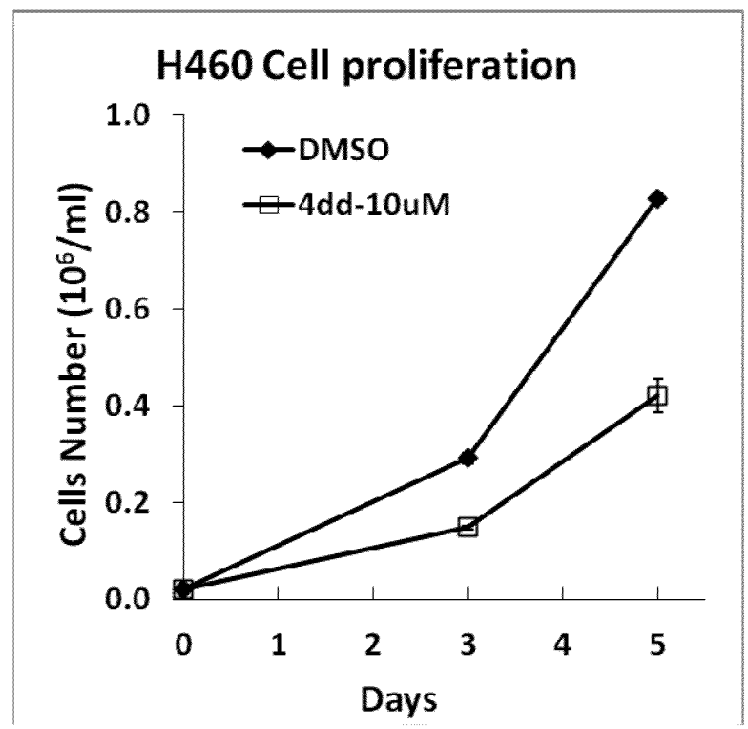
Figure 17:
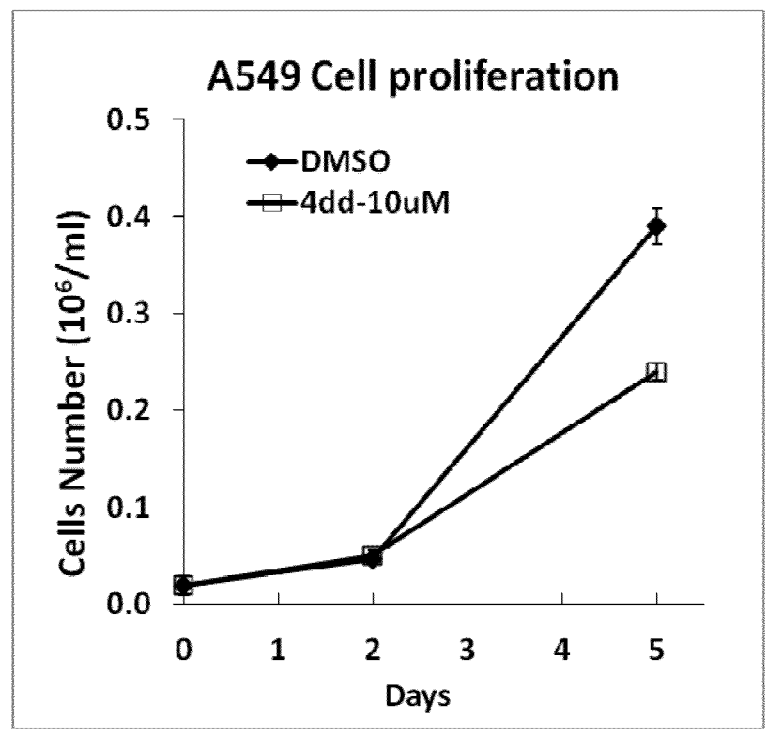
Figure 17:
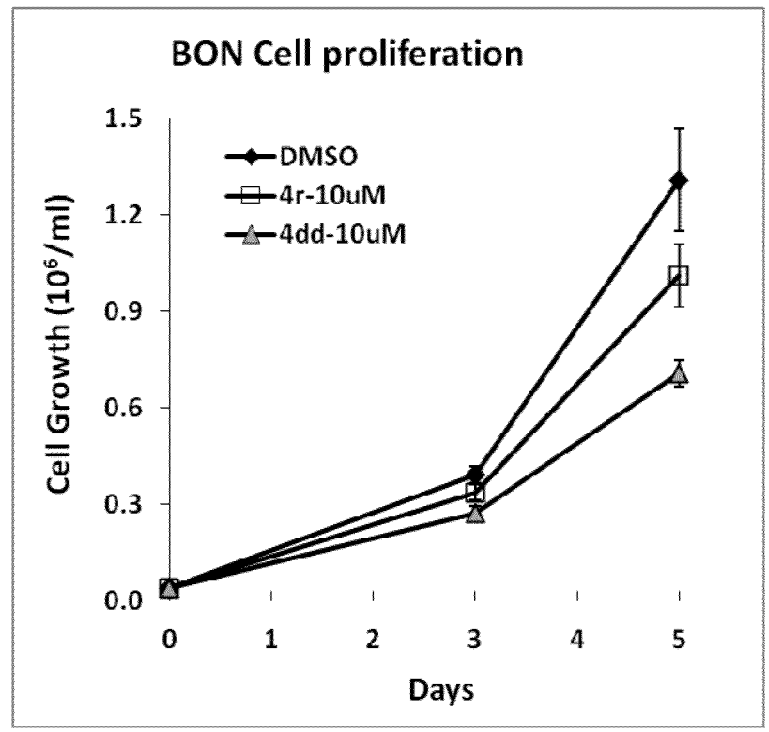
Figure 17:
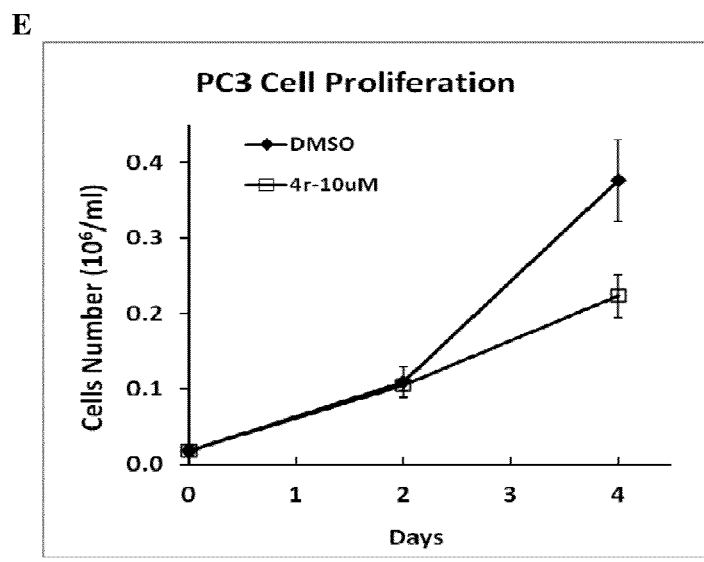

FIG. 17 shows the inhibitory effects of selected halogenated stilbene analogs on proliferation of breast cancer (17A), lung cancer (17B and 17C), carcinoid tumor (17D) and prostate cancer (17E) cell lines.

Figure 18:
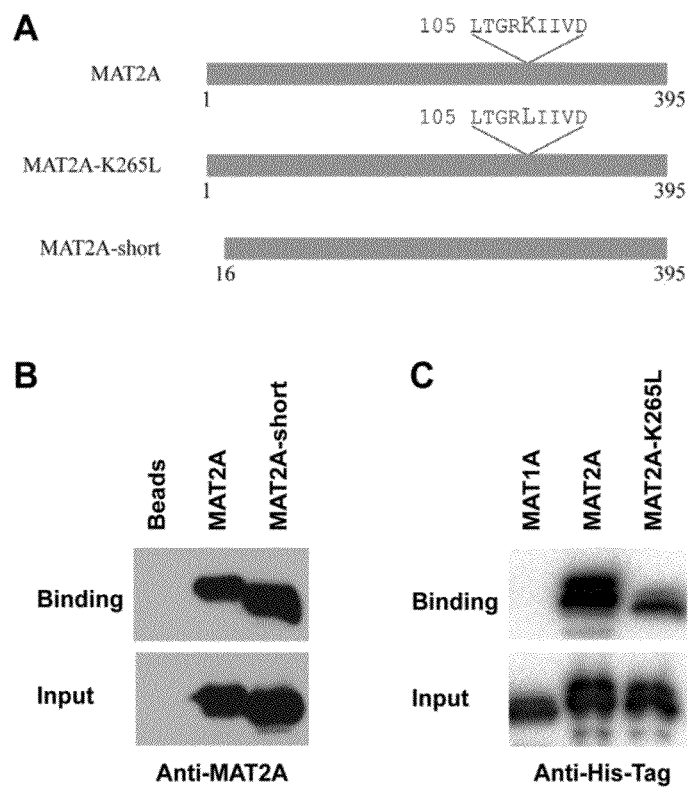

FIG. 18A shows a mutant MAT2A (K265L) that was prepared to conduct binding studies for the halogenated stilbene analogs. FIG. 18B shows that a terminal deletion of MAT2A (MAT2A-short) does not affect the binding of the halogenated stilbene analogs to MAT2A. FIG. 18C shows that mutant MAT2A (MAT2A-K265L) partially loses its ability to bind to halogenated stilbene analogs.

DETAILED DESCRIPTION OF THE DISCLOSURE

The present disclosure relates to novel inhibitors of the enzyme methionine adenosyltransferase 2A (MAT2A) (GeneID: 4144; nucleotide NM_005911; amino acid ID: NP_005902). These compounds are useful for treating or preventing any disease and/or condition, wherein modulation of MAT2A levels, and/or its enzymatic products (i.e., S-adenosyl-methionine (SAM or AdoMet)), is effective in ameliorating symptoms or diseases Inhibition of MAT2A can lead to decrease in SAM levels and a reduction in the methylation reactions or methylated products downstream of SAM. Thus, the disclosure provides compounds, compositions and methods for the treatment or prevention of disorders associated with MAT2A. Such diseases or disorders include, but not limited to, proliferative disorders such as cancer or metabolic disorders such as diabetes, heart disease, aging, obesity, and neurodegenerative disorders such as Alzheimer and Parkinson diseases.

Definitions

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" as used herein also includes halosubstituted alkyls.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons ($C_1$-$C_{10}$), e.g., from one to about six carbon atoms ($C_1$-$C_6$) in its backbone structure. Likewise, "lower alkenyl" "loweralkyl, "lower amino", "lower alkynyl", etc. have similar chain lengths.

The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

The term "treat" and "treatment" refer to both therapeutic treatment and prophylactic or preventative measures, wherein the object is to prevent or slow down (lessen) an undesired pathological change or disorder, such as the development or spread of cancer. For purpose of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, "treatment" can include a qualitative or quantitative reduction (e.g., by at least 10%, 20%, 30%, 40%, 50%, 60%, 70%, 80%, 90%, 95%, or more) in the tumor or metastases size or reduce or prevent metastatic growth. "Treatment" can also mean prolonging survival as compared to expected survival if not receiving treatment.

Those in need of treatment include those already with the condition or disorder as well as those prone to have the condition or disorder or those in which the condition or disorder is to be prevented.

The phrase "therapeutically effective amount" means an amount of a compound of the present disclosure that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may be reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatome, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "prodrug" as used in this application refers to a precursor or derivative form of a compound of the disclosure that may be less cytotoxic to cells compared to the parent compound or drug and is capable of being enzymatically or hydrolytically activated or converted into the more active parent form. The prodrugs of this disclosure include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound.

The term "complex protein sample" is used to distinguish a sample from a purified protein sample. A complex protein sample contains multiple proteins, and may additionally contain other contaminants. Non-limiting examples of a complex protein samples include tumor tissues, biopsy samples, serum or cell extracts.

By "reference sample" is meant any sample, standard, or level that is used for comparison purposes. A "normal reference sample" can be a prior sample taken from the same subject, a sample from a subject not having cancer, a subject that is diagnosed with cancer but not a metastatic disease, a subject that has been treated for either cancer, metastatic disease, or both, a subject that has a benign tumor, or a sample of particular tissues from one or more healthy subjects, or a pooled sample of tissues from one or more healthy subjects.

The phrase "biological activity of MAT2A" or "MAT2A biological activity" as used herein, refers to all inherent biological properties of methionine adenosyltransferase 2A (MAT2A) enzyme. Biological properties of MAT2A include but are not limited to catalyzing the transfer of the adenosyl group of ATP to the sulfur atom of methionine and producing S-adenosyl-methionine (SAM or AdoMet); involving in an abnormal cell growth and proliferation in cancer cells; facilitating intracellular methylation reactions through the action of SAM as a methyl group donor.

The term "labeled" or "detectably labeled" as used herein means joining, either covalently or non-covalently to the compounds of the present disclosure, a substance which elicits a physical or chemical response that can be observed or detected by a binding partner such as biotin/streptavidin, antigen/antibody or by means of instrumentation such as, without limitation, UV/Vis spectrophotometers, flow cytometers, fluorescence detection instruments and the like, by the naked eye. A wide variety of labels and labeling techniques are well known in the art. Suitable labels include biotin, radionuclides, e.g., 32P, 35S, 3H, enzymes, substrates, cofactors, inhibitors, fluorescent moieties, chemiluminescent moieties, magnetic particles, and the like.

The phrase "binds to" when referring to the binding of the labeled compounds of the present disclosure to MAT2A for detection purposes, refers to a binding reaction which is determinative of the presence of the MAT2A in the presence of a heterogeneous population of proteins and other biologics. Thus, under binding assay conditions, for example, a labeled compound of the present disclosure binds to MAT2A and does not bind in a significant amount to other proteins present in the sample. A variety of conventional detection means can be used for detecting the binding of the labeled compounds to MAT2A, such as western blot, flow cytometry and FACS analysis, immunohistochemistry and the like. See, e.g., Harlow and Lane Antibodies, A Laboratory Manual., Cold Spring Harbor Publications, NY (1988) for a description of, e.g., western blot or immunofluorescence assay. Typically, a specific or selective binding reaction will be at least twice the background signal or noise and more typically more than 10 to 100 times background.

Accordingly, the disclosure includes metabolites of compounds of the disclosure, including compounds produced by a process comprising contacting a compound of this disclosure with a mammal for a period of time sufficient to yield a metabolic product thereof.

Therapeutic Agents

Disclosed herein are halogenated stilbene analogs and their use in mitigating hyperproliferating cells or treating diseases or disorders associated with MAT2A activity. The halogenated stilbene analogs of the present disclosure display anti-tumor activity, i.e., cancer cells that are exposed to the compounds are killed, damaged and/or tumor growth is inhibited. The analogs are useful for treatment of human cancers including colorectal cancer, liver, breast cancer, among others.

The halogenated stilbene analogs of the present disclosure include compounds according to formula (I):

$$X-Ar_1-CR^a=CR^b-Ar_2 \qquad (I)$$

where $R^a$ and $R^b$ are independently H, alkyl, halo, alkoxy, cyano; X represents at least one halogen, e.g., a fluorine, chlorine, bromine, or iodine substituent, on $Ar_1$; each of $Ar_1$ and $Ar_2$ are aryl, e.g., phenyl, naphthyl, and heteroaryl, e.g., pyridyl, pyrolidyl, piperidyl, pyrimidyl, indolyl, thienyl, which can be further substituted with halo, amino, alkylamino, dialkylamino, arylalkylamino, N-oxides of dialkylamino, trialkylammonium, mercapto, alkylthio, alkanoyl, nitro, nitrosyl, cyano, alkoxy, alkenyloxy, aryl, heteroaryl, sulfonyl, sulfonamide, $CONR_{11}R_{12}$, $NR_{11}CO(R_{13})$, $NR_{11}COO(R_{13})$, $NR_{11}CONR_{12}R_{13}$ where $R_{11}$, $R_{12}$, $R_{13}$, are independently, H, alkyl, aryl, heteroaryl or a fluorine; provided that $Ar_2$ contains at least one nitrogen atom in the aryl ring or at least one nitrogen substituent on the aryl ring; e.g., an $NR^cR^dZ$ substituent on $Ar_2$ where $R^c$ is H, alkyl, alkoxy, aryl, heteroaryl, $R^d$ is an alkyl group, Z is a an unshared pair of electrons, H, alkyl, oxygen. Preferably, the heteroaryl group is a monocyclic ring, wherein the ring comprises 2 to 5 carbon atoms and 1 to 3 heteroatoms, referred to herein as "$(C_2-C_5)$ heteroaryl". This embodiment also includes a pharmaceutically acceptable salt of formula (I) and a biotinylated derivative of formula (I). The substituents on the carbon-carbon double bond can be in either the cis- or trans-configuration. In one aspect of the present disclosure, X is one, two or three fluorine substituents and/or X is one, two or three chlorine substituents and/or X represents at least one fluorine and at least one chlorine on $Ar_1$. In another aspect of the present disclosure, X is one or more fluorine and/or chlorine and $R^c$ is H or a lower alkyl and $R^d$ is a lower alkyl, or a pharmaceutically acceptable salt thereof, or a biotinylated derivative thereof.

In another embodiment, the present disclosure includes compounds of formula (II):

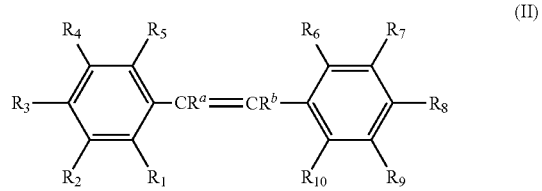

(II)

where $R^a$ and $R^b$ are as defined above, $R_1$ to $R_{10}$ are independently H, halo, amino, alkylamino, dialkylamino, N-oxides of dialkylamino, arylalkylamino, dialkyloxyamino, trialkylammonium, mercapto, alkylthio, alkanoyl, nitro, nitrosyl, cyano, alkoxy, alkenyloxy, aryl, heteroaryl, sulfonyl, sulfonamide, $CONR_{11}R_{12}$, $NR_{11}CO(R_{13})$, $NR_{11}COO(R_{13})$, $NR_{11}CONR_{12}R_{13}$ where $R_{11}$, $R_{12}$, $R_{13}$, are independently, H, alkyl, aryl, heteroaryl or a fluorine; provided at least one of $R_1$ to $R_5$ is a halogen, e.g. a fluorine and/or chlorine; and at least one of $R_6$ to $R_{10}$ is a nitrogen containing substituent, e.g., an $NR^cR^dZ$ substituent where $R^c$ is H, alkyl, e.g., a lower alkyl, alkoxy, aryl, heteroaryl, $R^d$ is an alkyl group, Z is a an unshared pair of electrons, H, alkyl, oxygen, or a pharmaceutically acceptable salt thereof, or a biotinylated derivative thereof.

In other embodiments of the present disclosure, at least one of $R_1$ to $R_5$ is a chlorine and/or fluorine substituent; at least one of $R_6$ to $R_{10}$ is $NR^cR^dZ$ where $R^c$ is H or lower alkyl and $R^d$ is a lower alkyl. In certain embodiments, one, two or three of $R_1$ to $R_5$ is a fluorine or a chlorine group; while in certain embodiments $R_1$ and $R_5$ are each fluorine and/or chlorine groups, e.g., $R_1$ and $R_5$ are either two fluorine, two chlorine or one each of fluorine and chlorine groups. In another embodiment $R_1$ and $R_4$ are each fluorine and/or chlorine groups, e.g. $R_1$ and $R_4$ are either two fluorine, two chlorine or one each of fluorine and chlorine groups.

In another embodiments, the present disclosure includes compounds according to formula (III):

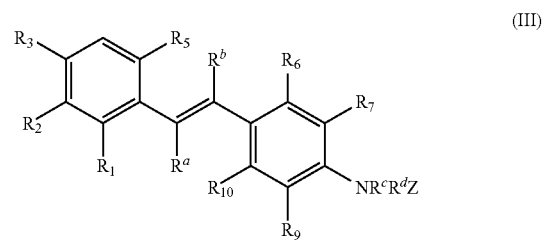

(III)

where $R_1$, $R_2$, $R_3$, $R_5$, $R_6$, $R_7$, $R_9$, $R_{10}$, $R^a$, $R^b$ and $NR^cR^dZ$ are the same as defined above, or pharmaceutically acceptable salts thereof, or a biotinylated derivative thereof. In one aspect of the present disclosure, $R^a$, $R^b$ are both H, one or more of $R_1$, $R_2$, $R_3$, or $R_5$, are fluorine or chlorine and $R^c$ is H or lower alkyl, such as a methyl, ethyl, propyl group, and $R^d$ is a lower alkyl, such as a methyl, ethyl, propyl group. In another aspect of the present disclosure, $R^a$, $R^b$ are both H, and at least two of $R_1$, $R_2$, $R_3$, or $R_5$ are fluorine and/or chlorine, or a pharmaceutically acceptable salt thereof, or a biotinylated derivative thereof.

In another embodiment of the present disclosure, the halogenated stilbene analog is a dihalogenated N,N-dimethylaminostyrene having at least one fluorine or chlorine is in the 2' or 3' position of the aryl ring. In another embodiment, the stilbene analog has a fluorine in the 2' position and another fluorine in the 6' position. In another embodiment, the stilbene analog has a fluorine in the 2' position and a chlorine in the 6' position. In another embodiment, the stilbene analog has a chlorine in the 2' position and another chlorine in the 6' position.

In another embodiment, the stilbene analog is a dihalogenated N-methylaminostyrene in with at least one fluorine or chlorine is in the 2' or 3' position.

Particular halogenated stilbene analogs of the present disclosure include (E)-4-(2-Fluorostyryl)-N,N-dimethylaniline; (E)-4-(3-Fluorostyryl)-N,N-dimethylaniline; (E)-4-(4-Fluorostyryl)-N,N-dimethylaniline; (E)-4-(2-Fluorostyryl)-N,N-diethylaniline; (E)-4-(2-Fluorostyryl)-N,N-diphenyl aniline; (E)-1-(4-(2-Fluorostyryl)phenyl)-4-methylpiperazine; (E)-4-(2-Fluorostyryl)-N,N-dimethylnaphthalen-1-amine; (E)-2-(4-(2-Fluorostyryl)phenyl)-1-methyl-1H-imidazole; (E)-4-(2,3-Difluorostyryl)-N,N-dimethylaniline; (E)-4-(2,4-Difluorostyryl)-N,N-dimethylaniline; (E)-4-(2,5-Difluorostyryl)-N,N-dimethylaniline; (E)-2-(2,6-Difluorostyryl)-N,N-dimethylaniline; (E)-3-(2,6-Difluorostyryl)-N,N-dimethylaniline; (E)-4-(2,6-Difluorostyryl)-N,N-dimethylaniline; (E)-4-(2,6-Difluorostyryl)-N,N-diethylaniline; (E)-4-(3,4-Difluorostyryl)-N,N-dimethylaniline; (E)-4-(3,5-Difluorostyryl)-N,N-dimethylaniline; (E)-N,N-Dimethyl-4-(2,3,6-trifluorostyryl)aniline; (E)-N,N-Dimethyl-4-(2,4,6-trifluorostyryl)aniline; (E)-4-(2-chloro-6-fluorostyryl)-N,N-dimethylaniline; (E)-4-(2,6-dichlorostyryl)-N,N-dimethylaniline; (E)-4-(2,6-Difluorophenethyl)-N,N-dimethylaniline; and (E)-2-benzamide-4-(2,6-difluorostyryl)-N,N-dimethylaniline.

Synthesis

The compounds of the present disclosure, including compounds of Formula (I) to Formula (III), may be prepared by methods disclosed herein or any other method known in the art. One of ordinary skill in the art will know how to modify procedures to obtain the analogs of the present disclosure. In addition, compounds may be prepared using the methods described below and in Examples 1 through 3 or modified versions thereof.

Figure 1:
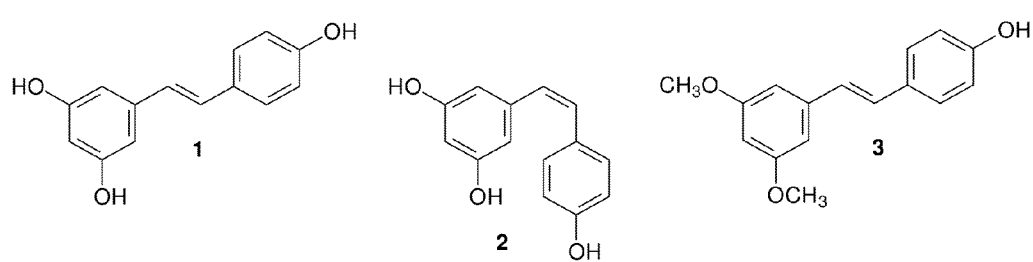
FIG. 1 shows the structures of naturally occurring stilbenes with antineoplastic activity. Structure 1 is a trans-resveratrol, 2 is cis-resveratrol and 3 is pterostilbene.
Figure 2:
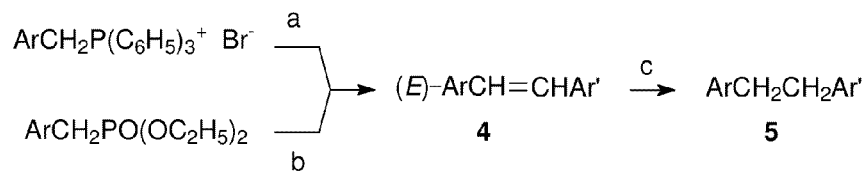
FIG. 2 is a schematic drawing of the general synthesis of certain stilbene analogs and 1,2-diarylethanes. Legend: a, (1) n-BuLi, THF; (2) ArCHO; b, (1) NaH, DMF; (2) ArCHO; c, $H_2$, Pd—C, THF.

FIG. 2 is a schematic of the general synthesis of certain halogenated stilbene analogs of the present disclosure. Additional halogenated stilbene analogs of the present disclosure can be made by similar methods or known synthetic procedures known in the art in light of the present disclosure. For example, as shown in FIG. 2 either Wittig or Wadsworth-Emmons reactions using phosphonium salts or diethyl phosphonates, respectively, with aldehydes provided the (E)-stilbenes (4) in good yield. The phosphonium salts were prepared from the corresponding benzyl bromides and triphenylphosphine, and the diethyl phosphonates were prepared from the corresponding benzyl bromides and triethyl phosphite using the Arbuzov reaction according to standard literature procedures. Compounds were characterized fully and purity (>95%) established through combustion analyses.

The terms ortho, meta and para are art-recognized term and refer to 1,2-, 1,3- and 1,4-disubstituted benzenes, respectively. For example, the names 1,2-dimethylbenzene and ortho-dimethylbenzene are synonymous.

The present disclosure also encompasses potential metabolites of the halogenated stilbene analogs. These include stilbene analogs, e.g., general formulae (I), (II) or (III), having a dialkyamino substituent which has undergone an oxidation to an N-oxide. In one embodiment, the compound is the N-oxide of the dihalogenated N,N-dimethylaminostyrene having at least one fluorine or chlorine is in the 2' or 3' position. These potential metabolites also include halogenated stilbene analogs having a N,N-dialkylamino group which has undergone a methylation or a demethylation. In one embodiment, the stilbene analog is a dihalogenated N,N,N-trimethylammoniumstyrene halide having at least one fluorine or chlorine is in the 2' or 6' position. In one embodiment, the analog is a dihalogenated N-methylaminostyrene having at least one fluorine or chlorine is in the 2' or 3' position. In one embodiment, the analog is a dihalogenated N,N-methylhydroxyaminostyrene having at least one fluorine or chlorine in the 2' or 3' position.

The present disclosure also encompasses biotinylated derivatives of the halogenated stilbene analogs. Such biotinylated derivatives are useful in identifying the molecular target for these agents. Stilbene analogs encompassed by formulas (I), (II) and (III) were synthesized and converted to biotinylated derivatives. The biotinylated derivatives that retain biological activity were used to identify a molecular enzyme target for these compounds, methionine S-adenosyltransferase.

In certain embodiments of the present disclosure, the halogenated stilbene analogs of the disclosure, or a pharmaceutically acceptable salt, solvate, hydrate or prodrug thereof, inhibit the growth of hyperproliferative cells. In certain embodiments of the present disclosure, the halogenated stilbene analogs of the disclosure, or a pharmaceutically acceptable salt, solvate, hydrate or prodrug thereof, inhibit methionine adenosyltransferase 2A (MAT2A) activity and are useful in treating diseases or conditions associated with MAT2A, e.g., diseases and conditions whose maintenance and/or spread require MAT2A.

Metabolites of Compounds of the Disclosure

Also falling within the scope of this disclosure are the in vivo metabolic products of formulas (I) to (III) described herein. Such products may result for example from the oxidation, reduction, hydrolysis, amidation, deamidation, esterification, deesterification, enzymatic cleavage, and the like, of the administered compound.

Accordingly, the disclosure includes metabolites of compounds of formulas (I) to (III), including compounds produced by a process comprising contacting a compound of this disclosure with a mammal for a period of time sufficient to yield a metabolic product thereof.

Figure 3:
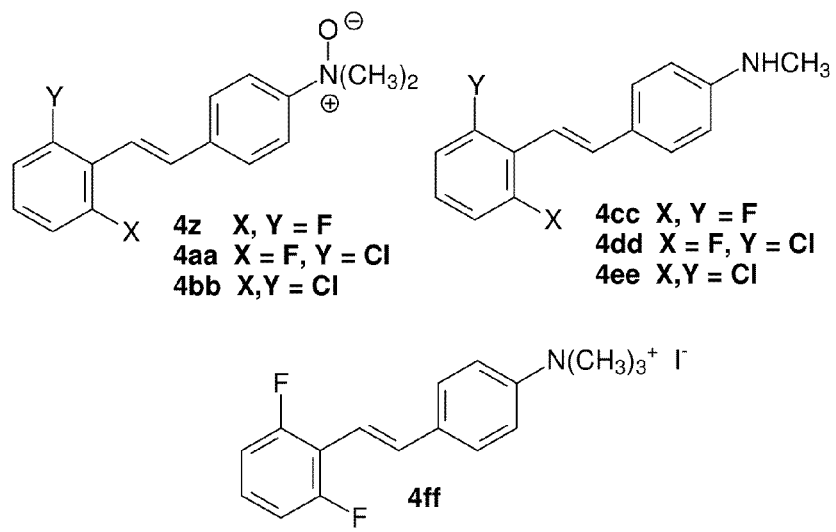
FIG. 3 shows the chemical structures of several potential metabolites of fluorinated and/or chlorinated stilbene analogs of the present disclosure.

Metabolite products typically are identified by preparing a detectably labeled, for example a radiolabeled (e.g., C or H isotope) compound of the disclosure, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are detectably labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies, which are well known to those skilled in the art. The metabolite products, so long as they are not otherwise found in vivo, are useful in diagnostic assays for therapeutic dosing of the compounds of the disclosure. Examples of likely metabolites of compounds of formulas (I) to (III) are shown in FIG. 3 and synthesized according to Example 2.

Prodrugs of the Compounds of the Disclosure

In addition to compounds of the disclosure, the disclosure also includes pharmaceutically acceptable prodrugs of such compounds. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present disclosure. The amino acid residues include but are not limited to the 20 naturally occurring amino acids commonly designated by three letter symbols and also includes phosphoserine, phosphothreonine, phosphotyrosine, 4-hydroxyproline, hydroxyzine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the disclosure can be derivatized as an amide or alkyl ester. As another example, compounds of this disclosure comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in Advanced Drug Delivery Reviews, (1996) 19:1-15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom with a group such as (C1-C6)alkanoyloxymethyl, 1-((C1-C6)alkanoyloxy)ethyl, 1-methyl-1-((C1-C6)

alkanoyloxy)ethyl, (C1-C6)alkoxycarbonyloxymethyl, N—(C1-C6)alkoxycarbonylaminomethyl, succinoyl, (C1-C6)alkanoyl, α-amino(C1-C4)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C1-C6)alkyl)2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Pharmaceutical Compositions

The present disclosure also encompasses pharmaceutical compositions comprising at least one halogenated stilbene analog, e.g., one or more compounds of formula (I), formula (II) and/or formula (III) and/or one or more pharmaceutically acceptable salts of compounds according to formulae (I), (II) and/or (III), in combination with a pharmaceutical carrier. In one aspect of the present disclosure, the pharmaceutical compositions comprise an effective amount of at least one halogenated stilbene analog. In another embodiment of the present disclosure, the pharmaceutical composition comprises a dihalogenated N,N-dialkylaminostilbene analog and a pharmaceutically acceptable carrier.

While it may be possible for compounds of the present disclosure to be administered as the raw chemical, it is preferable to present them as a pharmaceutical composition. According to a further aspect, the present disclosure provides a pharmaceutical composition comprising a compound or mixture of compounds of Formula (I) to Formula (III) or a pharmaceutically acceptable salt, solvate, hydrate, prodrug or metabolite thereof, together with one or more pharmaceutical carrier, excipient or additive and optionally one or more other therapeutic ingredients. The carrier(s) must be "acceptable" in the sense of being compatible with the other ingredients of the formulation and not deleterious to the recipient thereof. The term "pharmaceutically acceptable carrier" includes vehicles and diluents.

To prepare the pharmaceutical compositions, a therapeutically effective amount of one or more of the halogenated stilbene analogs according to the present disclosure may be intimately admixed with a pharmaceutically acceptable carrier according to conventional pharmaceutical compounding techniques to produce a dose. A carrier may take a wide variety of forms depending on the form of preparation desired for administration, e.g., oral, topical or parenteral, including gels, creams ointments, lotions and time released implantable preparations, among numerous others. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

In one embodiment, the compositions are prepared with carriers that will protect the active compound(s) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The pharmaceutically acceptable carrier may take a wide variety of forms, depending on the route desired for administration, for example, oral or parenteral (including intravenous). Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by standard aqueous or nonaqueous techniques. Oral and parenteral sustained release dosage forms may also be used.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension. Other methods of preparation well known by those of ordinary skill may also be used in this aspect of the present disclosure.

In an embodiment, the composition of the present disclosure enables sustained, continuous delivery of a compound of Formula (I) to Formula (III) or a pharmaceutically acceptable salt, solvate, hydrate, prodrug or metabolite thereof, to tissues adjacent to or distant from an administration site. The biologically-active agent is capable of providing a local or systemic biological, physiological or therapeutic effect. For example, a compound of Formula (I) to Formula (III) or a pharmaceutically acceptable salt, solvate, hydrate, prodrug or metabolite thereof, may act to kill cancer cells, or cancer stem cells or to control or suppress tumor growth or metastasis, among other functions.

Formulations and Dosages for Administration

Pharmaceutical formulations based upon halogenated stilbene compounds of the present disclosure comprise at least one of the compounds of Formula (I) to Formula (III) or a pharmaceutically acceptable salt, solvate, hydrate, prodrug or metabolite thereof, in a therapeutically effective amount for treating neoplasia, cancer and other diseases and conditions associated with MAT2A activity such as diabetes, heart disease, aging, obesity, Alzheimer's disease or Parkinson disease, optionally in combination with a pharmaceutically acceptable additive, carrier and/or excipient. One of ordinary skill in the art will recognize that a therapeutically effective amount of one of more compounds according to the present disclosure will vary with the condition to be treated, its severity, the treatment regimen to be employed, the pharmacokinetics of the agent used, as well as the patient (animal or human) treated.

The formulations of the present disclosure include those suitable for oral, parenteral (including subcutaneous, intradermal, intramuscular, intravenous, intratumoral and intraarticular), rectal and topical (including dermal, buccal, sublingual and intraocular) administration, as well as those for administration by inhalation. The most suitable route may depend upon the condition and disorder of the recipient. Exemplary formulations are well known to those skilled in the art, and general methods for preparing them are found in any standard pharmacy school textbook, for example, Remington: THE SCIENCE AND PRACTICE OF PHARMACY, 21st Ed., Lippincott. The formulations of the present disclosure may conveniently be presented in unit dosage form and may be prepared by any of the methods well known in the art of pharmacy. All methods include the step of bringing into association a compound or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Oral formulations are well known to those skilled in the art, and general methods for preparing them are found in any standard pharmacy school textbook, for example, Remington: THE SCIENCE AND PRACTICE OF PHARMACY, 21st Ed., the entire disclosure of which is incorporated herein by reference.

The concentration of active compound of the present disclosure, i.e., at least one of the compounds of Formula (I) to Formula (III) or a pharmaceutically acceptable salt, solvate, hydrate, prodrug or metabolite thereof, in the drug composition will depend on absorption, distribution, inactivation, and excretion rates of the drug as well as other factors known to those of skill in the art. It is to be noted that dosage values will also vary with the severity of the condition to be alleviated. The composition may be administered at once, or may be divided into a number of smaller doses to be administered at varying intervals of time.

Oral compositions will generally include an inert diluent or an edible carrier. They may be enclosed in gelatin-capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following non-limiting ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or fruit flavoring. When the dosage unit form is a capsule, it can contain, in addition to any of the above, a liquid carrier such as a fatty oil. In addition, dosage unit forms can contain various other materials which modify the physical form of the dosage unit, for example, coatings of sugar, shellac, or enteric agents.

The tablets, for example, may optionally be coated or scored and may be formulated so as to provide sustained, delayed or controlled release of the active ingredient therein. Oral and parenteral sustained release drug delivery systems are well known to those skilled in the art, and general methods of achieving sustained release of orally or parenterally administered drugs are found, for example, in Remington: THE SCIENCE AND PRACTICE OF PHARMACY, 21st Ed.

The active compound may also be administered as a component of an elixir, suspension, syrup, wafer or the like. A syrup may contain, in addition to the active compounds, sucrose or fructose as a sweetening agent and certain preservatives, dyes and colorings and flavors.

In certain embodiments of the present disclosure, the halogenated stilbene analog is formulated as admixture with a pharmaceutically acceptable carrier, excipient or additive. In general, the pharmaceutical composition is administered in orally-administrable form, but for treatment of a number of conditions, a number of other formulations may be administered via a topical, parenteral, intravenous, intramuscular, transdermal, buccal, subcutaneous, suppository or other route, including an eye or ocular route. Intravenous and intramuscular formulations are generally administered in sterile saline. Of course, one of ordinary skill in the art may modify the formulations within the teachings of the specification to provide numerous formulations for a particular route of administration without rendering the pharmaceutical compositions unstable or compromising their therapeutic activity. It is also well within the routineer's skill to modify the route of administration and dosage regimen of a particular compound in order to manage the pharmacokinetics of the present compounds for maximum beneficial effect to the patient.

In certain pharmaceutical dosage forms, the pro-drug form of the compounds may be preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

Pharmaceutical compositions containing any of the compounds of Formula (I) to Formula (III) or a pharmaceutically acceptable salt, solvate, hydrate, prodrug or metabolite thereof, may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 0.1 mg per day to about 7000 mg per day, or about 0.1 mg per day to about 100 mg per day, or from about 10 mg per day to about 100 mg per day, or from about 20 mg to about 100 mg, to about 80 mg or to about 60 mg. In some embodiments, the total daily dose may range from about 10 mg to about 500 mg per day, or about 100 mg to about 500 mg per day. It is further recommended that children, patients over 65 years old, and those with impaired renal or hepatic function, initially receive low doses and that the dosage be titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Alternatively, the maximum safe starting dose of the compounds of the present disclosure for use in initial clinical trials in adults may be determined by following, for example, the FDA guidelines for estimating maximum safe dosage. These guidelines provide guidance for using the dosages used in animal studies to extrapolate safe dosage for use in human trials. See Guidance for Industry, Estimating the Maximum Safe Starting Dose in Initial Clinical Trials for Therapeutics in Adult Healthy Volunteers, Food and Drug Administration, Center for Drug Evaluation and Research (CDER), July 2005.

In an embodiment, the amount of compound included within therapeutically effective formulations of the present disclosure is an effective amount for treating the conditions associated with MAT2A activity. In general, a therapeutically effective amount of the present preferred compound in dosage form usually ranges from slightly less than about 0.025 mg/kg to about 2.5 g/kg, and in certain embodiments about 2.5 to about 5 mg/kg or about 2.5 to about 100 mg/kg of the patient or considerably more, depending upon the compound used, the condition being treated and the route of administration, although exceptions to this dosage range may be contemplated by the present disclosure. In some embodiments, halogenated stilbene analogs of the present disclosure are administered in amounts ranging from about 0.1 mg/kg to about 100 mg/kg.

The active compound of the present disclosure, i.e., at least one of the compounds of Formula (1) to Formula (III) or a pharmaceutically acceptable salt, solvate, hydrate, prodrug or metabolite thereof, is included in the pharmaceutically acceptable carrier or diluent in an amount sufficient to deliver to a patient a therapeutically effective amount for the desired indication, without causing serious toxic effects in the patient treated.

In certain embodiments, the active compound is conveniently administered in any suitable unit dosage form, including but not limited to one containing 1 to 3000 mg, preferably 5 to 500 mg of active ingredient per unit dosage form. An oral dosage of 10-250 mg is usually convenient.

The actual dosage amount of a composition of the present disclosure administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound, i.e., at least one of the compounds of Formula (I) to Formula (III) or a pharmaceutically acceptable salt, solvate, hydrate, prodrug or metabolite thereof. In other embodiments, the active compound may comprise between about 1% to about 75% of the weight of the unit, or between about 5% to about 50%, for example, and any range derivable therein. In other non-limiting examples, a dose may also comprise about 1 microgram/kg/body weight, about 5 microgram/kg/body weight, about 10 microgram/kg/body weight, about 50 microgram/kg/body weight, about 100 milligram/kg/body weight, about 150 milligram/kg/body weight, about 200 milligram/kg/body weight, about 300 milligram/kg/body weight, about 400 milligram/kg/body weight or more per administration, and any range derivable therein. In non-limiting examples of a derivable range from the numbers listed herein, a range of about 50 microgram/kg/body weight to about 50 milligram/kg/body weight, or from about 50 microgram/kg/body weight to about 50 milligram/kg/body weight, etc., can be administered.

Route of Administration

In accordance with the methods of the present disclosure, the described halogenated stilbene analogs of the present disclosure or a pharmaceutically acceptable salt, solvate, hydrate or prodrug thereof, may be administered to a subject in a variety of forms depending on the selected route of administration, as will be understood by those skilled in the art. The active compound of the disclosure may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, intratumoral, transepithelial, nasal, intrapulmonary, intrathecal, rectal and topical modes of administration. Parenteral administration may be by continuous infusion over a selected period of time Alternatively, the compounds of this disclosure may be incorporated into formulations for any route of administration including for example, oral, topical and parenteral including intravenous, intramuscular, eye or ocular, intraperitoneal, intrabuccal, transdermal and in suppository form.

Methods of Treatment

In an embodiment, the present disclosure is directed to methods for treating a disorder associated with MAT2A biological activity in a subject comprising administering to the subject an effective amount of a compound or composition of one or more compounds of formula (I), formula (II) and/or formula (III) and/or one or more pharmaceutically acceptable salt, solvate, hydrate, prodrug or metabolite thereof.

In one embodiment, a MAT2A associated disorder is tumors and/or cancer. Therefore, in an embodiment, the present disclosure is also directed to methods for the treatment of tumors and/or cancer comprising administering an effective amount of one or more halogenated stilbene analogs of the present disclosure and/or a pharmaceutically acceptable salt, solvate, hydrate, prodrug or metabolite thereof to a patient in need of such therapy. For example, the present disclosure contemplates methods of treating various cancers and complications thereof. More particularly, the present disclosure relates to methods for inhibiting the growth of benign and malignant cancer, including a malignant tumor or cancer comprising exposing the tumor to an inhibitory or therapeutically effective amount or concentration of at least one of the halogenated stilbene analogs or pharmaceutically acceptable salts or pharmaceutically acceptable composition thereof. Treatment of internal malignancies such as eye or ocular cancer, rectal cancer, colon cancer, cervical cancer, prostate cancer, breast cancer, liver cancer and bladder cancer, and age-related cancer among numerous others are contemplated by the present disclosure.

Accordingly, the compounds and/or compositions of the present disclosure are useful for treating animals, and in particular, mammals, including humans, as patients. Thus, humans and other animals, and in particular, mammals, suffering from hyperproliferative disorders, and in particular, cancer, or other diseases as disclosed herein, can be treated by administering to the patient an effective amount of one or more of the halogenated stilbene analogs according to the present disclosure, or its derivative or a pharmaceutically acceptable salt thereof, optionally in a pharmaceutically acceptable carrier or diluent, either alone, or in combination with other known pharmaceutical agents (depending upon the disease to be treated). Treatment according to the present disclosure can also be by administration of the compounds and/or compositions of the present disclosure in conjunction with other conventional cancer therapies, such as radiation treatment or surgery or administration of other anti-cancer agents.

In certain embodiments, the present disclosure can find application in the treatment of any disease for which delivery of a therapeutic halogenated stilbene analog or a pharmaceutically acceptable salt, solvate, hydrate, prodrug or metabolite thereof to a cell or tissue of a subject is believed to be of therapeutic benefit. Examples of such diseases include hyperproliferative diseases and quiescent malignant diseases. In particular embodiments, the disease is a hyperproliferative disease, such as cancer of solid tissues or blood cells. Quiescent malignant diseases that can be treated by a halogenated stilbene analog of the present disclosure or a pharmaceutically acceptable salt, solvate, hydrate, prodrug or metabolite thereof include, for example, chronic lymphocytic leukemia.

For example, a compound or composition of a halogenated stilbene analog of the present disclosure or a pharmaceutically acceptable salt, solvate, hydrate, prodrug or metabolite thereof can be administered to treat a hyperproliferative disease. The hyperproliferative disease may be cancer, leiomyomas, adenomas, lipomas, hemangiomas, fibromas, pre-neoplastic lesions (such as adenomatous hyperplasia and prostatic intraepithelial neoplasia), carcinoma in situ, oral hairy leukoplakia, or psoriasis.

The cancer may be a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. In certain embodiments, the cancer is ovarian cancer. In particular aspects, the cancer may be a chemo-resistant cancer, i.e., refractive forms of cancer.

Diseases other than cancer involving altered physiological status are also encompassed by the present disclosure. For example, it has been shown that diabetes involves underlying signaling changes, namely resistance to insulin and failure to activate downstream signaling through IRS (Burks D J, White M F. Diabetes 2001 February; 50 Suppl 1:S140-5). Similarly, cardiovascular disease has been shown to involve hypertrophy of the cardiac cells involving multiple pathways such as the PKC family (Malhotra A. Mol Cell Biochem 2001 September; 225 (1-):97-107). Inflammatory diseases, such as rheumatoid arthritis, are known to involve the chemokine receptors and disrupted downstream signaling (D'Ambrosio D J Immunol Methods 2003 February; 273 (1-2):3-13).

In another aspect of the disclosure, there is provided a method for disrupting Wnt signaling in a cell by contacting the cell with an effective amount of a halogenated stilbene analog of the disclosure. The Wnt signaling pathway describes a complex network of proteins most well known for their roles in embryogenesis and cancer, but also involved in normal physiological processes in adult animals. The canonical Wnt pathway involves a series of events that occur when Wnt proteins bind to cell-surface receptors of the Frizzled family, causing the receptors to activate Dishevelled family proteins and ultimately resulting in a change in the amount of β-catenin that reaches the nucleus. Dishevelled (DSH) is a key component of a membrane-associated Wnt receptor complex which, when activated by Wnt binding, inhibits a second complex of proteins that includes axin, GSK-3, and the protein APC. The axin/GSK-3/APC complex normally promotes the proteolytic degradation of the .beta-catenin intracellular signaling molecule. After this β-catenin destruction complex is inhibited, a pool of cytoplasmic β-catenin stabilizes, and some β-catenin is able to enter the nucleus and interact with TCF/LEF family transcription factors to promote specific gene expression. In this aspect of the disclosure, cells are brought into contact with an amount of one or more compounds of the disclosure sufficient to disrupt Wnt signaling in the cells.

Combination Therapy

The active compounds of the present disclosure, i.e., one or more compounds of formula (I), formula (II) and/or formula (III) and/or one or more pharmaceutically acceptable salt, solvate, hydrate, prodrug or metabolite thereof can also be mixed with other active materials that do not impair the desired action, or with materials that supplement the desired action, such as other anticancer agents, and in certain instances depending upon the desired therapy or target, antibiotics, antifungals, antinflammatories, antiviral compounds or other agents having a distinct pharmacological effect.

The methods and compositions of the present disclosure further provide combination therapies which can enhance the therapeutic or protective effect of the compounds of the present disclosure, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with, for example, a therapeutic nucleic acid, such as a chemotherapeutic agent or an inhibitor of gene expression, as a second therapy. A tissue, tumor, or cell can be contacted with the compounds or compositions of the present disclosure and one or more additional anti-cancer treatment. For example, an additional anticancer treatment may include a chemotherapeutic agent, an anti-hormonal agent, radiotherapy, surgical therapy, or immunotherapy.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-1 1); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristine, vinblastine and methotrexate and pharmaceutically acceptable salts, acids or derivatives of any of the above.

Also included in the formulations may be anti-hormonal agents that act to regulate or inhibit hormone action on tumors such as anti-estrogens and selective estrogen receptor modulators (SERMs), including, for example, tamoxifen, raloxifene, droloxifene, A-hydroxytamoxifen, trioxifene, keoxifene, LY1 17018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analogue); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

In an embodiment, a therapeutic formulation or composition set forth herein, which comprises one or more compounds of formula (I), formula (II) and/or formula (III) and/or one or more pharmaceutically acceptable salt, solvate, hydrate, prodrug or metabolite thereof, may be administered before, during, after or in various combinations relative to a second anti-cancer treatment. The administrations may be in intervals ranging from concurrently to minutes to days to weeks. In embodiments where the halogenated stilbene containing composition is provided to a patient separately from an additional anti-cancer agent, one would generally ensure that a significant period of time did not expire between the time of each delivery, such that the two agents would still be able to exert an advantageously combined effect on the patient. In such instances, it is contemplated that one may provide a patient with the inhibitor of gene expression therapy and the anti-cancer therapy within about 12 to 24 or 72 h of each other and, more preferably, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

Within a single day (24-hour period), the patient may be given one or multiple administrations of the agent(s). Moreover, after a course of treatment, it is contemplated that there is a period of time at which no anti-cancer treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Administration of any compound or therapy of the present disclosure to a patient will follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary. It also is contemplated that various standard therapies, as well as radiation and surgical intervention, may be applied in combination with the described therapy.

In specific aspects, it is contemplated that a standard therapy will include chemotherapy, radiotherapy, immunotherapy, surgical therapy or gene therapy and may be employed in combination with the combination therapy described herein.

Articles of Manufacture

In another embodiment of the disclosure, an article of manufacture, or "kit", containing materials useful for the treatment of the diseases and disorders described above is provided. In one embodiment, the kit comprises a container comprising at least one compound of formula (I)-(III), and/or one or more pharmaceutically acceptable salt, solvate, hydrate, prodrug or metabolite thereof.

The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula (I)-(III) or a formulation thereof which is effective for treating the condition and may have a sterile access port (for example, the container may be an intravenous solution bag or a vial having a stopper pierceable by a hypodermic injection needle). At least one active agent in the composition is a compound of formula (I)-(III). The label or package insert indicates that the composition is used for treating the condition of choice, such as cancer.

In an embodiment, the kit includes two separate pharmaceutical compositions: one containing a compound of the present disclosure, and a second pharmaceutical compound. In another embodiment, an assay or diagnostic kit includes a labeled compound of the present disclosure and one or more reagents necessary for detecting the labeled compound upon binding to its target in-vivo or in-vitro. In a related embodiment, the kit includes a package insert that describes the steps necessary for carrying out the detection assay.

In another embodiment, a kit of the disclosure further comprises a needle or syringe, preferably packaged in sterile form, for injecting the composition, and/or a packaged alcohol pad. Instructions are optionally included for administration of halogenated stilbene compounds by a clinician or by the patient.

Diagnostic Methods and Diagnostic Probes

Another aspect of the present disclosure provides compounds having general formulas (I)-(III) with a linker moiety (hydrophobic linkers, hydrophilic linkers, photo-cleaveable linkers, redox reaction-cleaveable linkers), wherein the linker moiety is covalently bonded to a label molecule (a label could be a fluorophor, biotin, different polymer beads and different reactive groups). Exemplary biotinylated analogs have been depicted in FIG. 4 and synthesized according to Example 3, below.

The compounds of the present disclosure when biotinylated provide suitable means for non-radioactive detection and quantitation of MAT2A from complex samples, which offer a useful alternative approach to the routinely used radiometric assays. Therefore, another aspect of the present disclosure relates to the use of biotinylated stilbene analogs as a diagnostic reagent for detecting or monitoring the presence or levels MAT2A in a complex protein sample. A complex protein sample contains multiple proteins, and may additionally contain other contaminants. Non-limiting examples of a complex protein sample include tumor tissues, biopsy, serum and cell extracts.

In one embodiment, the present disclosure relates to a method of detecting, monitoring or analyzing the levels of MAT2A in a complex protein sample, said method comprising adding a labeled compound of formula (I)-(III) to said complex protein mixture under conditions whereby said labeled compound covalently conjugates to MAT2A; isolating the conjugated MAT2A by a suitable affinity-based separation method, removing unbound proteins, detecting the level of MAT2A following the separation. In a related embodiment, the detection can be accomplished by measuring a fluorescence signal emitted from the compound of formula (I)-(III). In another related embodiment, the detection can be accomplished by measuring a fluorescence signal emitted from a label bound via a linker to the compound of formula (1)-(III). The detection step can also be accomplished using various analytical procedures that known to the artisan for separating and analyzing complex protein mixtures. These analytical procedures include chromatographic methods such as HPLC, FPLC, ion exchange, size exclusion, mass spectrometry, and the like.

Figure 4:
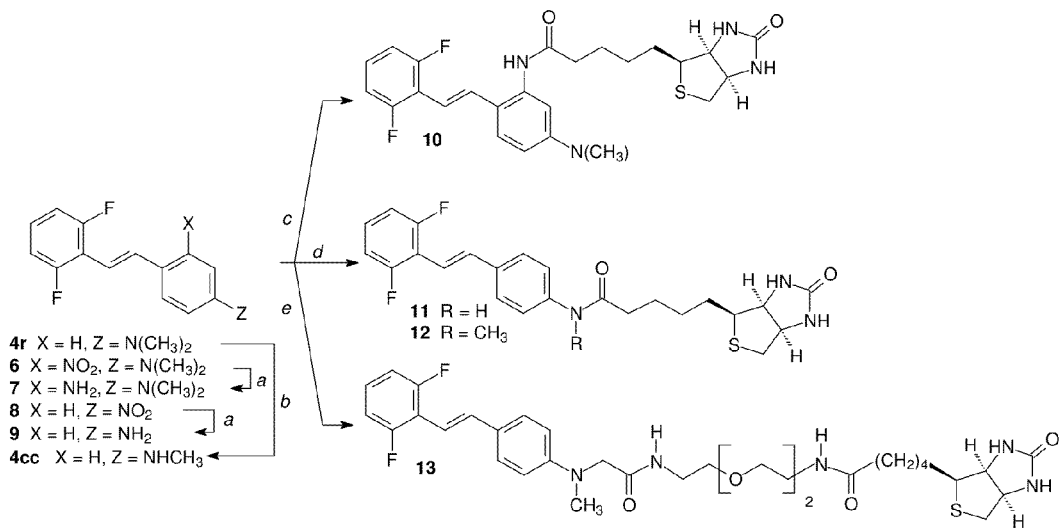
FIG. 4 is a schematic drawing of the synthesis of biotin derivatives of the halogenated stilbene analogs. Legend: a, $SnCl_2$, HCl, HOAc; b, CNBr; c, biotinyl chloride, $Et_3N$, THF; d, biotin, HOBt, EDC, $Et_3N$, DMF; e, (+)-biotinyl-iodoacetamidyl-3,6-dioxaoctanediamine, $K_2CO_3$, EtOH.
Figure 5:
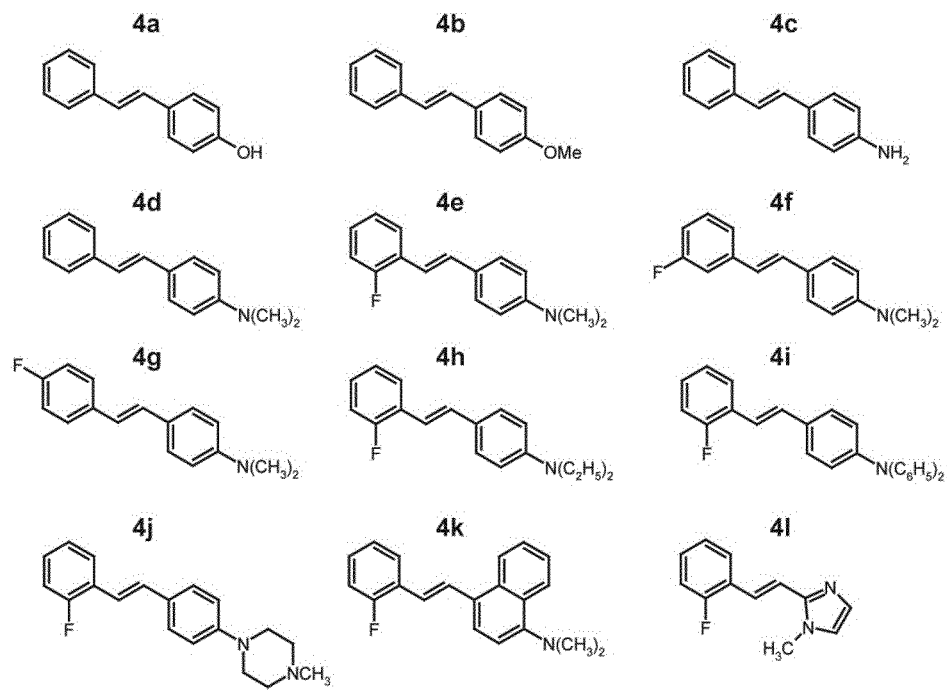
FIG. 5(A) provides the chemical structures of various monofluorinated stilbenes of the present disclosure.
FIG. 5(B) is a Western blot showing 4-aminostilbene (4c) represses Wnt target genes at 30 µM.
FIG. 5(C) is a Western blot showing 4-styryl-N,N-dimethylaniline (4d) is more active than 4-methoxystilbene (4b) at 30 µM.
FIG. 5(D) is a Western blot showing 4-(2-fluorostyryl)-N,N-dimethylaniline (4e) and 4-(3-fluorostyryl)-N,N-dimethylaniline (40 represses Wnt target genes at 10 µM.
FIG. 5(E) is a Western blot showing the effect of the dimethylaminophenyl group within 4e.
FIG. 5(F) is a graph showing the potency of (4e) in comparison to that of resveratrol and pterostilbene in inhibiting the proliferation of CRC cells.
Figure 5:
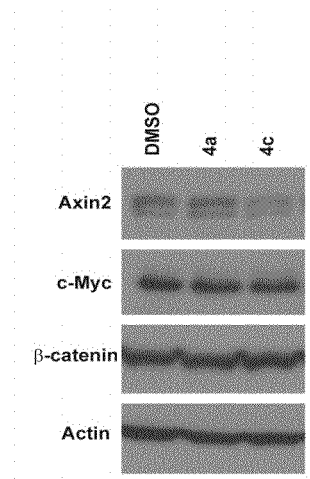
Figure 5:
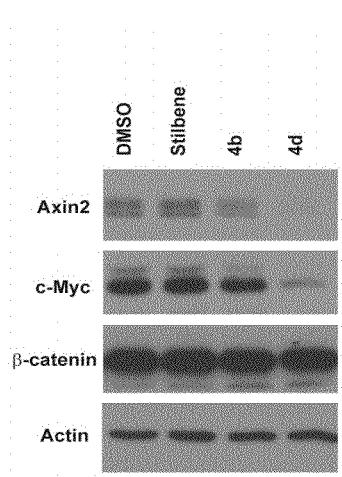
Figure 5:
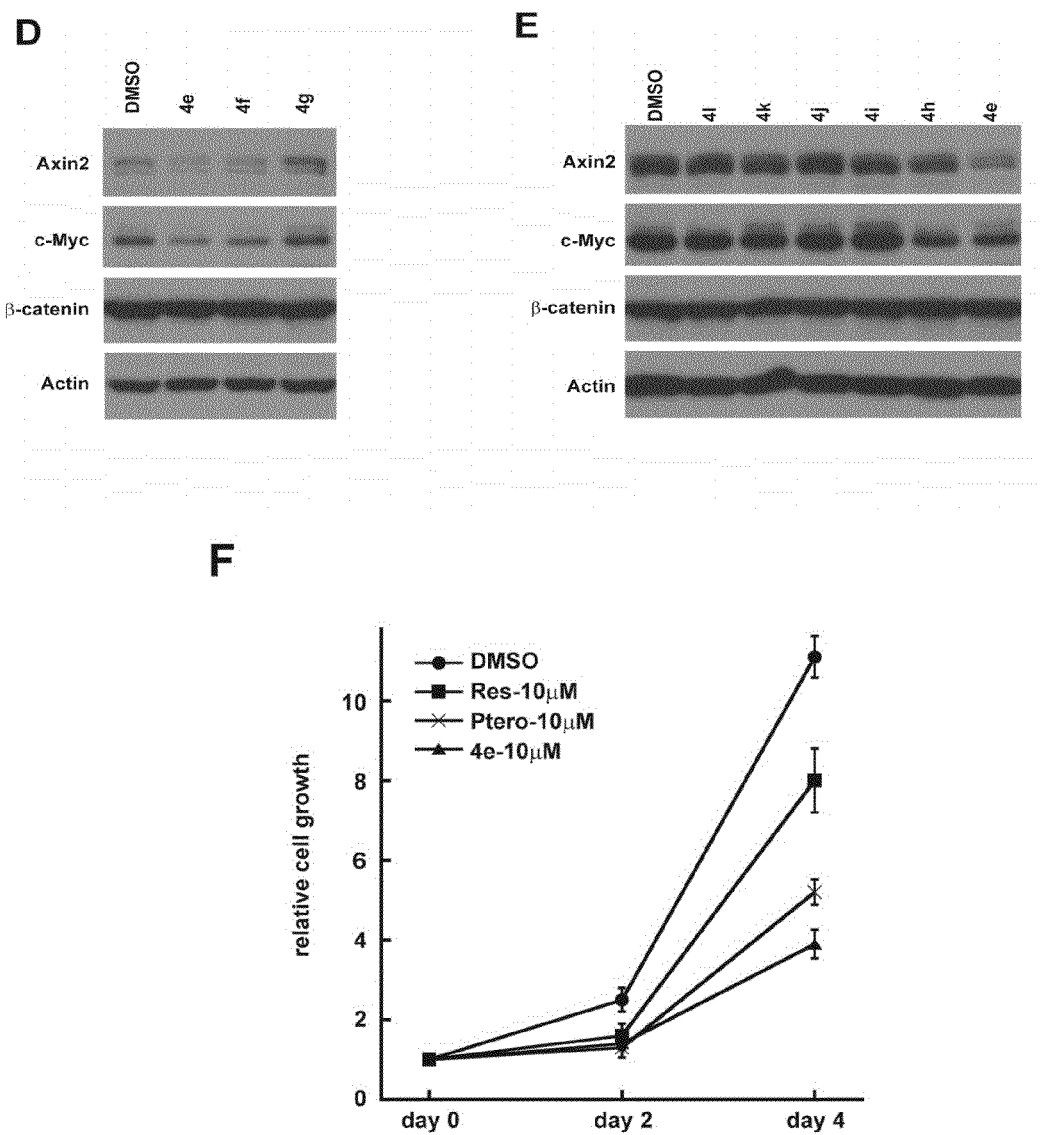

The linker moiety that can be used to attach a detectable label to the compounds of the present disclosure can be any of the linkers shown in FIG. 4. Alternatively, the linker moiety can a linker moiety comprising a repeating alkyleneoxy structure (polyethylene glycols, or "PEG"). Thus, one of skill in the art can select the linker moiety of the compounds of the present disclosure in order to provide additional specificity of them for MAT2A.

Linker moieties include among others, ethers, polyethers, diamines, ether diamines, polyether diamines, amides, polyamides, polythioethers, disulfides, silyl ethers, alkyl or alkenyl chains (straight chain or branched and portions of which may be cyclic) aryl, diaryl or alkyl-aryl groups, having from 0 to 3 sites of aliphatic unsaturation. While normally amino acids and oligopeptides are not preferred, when used they will normally employ amino acids of from 2-3 carbon atoms, i.e. glycine and alanine. Aryl groups in linker moieties can contain one or more heteroatoms (e.g., N, O or S atoms). The number of atoms referred to above are exclusive of hydrogen in referring to the number of atoms in a group, unless indicated otherwise. The linker moieties, when other than a bond, will have from about 1 to 60 atoms, usually 1 to 30 atoms, where the atoms include C, N, O, S, P, etc., particularly C, N and O, and will generally have from about 1 to 12 carbon atoms and from about 0 to 8, usually 0 to 6 heteroatoms.

In an embodiment, it is desirable to have a detectable label associated with a compound of the present disclosure to allow the compound-MAT2A complex to be captured and washed free of other components of the reaction mixture. The label will generally be under about 1 kDa. Biotin is a conventional label or ligand, particularly analogs such as dethiobiotin and deiminobiotin, which can be readily displaced from streptavidin by biotin. However, any small molecule will suffice that can be captured and released under convenient conditions.

Affinity purification of biological molecules, for example proteins, is known in the art and allows the purification of molecules by exploiting the binding affinity of the target molecule for a molecular binding partner. Examples of affinity purification methods are fusion tag protein purification, avidin-biotin system, pull-down assay and the like.

In another embodiment, the present disclosure relates to a method of diagnosing cancer in a subject, comprising: (1) contacting a labeled compound of formula (I)-(III) with protein in a complex protein sample obtained from the patient to bind the compound to and detect MAT2A protein in the sample; and (2) comparing the level of MAT2A in the sample to that in a normal reference sample, whereupon if the level of MAT2A in the sample is statistically higher than that in the normal reference sample, a diagnosis of cancer is indicated. In a related embodiment, the sample is a biopsy sample containing, for example, cancer cells selected from breast, prostate, colorectal, lung, colon, bladder, head and neck, intestine, ovarian, or skin cancer cells.

In another embodiment, the present disclosure relates to a method of identifying a subject who is a candidate for receiving treatment with the compounds of the present disclosure; such method comprises (1) obtaining a protein sample from the subject, (2) contacting a detectably labeled compound of formula (I)-(III) with protein present in a complex protein sample to bind to and detect MAT2A in said sample; and (3) comparing the level of MAT2A in the sample to that present in a normal reference sample, whereupon if the level of MAT2A in the sample is statistically higher than that in the normal reference, the subject's candidacy for treatment with one or more compounds of the present disclosure is indicated. In a related embodiment, the protein sample is a biopsy sample, tissue sample, serum sample, urine sample and the like. If necessary, conventional tools such as protein isolation kits can be used to obtain protein samples from raw biopsy, tissue, blood or urine samples. In another related embodiment, the labeled compound is a biotinylated compound of formula (I)-(III).

EXAMPLES

The following examples are intended to further illustrate certain preferred embodiments of the disclosure and are not limiting in nature. Those skilled in the art will recognize, or be able to ascertain, using no more than routine experimentation, numerous equivalents to the specific substances and procedures described herein.

Example 1

Synthesis of Stilbene Analogs

Materials and Methods:

Chemicals were purchased from Sigma Aldrich, MP Biomedical (4c) or TCI (4d) or were synthesized according to literature procedures. Solvents were used from commercial vendors without further purification unless otherwise noted. Nuclear magnetic resonance spectra were determined using a Varian instrument (1H, 400 MHz; 13C, 100 MHz unless otherwise noted). LRMS electron-impact (EI) ionization mass spectra were recorded at 70 eV on a ThermoFinnigan PolarisQ (ion trap mass spectrometer). Samples were introduced via a heatable direct probe inlet. High resolution electron impact (EI) ionization mass spectra were recorded at 25 eV on a JEOL JMS-700T MStation (magnetic sector instrument) at a resolution of greater than 10,000. Samples were introduced via heatable direct probe inlet. Perfluorokerosene (pfk) was used to produce reference masses. MALDI mass spectra were obtained on a Bruker Utraflexstreme time-of-flight mass spectrometer (Billerica, Mass.), using DHB (2,5-dihydroxybenzoic acid) matrix. Purity of compounds was >95% as established by combustion analyses. Elemental analyses were determined by Atlantic Microlabs, Inc., Norcross, Ga. Compounds were chromatographed on preparative layer Merck silica gel F254 unless otherwise indicated.

General Procedure A.

To 1.5 mmol of triphenylphosphonium bromide suspended in 4 mL of anhydrous THF at −78° C. was added 2.25 mmol (1.5 eq) of n-BuLi (1.6M in hexane). See FIG. 2 for a general schematic diagram of this reaction. The mixture was allowed to warm to 25° C. for 30 min, and 2.25 mmol of an aldehyde in 1 mL of anhydrous THF was added. The mixture was stirred for 24 h, diluted with $CH_2Cl_2$, washed with saturated $NH_4Cl$ solution, and dried over anhydrous $MgSO_4$. The product was purified by chromatography and/or recrystallization as noted for individual stilbenes listed below.

General Procedure B.

To a solution of 1.5 mmol of diethyl phosphonate in 4 mL of anhydrous DMF at 0° C. was added 2.25 mmol (1.5 eq) of NaH (washed with hexanes to remove oil). See FIG. 2 for a general schematic diagram of this reaction. The mixture was stirred for 20 min, and 1.5 mmol of an aldehyde in 1 mL of anhydrous DMF was added dropwise. The mixture was stirred 24 h at 25° C., quenched with ice, extracted with $CH_2Cl_2$, and dried over anhydrous $MgSO_4$. The product was purified by chromatography and/or recrystallization as noted for individual stilbenes listed below.

Synthesis of (E)-4-Hydroxystilbene (4a)

To 210 mg (1 mmol) of (E)-4-methoxystilbene (4b) in 7 mL of $CH_2Cl_2$ was added 1.28 mL of 1M $BBr_3$ (1.3 mmol) in dichloromethane at −10° C. The mixture was stirred for 4 h at −5° C. and quenched by pouring into cold water. The product was extracted with $CH_2Cl_2$, dried over anhydrous $MgSO_4$ and chromatographed using 1:10 $CH_3OH:CH_2Cl_2$ to afford 85 mg (43%) of 4a. mp 184-185° C.

Synthesis of (E)-4-Methoxystilbene (4b)

Procedure B. Yield 87%. Colorless crystals: mp 136-137° C.

Synthesis of (E)-4-(2-Fluorostyryl)-N,N-dimethylaniline (4e)

Procedure B. Yield 84%. Light yellow crystals from acetonitrile. mp 124-126° C. $^1$H NMR (acetone-$d_6$): δ 7.73-7.68 (m, 1H), 7.46 (d, 2H, J=8.8 Hz), 7.26-7.09 (m, 4H), 7.08 (d, 1H, J=16.8 Hz), 6.75 (d, 2H, J=9.2 Hz), 2.98 (s, 6H). $^{13}$C NMR (acetone-$d_6$): δ 160.18 (d, J=245.9 Hz), 150.85, 131.67 (d, J=4.6 Hz), 128.08 (d, J=8.4 Hz), 127.93 (two C), 126.8 (d, J=4.5 Hz), 126.14 (d, J=12.1 Hz), 125.46, 124.59 (d, J=3.1 Hz), 115.64 (d, J=22.0 Hz), 115.49 (d, J=4.6 Hz), 112.44 (two C), 39.69 (two C). MS: m/z (%) 241 (100), 240 (74), 225 (32), 197 (20), 196 (20), 177 (18), 176 (13). Anal. Calcd for $C_{16}H_{16}FN$: C, 79.64; H, 6.68. Found: C, 79.77; H, 6.80.

Synthesis of (E)-4-(3-Fluorostyryl)-N,N-dimethylaniline (4f)

Procedure B. Yield 65%. Light yellow crystals from acetonitrile. mp 147-148° C. $^1$H NMR (acetone-$d_6$): δ 7.42 (d, 2H, J=8.4 Hz), 7.35-7.25 (m, 3H), 7.17 (d, 1H, J=16.4 Hz), 6.96 (d, 1H, J=16.8 Hz), 6.93-6.88 (m, 1H), 6.72 (d, 2H, J=8.8 Hz), 2.95 (s, 6H). $^{13}$C NMR (acetone-$d_6$): δ 163.47 (d, J=241.4 Hz), 150.82, 141.36 (d, J=7.6 Hz), 130.66, 130.42 (d, J=8.4 Hz), 127.97 (two C), 125.22, 122.63 (d, J=2.2 Hz), 122.24 (d, J=2.2 Hz), 113.12 (d, J=21.3 Hz), 112.43 (two C), 111.96 (d, J=22.0 Hz), 39.69 (two C). MS: m/z (%) 241 (100), 240 (69), 225 (25), 197 (20), 196 (18), 177 (16), 176 (10). Anal. Calcd for $C_{16}H_{16}FN$: C, 79.64; H, 6.68. Found: C, 79.86; H, 6.67.

Synthesis of (E)-4-(4-Fluorostyryl)-N,N-dimethylaniline (4g)

Procedure B. Yield 64%. Light yellow crystals from acetonitrile. mp 197-198° C. Anal. Calcd for $C_{16}H_{16}FN$: C, 79.64; H, 6.68. Found: C, 79.85; H, 6.64.

Synthesis of (E)-4-(2-Fluorostyryl)-N,N-diethylaniline (4h)

Procedure B. Yield 51%. Light yellow crystals from hexane. mp 78-79° C. $^1$H NMR (acetone-$d_6$): δ 7.69-7.65 (m, 1H), 7.40 (d, 2H, J=8.8 Hz), 7.24-7.08 (m, 4H), 7.04 (d, 1H, J=16.4 Hz), 6.71 (d, 2H, J=8.8 Hz), 3.42 (q, 4H, J=7.2 Hz), 1.16 (t, 6H, J=7.2 Hz). $^{13}$C NMR (acetone-$d_6$): δ 160.13 (d, J=242.2 Hz), 148.04, 131.73 (d, J=4.5 Hz), 128.24 (two C), 127.91 (d, J=7.6 Hz), 126.70 (d, J=4.5 Hz), 126.27 (d, J=11.4 Hz), 124.57 (d, J=3.8 Hz), 124.49, 115.62 (d, J=22.0 Hz), 114.82 (d, J=3.8 Hz), 111.76 (two C), 44.19 (two C), 12.21 (two C). MS: m/z (%) 269 (34), 255 (19), 254 (100), 226 (22), 225 (20), 197 (16), 196 (17). Anal. Calcd for $C_{18}H_{20}FN$: C, 80.26; H, 7.48. Found: C, 80.07; H, 7.61.

Synthesis of (E)-4-(2-Fluorostyryl)-N,N-diphenylaniline (4i)

Procedure B. Yield 60%. Light yellow crystals from hexane. mp 114-115° C. $^1$H NMR (acetone-$d_6$): δ 7.77-7.73 (m, 1H), 7.54 (d, 2H, J=8.4 Hz), 7.34-7.06 (m, 15H), 7.02 (d, 2H, J=8.8 Hz). $^{13}$C NMR (acetone-d$_6$): δ 160.39 (d, J=245.9 Hz), 148.00, 147.73, 131.58, 130.87 (d, J=4.5 Hz), 129.63, 128.90 (d, J=8.3 Hz), 127.88, 127.23 (d, J=3.8 Hz), 125.58 (d, J=12.0 Hz), 124.75, 124.71, 123.53, 123.25, 118.78 (d, J=3.8 Hz), 115.76 (d, J=22.0 Hz). MS: m/z (%) 365 (100), 364 (12), 254 (13). Anal. Calcd for C$_{26}$H$_{20}$FN: C, 85.45; H, 5.52. Found: C, 85.59; H, 5.69.

Synthesis of (E)-1-(4-(2-Fluorostyryl)phenyl)-4-methylpiperazine (4j)

Procedure B. Yield 65%. Light yellow crystals from acetonitrile. mp 142-144° C. $^1$H NMR (acetone-d$_6$): δ 7.72-7.69 (m, 1H), 7.48 (d, 2H, J=8.8 Hz), 7.28-7.09 (m, 5H), 6.96 (d, 2H, J=8.8 Hz), 3.22 (t, 4H, J=5.2 Hz), 2.48 (t, 4H, J=5.2 Hz), 2.54 (s, 3H). $^{13}$C NMR (acetone-d$_6$): δ 160.27 (d, J=245.2 Hz), 151.59, 131.34 (d, J=5.3 Hz), 128.42 (d, J=8.4 Hz), 127.97, 127.81 (two C), 126.98 (d, J=3.8 Hz), 125.90 (d, J=12.1 Hz), 126.62 (d, J=3.8 Hz), 116.85 (d, J=3.8 Hz), 115.69 (d, J=22.0 Hz), 115.46 (two C), 55.09 (two C), 48.34 (two C), 45.70. MS: m/z (%) 296 (100), 281 (42), 226 (24), 211 (46), 197 (28), 196 (42), 177 (28). Anal. Calcd for C$_{19}$H$_{21}$FN$_2$: C, 77.00; H, 7.14. Found: C, 77.22; H, 7.49.

Synthesis of (E)-4-(2-Fluorostyryl)-N,N-dimethyl-naphthalen-1-amine (4k)

Procedure B. Yield 18%. Yellow crystals from hexane: Et$_2$O. mp 56-58° C. $^1$H NMR (acetone-d$_6$): δ 8.33-8.27 (m, 2H), 8.09 (d, 1H, J=16.4 Hz), 7.95-7.91 (m, 1H), 7.80 (d' 1H' J=8.0 Hz), 7.58-7.52 (m, 2H), 7.36-7.15 (m, 4H), 7.28 (d, 1H, J=16.4 Hz), 2.90 (s, 6H). $^{13}$C NMRm (acetone-d$_6$): δ 160.49 (d, J=246.7 Hz), 151.66, 132.85, 129.41, 129.10 (d, J=8.4 Hz), 128.92, 128.38 (d, J=4.6 Hz), 127.67 (d, J=3.8 Hz), 126.27, 125.78 (d, J=12.2 Hz), 125.17, 124.92, 124.74 (d, J=3.0 Hz), 124.25, 124.03, 121.75 (d, J=3.8 Hz), 115.78 (d, J=22.0 Hz), 114.19, 44.62. MS: m/z (%) 291 (100), 290 (28), 276 (70), 261 (40), 247 (22), 246 (15). Anal. Calcd for C$_{20}$H$_{18}$FN: C, 82.45; H, 6.23. Found: C, 82.42; H, 6.22.

Synthesis of (E)-2-(4-(2-Fluorostyryl)phenyl)-1-methyl-1H-imidazole (4l)

Procedure B. Yield 47%. Colorless crystals from hexane. mp 60-61° C. $^1$H NMR (acetone-d$_6$): δ 7.82-7.78 (m, 1H), 7.65 (d, 1H, J=16.0 Hz), 7.35-7.29 (m, 1H), 7.26 (d, 1H, J=16.0 Hz), 7.22-7.13 (m, 2H), 7.08 (d, 1H, J=1.2 Hz), 6.96 (d, 1H, J=0.8 Hz), 3.81 (s, 3H). $^{13}$C NMR (acetone-d$_6$): δ 160.65 (d, J=246.7 Hz), 145.39, 129.53 (d, J=8.3 Hz), 128.89, 127.66 (d, J=3.0 Hz), 124.98 (d, J=11.4 Hz), 124.71 (d, J=3.8 Hz), 122.73 (d, J=3.8 Hz), 122.18, 116.99 (d, J=5.3 Hz), 115.83 (d, J=22.0 Hz), 32.04. MS: m/z (%) 202 (17), 201 (59), 186 (20), 183 (100), 168 (25), 146 (16), 128 (17). Anal. Calcd for C$_{12}$H$_{11}$FN$_2$: C, 71.27; H, 5.48. Found: C, 71.24; H, 5.61.

Synthesis of (E)-4-(2,3-Difluorostyryl)-N,N-dimethylaniline (4m)

Procedure A. Yield 88%. Yellow crystals. mp 132-133° C. $^1$H NMR (acetone-d$_6$): δ 7.50-7.43 (m, 3H), 7.24 (d, 1H, J=16.4 Hz), 7.16-7.07 (m, 2H), 7.03 (d, 1H, J=16.4 Hz), 6.73 (d, 2H, J=8.8 Hz), 2.96 (s, 6H). $^{13}$C NMR (acetone-d$_6$): δ 151.09, 151.02 (dd, J$_1$=243.6 Hz, J$_2$=12.9 Hz), 147.87 (dd, J$_1$=246.3 Hz, J$_2$=12.9 Hz) 133.18 (d, J=5.3 Hz), 128.19 (two C), 124.95, 124.56 (dd, J$_1$=7.6 Hz, J$_2$=4.5 Hz, two C), 121.78 (t, J=3.0 Hz), 114.65 (d, J=17.4 Hz), 114.24 (d, J=3.8 Hz), 112.38 (two C), 39.64 (two C). MS: m/z (%) 259 (100), 258 (78), 243 (25), 214 (16), 195 (16). Anal. Calcd for C$_{16}$H$_{15}$F$_2$N: C, 74.11; H, 5.83. Found: C, 74.01; H, 5.71.

Synthesis of (E)-4-(2,4-Difluorostyryl)-N,N-dimethylaniline (4n)

Procedure B. Yield 58%. Yellow crystals from acetonitrile. mp 139-140° C. $^1$H NMR (acetone-d$_6$): δ 7.78-7.72 (m, 1H), 7.44 (d, 2H, J=8.4 Hz), 7.17 (d, 1H, J=16.4 Hz), 7.04-6.97 (m, 3H), 6.75 (d, 2H, J=9.2 Hz), 2.98 (s, 6H). $^{13}$C NMR (acetone-d$_6$): δ 161.65 (dd, J$_1$=245.2 Hz, J$_2$=12.1 Hz), 160.00 (dd, J$_1$=248.6 Hz, J$_2$=12.1 Hz) 150.87, 131.54 (dd, J$_1$=4.5 Hz, J$_2$=2.3 Hz), 127.89 (two C), 125.34, 122.84 (dd, J$_1$=12.1 Hz, J$_2$=3.8 Hz), 114.56 (t, J=1.6 Hz), 112.43 (two C), 111.73 (dd, J$_1$=21.3 Hz, J$_2$=3.8 Hz, two C), 103.85 (t, J=26.2 Hz), 39.68 (two C). MS: m/z (%) 259 (100), 258 (71), 243 (30), 215 (15), 195 (14). Anal. Calcd for C$_{16}$H$_{15}$F$_2$N: C, 74.11; H, 5.83. Found: C, 74.25; H, 5.77.

Synthesis of (E)-4-(2,5-Difluorostyryl)-N,N-dimethylaniline (4o)

Procedure A. Yield 77%. Yellow crystals. mp 146-147° C. $^1$H NMR (acetone-d$_6$): δ 7.51-7.46 (m, 3H), 7.28 (d, 1H, J=16.4 Hz), 7.18-7.12 (m, 1H), 7.03 (d, 1H, J=16.4 Hz), 7.00-6.95 (m, 1H), 6.76 (d, 2H, J=8.8 Hz), 2.99 (s, 6H). $^{13}$C NMR (acetone-d$_6$): δ 159.28 (dd, J=236.0 Hz), 156.22 (dd, J=241.4 Hz), 151.09, 133.04 (d, J=3.8 Hz), 128.21 (two C), 124.94, 116.97 (dd, J$_1$=25.5 Hz, J$_2$=9.6 Hz, two C), 114.08 (dd, J$_1$=24.7 Hz, J$_2$=8.7 Hz, two C), 112.38 (two C), 112.12 (d, J=4.5 Hz), 39.64 (two C). MS: m/z (%) 259 (100), 258 (84), 243 (29), 215 (18), 195 (17). Anal. Calcd for C$_{16}$H$_{15}$F$_2$N: C, 74.11; H, 5.83. Found: C, 74.63; H, 5.90.

Synthesis of (E)-2-(2,6-Difluorostyryl)-N,N-dimethylaniline (4p)

Procedure B. Yield 92%. Yellow oil. $^1$H NMR (acetone-d$_6$): δ 7.78 (d, 1H, J=16.8 Hz), 7.65 (dd, 1H, J$_1$=7.6 Hz, J$_2$=1.6 Hz), 7.36-7.26 (m, 2H), 7.12-7.03 (m, 5H), 2.74 (s, 6H). $^{13}$C NMR (acetone-d$_6$): δ 161.06 (dd, J$_1$=242.2 Hz, J$_2$=7.6 Hz, two C), 152.77, 133.81 (t, J=8.0 Hz), 131.25, 129.19, 128.59 (t, J=11.0 Hz), 126.72, 122.65, 118.46, 115.31 (t, J=15.6 Hz), 113.84, 111.92 (dd, J$_1$=19.4 Hz, J$_2$=6.8 Hz, two C), 44.31 (two C). MS: m/z (%) 259 (100), 258 (14), 132 (8). Anal. Calcd for C$_{16}$H$_{15}$F$_2$N: C, 74.11; H, 5.83. Found: C, 74.38; H, 5.79.

Synthesis of (E)-3-(2,6-Difluorostyryl)-N,N-dimethylaniline (4q)

Procedure B. Yield 53%. Colorless crystals from hexane. mp 69-71° C. $^1$H NMR (acetone-d$_6$): δ 7.38 (d, 1H, J=16.8 Hz), 7.33-7.26 (m, 1H), 7.21-7.18 (m, 1H), 7.11 (d, 1H, J=17.2 Hz), 7.07-7.00 (m, 2H), 6.93-6.91 (m, 2H), 6.72-6.69 (m, 1H), 2.96 (s, 6H). $^{13}$C NMR (acetone-d$_6$): δ 161.03 (dd, J$_1$=248.2 Hz, J$_2$=7.6 Hz, two C), 151.38, 138.03, 136.83 (t, J=8.0 Hz), 129.46, 128.70 (t, J=11.0 Hz), 114.87 (t, J=16.0 Hz), 114.81, 114.09, 112.98, 111.91 (dd, J$_1$=19.4 Hz, J$_2$=6.5 Hz, two C), 111.21, 39.93 (two C). MS: m/z (%) 259 (100), 258 (52), 239 (31), 238 (33), 223 (16), 222 (37). Anal. Calcd for C$_{16}$H$_{15}$F$_2$N: C, 74.11; H, 5.83. Found: C, 74.30; H, 5.78.

Synthesis of (E)-4-(2,6-Difluorostyryl)-N,N-dimethylaniline (4r)

Procedure B. Yield 94%. Pale yellow crystals from hexane. mp 112-113° C. $^1$H NMR (acetone-d$_6$): δ 7.45 (d, 2H, J=8.4

Hz), 7.35 (d, 1H, J=16.8 Hz), 7.27-7.20 (m, 1H), 7.01-6.98 (m, 2H), 6.91 (1H, d, J=16.8 Hz), 6.75 (d, 2H, J=9.2 Hz), 2.98 (s, 6H). $^{13}$C NMR (acetone-d$_6$): δ 160.82 (dd, J$_1$=247.9 Hz, J$_2$=8.0 Hz, two C), 151.10, 135.99 (t, J=8.3 Hz), 127.97 (two C), 127.57 (t, J=11.3 Hz), 125.41, 115.50 (t, J=16.0 Hz), 112.40 (two C), 111.79 (dd, J$_1$=19.0 Hz, J$_2$=6.8 Hz, two C), 109.73, 39.65 (two C). MS: m/z (%) 259 (100), 258 (71), 243 (25), 195 (11). Anal. Calcd for C$_{16}$H$_{15}$F$_2$N: C, 74.11; H, 5.83. Found: C, 74.08; H, 5.79.

Synthesis of (E)-4-(2,6-Difluorostyryl)-N,N-diethylaniline (4s)

Procedure B. Yield 57%. Yellow crystals from hexane. mp 70-71° C. $^1$H NMR (acetone-d$_6$): δ 7.43 (d, 2H, J=8.4 Hz), 7.34 (d, 1H, J=16.8 Hz), 7.27-7.20 (m, 1H), 7.01-6.98 (m, 2H), 6.89 (d, 1H, J=16.8 Hz), 6.72 (d, 2H, J=8.8 Hz), 3.43 (q, 4H, J=7.2 Hz), 1.16 (t, 6H, J=7.2 Hz). $^{13}$C NMR (acetone-d$_6$): δ 160.80 (dd, J$_1$=247.1 Hz, J$_2$=8.0 Hz, two C), 148.30, 136.07 (t, J=8.3 Hz), 128.29 (two C), 127.37 (t, J=10.6 Hz), 124.45, 115.62 (t, J=16.0 Hz), 111.78 (dd, J$_1$=19.0 Hz, J$_2$=6.8 Hz, two C), 111.73 (two C), 109.07, 44.20 (two C), 12.20 (two C). MS: m/z (%) 287 (44), 272 (100), 244 (21), 243 (15). Anal. Calcd for C$_{18}$H$_{19}$F$_2$N: C, 75.24; H, 6.66. Found: C, 75.12; H, 6.79.

Synthesis of (E)-4-(3,4-Difluorostyryl)-N,N-dimethylaniline (4t)

Procedure A. Yield 59%. Yellow crystals from hexane. mp 159-160° C. $^1$H NMR (acetone-d$_6$): δ 7.50-7.44 (m, 1H), 7.41 (d, 2H, J=8.8 Hz), 7.32-7.28 (m, 1H), 7.27-7.20 (m, 1H), 7.11 (d, 1H, J=16.0 Hz), 6.92 (d, 1H, J=16.4 Hz), 6.71 (d, 2H, J=8.8 Hz), 2.95 (s, 6H). $^{13}$C NMR (acetone-d$_6$): δ 150.82, 150.56 (dd, J$_1$=243.9 Hz, J$_2$=12.9 Hz), 148.99 (dd, J$_1$=244.3 Hz, J$_2$=12.9 Hz), 130.55 (d, J=3.0 Hz), 127.91 (two C), 125.16, 122.71 (d, J=6.1 Hz), 122.68 (d, J=6.1 Hz), 121.68 (d, J=2.3 Hz), 117.49 (d, J=17.4 Hz), 113.96 (d, J=17.5 Hz), 112.43 (two C), 39.68 (two C). MS: m/z (%) 259 (100), 258 (82), 243 (36), 215 (22), 195 (16). Anal. Calcd for C$_{16}$H$_{15}$F$_2$N: C, 74.11; H, 5.83. Found: C, 74.24; H, 5.79.

Synthesis of (E)-4-(3,5-Difluorostyryl)-N,N-dimethylaniline (4u)

Procedure A. Yield 51%. Yellow crystals. mp 136-137° C. Anal. Calcd for C$_{16}$H$_{15}$F$_2$N: C, 74.11; H, 5.83. Found: C, 74.38; H, 5.70.

Synthesis of (E)-N,N-Dimethyl-4-(2,3,6-trifluorostyryl)aniline (4v)

Procedure B. Yield 45%. Light yellow crystals from hexane. mp 91-92° C. $^1$H NMR (acetone-d$_6$): δ 7.48 (d, 2H, J=9.2 Hz), 7.39 (d, 1H, J=16.8 Hz), 7.22-7.14 (m, 1H), 7.06-7.00 (m, 1H), 6.89 (d, 1H, J=16.8 Hz), 6.76 (d, 2H, J=8.0 Hz), 3.00 (s, 6H). $^{13}$C NMR (acetone-d$_6$): δ 156.09 (ddd, J$_1$=243.9 Hz, J$_2$=5.3 Hz, J$_3$=2.4 Hz), 151.31, 147.94 (m, two C), 137.17 (t, J=8.4 Hz), 128.23 (two C), 124.89, 117.43 (dd, J$_1$=17.1 Hz, J$_2$=12.1 Hz), 114.02 (dd, J$_1$=19.4 Hz, J$_2$=10.2 Hz), 112.33 (two C), 111.21 (ddd, J$_1$=25.5 Hz, J$_2$=7.6 Hz, J$_3$=3.8 Hz), 108.99, 39.59 (two C). MS: m/z (%) 277 (100), 276 (83), 261 (24), 214 (16), 213 (12). Anal. Calcd for C$_{16}$H$_{14}$F$_3$N: C, 69.30; H, 5.09. Found: C, 69.50; H, 4.97.

Synthesis of (E)-N,N-Dimethyl-4-(2,4,6-trifluorostyryl)aniline (4w)

Procedure B. Yield 63%. Light yellow crystals from hexane. mp 127-128° C. $^1$H NMR (acetone-d$_6$): δ 7.45 (d, 2H, J=8.8 Hz), 7.29 (d, 1H, J=16.8 Hz), 6.91 (t, 2H, J=8.8 Hz), 6.83 (d, 1H, J=16.8 Hz), 6.75 (d, 2H, J=8.8 Hz), 2.99 (s, 6H). $^{13}$C NMR (acetone-d$_6$): δ 160.87 (m, three C), 151.09, 135.59 (m, two C), 127.95 (two C), 125.25, 112.39 (two C), 108.80, 100.65 (dd, J$_1$=30.7 Hz, J$_2$=25.8 Hz, two C), 39.64 (two C). MS: m/z (%) 277 (100), 276 (75), 261 (29). Anal. Calcd for C$_{16}$H$_{14}$F$_3$N: C, 69.30; H, 5.09. Found: C, 69.49; H, 4.99.

Synthesis of (E)-4-(2-chloro-6-fluorostyryl)-N,N-dimethylaniline (4x)

Procedure B. Yield 90%. Yellow crystals, crystals from hexane. mp 42-44° C. $^1$H NMR (DMSO-d$_6$): δ 7.43 (d, 2H, J=8.8 Hz), 7.36-7.33 (m, 1H), 7.27-7.13 (m, 3H), 6.94 (d, 1H, J=16.8 Hz), 6.73 (d, 2H, J=8.8 Hz), 2.95 (s, 6H). $^{13}$C NMR (DMSO-d$_6$): δ 160.74 (d, J=249.1 Hz), 151.02, 136.87 (d, J=12.1 Hz), 133.35 (d, J=6.1 Hz), 128.51 (d, J=10.1 Hz), 128.31 (two C), 126.28 (d, J=3.4 Hz), 124.72, 124.59 (d, J=14.8 Hz), 115.55 (d, J=23.5 Hz), 113.91 (d, J=2.1 Hz), 112.58 (two C), 40.30 (two C). MS: m/z (%) 277 (37), 276 (36), 275 (100), 274 (31), 225 (19). Anal. Calcd for C$_{16}$H$_{15}$ClFN: C, 69.69; H, 5.48. Found: C, 69.68; H, 5.61.

Synthesis of (E)-4-(2,6-dichlorostyryl)-N,N-dimethylaniline (4y)

Procedure B. Yield 78%. Yellow crystals from hexane. mp 96-97° C. $^1$H NMR (acetone-d$_6$): 7.48-7.44 (m, 4H), 7.25-7.21 (m, 1H), δ 7.11 (d, 1H, J=16.8 Hz), 6.94 (d, 1H, J=16.4 Hz), 6.77 (d, 2H, J=8.8 Hz), 2.99 (s, 6H). $^{13}$C NMR (acetone-d$_6$): δ 151.19, 137.63, 135.36, 134.18, 128.97 (two C), 128.18 (two C), 128.02 (two C), 124.79, 117.40, 112.41 (two C), 39.68 (two C). MS: m/z (%) 293 (65), 292 (32), 291 (100), 221 (40), 220 (30). Anal. Calcd for C$_{16}$H$_{15}$Cl$_2$N: C, 65.77; H, 5.17. Found: C, 65.52; H, 5.17.

Synthesis of (E)-4-(2,6-Difluorophenethyl)-N,N-dimethylaniline (5r)

To 150 mg (0.58 mmol) of 4r in 10 mL of THF was added 50 mg of 10% Pd—C. The mixture was hydrogenated at 40 psi on a Parr shaker for 5 h. The mixture was filtered through Celite and chromatographed using 1:10 EtOAc:hexane to afford 110 mg (76%) of 5r: Colorless crystals from hexane. mp 42-43° C. $^1$H NMR (acetone-d$_6$): δ 7.31-7.23 (m, 1H), 7.02 (d, 2H, J=8.4 Hz), 6.98-6.92 (m, 2H), 6.66 (d, 2H, J=8.4 Hz), 2.90-2.89 (m, 2H), 2.85 (s, 6H), 2.77-2.73 (m, 2H). $^{13}$C NMR (acetone-d$_6$): δ 161.68 (dd, J$_1$=244.1 Hz, J$_2$=8.7 Hz, two C), 149.62, 128.98, 128.94 (two C), 128.15 (t, J=10.3 Hz), 117.36 (t, J=20.5 Hz), 112.88 (two C), 111.22 (dd, J$_1$=19.4 Hz, J$_2$=7.2 Hz, two C), 40.10 (two C), 34.73, 24.75. MS: m/z (%) 261 (40), 134 (100), 118 (27), 91 (22). Anal. Calcd for C$_{16}$H$_{17}$F$_2$N: C, 73.54; H, 6.56. Found: C, 73.53; H, 6.49.

Example 2

Synthesis of Metabolites of Halogenated Stilbene Analogs

General Procedure:

To a stirred solution of 4 (0.7 mmol) in CHCl$_3$ (3 mL) was added 70% m-CPBA (0.7 mmol, 1 equiv), portionwise at 0° C. The resulting mixture was stirred at room temperature for 5 h. The mixture was diluted with CH$_2$Cl$_2$ (15 mL), washed with saturated NaHCO$_3$ solution and water, dried over anhy-

Synthesis of (E)-4-(2,6-difluorostyryl)-N,N-dimethylaniline oxide (4z)

Yield 72%. $R_f$=0.31 (1:5 CH$_3$OH—CH$_2$Cl$_2$). mp 100-103° C. $^1$H NMR (DMSO-d$_6$): δ 8.11 (d, 2H, J=8.4 Hz), 7.72 (d, 2H, J=8.8 Hz), 7.43-7.35 (m, 2H), 7.21-7.15 (m, 3H), 3.40 (s, 6H). $^{13}$C NMR (DMSO-d$_6$): δ 160.85 (dd, J$_1$=249.0 Hz, J$_2$=7.6 Hz, two C), 156.35, 137.30, 134.60 (t, J=7.6 Hz), 130.13 (t, J=10.7 Hz), 127.42 (two C), 121.67 (two C), 116.40, 114.44 (t, J=15.2 Hz), 112.76 (dd, J$_1$=19.0 Hz, J$_2$=6.1 Hz, two C), 63.92 (two C). HRMS (EI) Calcd for C$_{16}$H$_{15}$F$_2$NO: 275.1121. Found: 275.1120.

Synthesis of (E)-4-(2-chloro-6-fluorostyryl)-N,N-dimethylaniline oxide (4aa)

Yield 54%. Yellow solid. $R_f$=0.34 (1:5 CH$_3$OH—CH$_2$Cl$_2$). mp 82-84° C. $^1$H NMR (acetone-d$_6$): δ 8.21 (d, 2H, J=8.8 Hz), 7.73 (d, 2H, J=8.8 Hz), 7.43 (d, 1H, J=16.4 Hz), 7.38-7.32 (m, 3H), 7.26-7.21 (m, 1H), 3.50 (s, 6H). $^{13}$C NMR (acetone-d$_6$): δ 161.29 (d, J=249.8 Hz), 156.41, 137.41, 135.20 (d, J=12.1 Hz), 134.40 (d, J=5.3 Hz), 129.41 (d, J=10.6 Hz), 126.98 (two C), 126.06 (d, J=3.0 Hz), 123.93 (d, J=14.4 Hz), 121.41 (two C), 120.31 (d, J=1.5 Hz), 115.19 (d, J=23.6 Hz), 63.27 (two C). HRMS (EI) Calcd for C$_{16}$H$_{15}$ClFNO: 291.0826. Found: 291.0828.

Synthesis of (E)-4-(2,6-dichlorostyryl)-N,N-dimethylaniline oxide (4bb)

Yield 80%. $R_f$=0.19 (1:10 CH$_3$OH—CH$_2$Cl$_2$). mp 80-82° C. $^1$H NMR (DMSO-d$_6$): δ 8.13 (d, 2H, J=9.2 Hz), 7.71 (d, 2H, J=9.2 Hz), 7.55 (d, 2H, J=8.4 Hz), 7.34 (t, 1H, J=8.0 Hz), 7.22 (d, 1H, J=16.8 Hz), 7.11 (d, 1H, J=16.8 Hz), 3.41 (s, 6H). $^{13}$C NMR (DMSO-d$_6$): δ 156.31, 136.52, 136.12, 134.51, 134.11, 129.97, 129.34 (two C), 127.24 (two C), 123.85 (two C), 121.49 (two C), 63.78 (two C). HRMS (EI) Calcd for C$_{16}$H$_{15}$Cl$_2$NO: 307.0531. Found: 307.0530.

Synthesis of (E)-4-(2,6-Difluorostyryl)-N-methylaniline (4 cc)

A solution of 1 g (3.86 mmol) of 4r and 820 mg (7.72 mmol, 2 equiv) of cyanogen bromide in 15 mL of acetone was refluxed for 16 h. The mixture was cooled and concentrated under a stream of argon. The residue was triturated with ether, and the combined ethereal extracts were combined and concentrated. The product was refluxed with 25 mL of concentrated HCl for 3 h. The mixture was neutralized with 2M NaOH solution, extracted with ether, dried over anhydrous MgSO$_4$, and concentrated. The product was purified by chromatography using 1:5 EtOAc-hexane to afford 320 mg (34%) of 4 cc as a yellow solid: mp 51-52° C. $^1$H NMR (DMSO-d$_6$): δ 7.32 (d, 2H, J=8.8 Hz), 7.29-7.21 (m, 2H), 7.14-7.06 (m, 2H), 6.79 (d, 1H, J=16.4 Hz), 6.55 (d, 2H, J=8.8 Hz), 6.02 (q, 1H, J=5.2 Hz), 2.70 (d, 3H, J=5.2 Hz). $^{13}$C NMR (DMSO-d$_6$): δ 160.36 (dd, J$_1$=246.8 Hz, J$_2$=8.0 Hz, two C), 150.88, 136.35 (t, J=7.5 Hz), 128.42 (two C), 127.96 (d, J=10.7 Hz), 124.53, 115.32 (t, J=15.5 Hz), 112.33 (dd, J$_1$=19.1 Hz, J$_2$=6.8 Hz, two C), 112.09 (two C), 108.86, 29.93. MS: m/z (%) 246 (30), 245 (100), 244 (15). Anal. Calcd for C$_{15}$H$_{13}$F$_2$N: C, 73.45; H, 5.34. Found: C, 73.31; H, 5.26.

Synthesis of (E)-4-(2-chloro-6-fluorostyryl)-N-methylaniline (4dd)

The procedure used to prepare 4 cc was repeated using 1 g (3.63 mmol) of 4x and 764 mg (7.26 mmol, 2 equiv) of cyanogen bromide to afford a product that was purified by chromatography using 1:5 EtOAc-hexane to afford 400 mg (42%) of 4dd as a yellow solid: mp 43-45° C. $^1$H NMR (DMSO-d$_6$): δ 7.37-7.31 (m, 3H), 7.27-7.21 (m, 2H), 7.18 (d, 1H, J=16.4 Hz), 6.88 (d, 1H, J=16.4 Hz), 6.56 (d, 2H, J=8.8 Hz), 6.04 (q, 1H, J=5.2 Hz), 2.71 (d, 3H, J=5.2 Hz). $^{13}$C NMR (DMSO-d$_6$): δ 160.75 (d, J=248.0 Hz), 150.98, 137.24 (d, J=12.2 Hz), 133.30 (d, J=6.1 Hz), 128.49 (two C), 128.33 (d, J=9.9 Hz), 126.28 (d, J=3.1 Hz), 124.73 (d, J=14.5 Hz), 124.40, 115.54 (d, J=22.9 Hz), 113.12 (d, J=2.2 Hz), 112.11 (two C), 29.94. MS: m/z (%) 261 (100), 227 (15), 213 (25). Anal. Calcd for C$_{15}$H$_{13}$Cl FN: C, 68.84; H, 5.01. Found: C, 68.67; H, 5.05.

Synthesis of (E and Z)-4-(2,6-dichlorostyryl)-N-methylaniline (4ee)

The procedure used to prepare 4 cc was repeated using 1 g (3.42 mmol) of 4y and 720 mg (6.84 mmol, 2 equiv) of cyanogen bromide to afford a product that was purified by chromatography (multiple times and each time using two developments) using 1:5 EtOAc-hexane to afford 390 mg (41%) of 4ee as a 9:1 E:Z-mixture of isomers that was a yellow oil. $^1$H NMR (DMSO-d$_6$): δ 7.49 (d, 2H, J=8.4 Hz), 7.35 (d, 2H, J=8.4 Hz), 7.24 (t, 1H, J=8.0 Hz), 6.99 (d, 1H, J=16.4 Hz), 6.82 (d, 1H, J=16.4 Hz), 6.55 (d, 2H, J=8.4 Hz), 6.01 (q, 1H, J=5.2 Hz), 2.70 (d, 3H, J=5$_{0.2}$ H$_z$). $^{13}$C NMR (DMSO-d$_6$): δ 150.45, 137.40, 134.69, 133.36, 128.86 (two C), 128.28, 127.97 (two C), 123.47, 116.09 (two C), 111.57 (two C), 29.50. HRMS (EI) Calcd for C$_{15}$H$_{13}$Cl$_2$N: 277.0425. Found: 277.0425.

Synthesis of (E)-4-(2,6-difluorostyryl)-N,N,N-trimethylbenzenaminium iodide (4ff)

To a solution of 200 mg (0.77 mmol) of 4r in acetone (2 mL) was added CH$_3$I 328 mg (2.31 mmol, 3 equiv). The resulting mixture was refluxed for 8 h. The precipitate formed was collected by filtration, washed with ethyl ester, and the residual solvent was removed in vacuo to afford 200 mg (64%) of 4ff as a white solid: mp 198-199° C. $^1$H NMR (DMSO-d$_6$): δ 7.98 (d, 2H, J=8.8 Hz), 7.91 (d, 2H, J=9.2 Hz), 7.47-7.38 (m, 2H), 7.29 (d, 1H, J=16.8 Hz), 7.23-7.17 (m, 2H), 3.62 (s, 9H). $^{13}$C NMR (DMSO-d$_6$): δ 160.30 (dd, J$_1$=249.1 Hz, J$_2$=7.4 Hz, two C), 146.72, 138.44, 133.04 (t, J=7.8 Hz), 130.00 (t, J=10.8 Hz), 128.05 (two C), 121.03 (two C), 117.44, 113.58 (t, J=15.5 Hz), 112.23 (dd, J$_1$=19.2 Hz, J$_2$=5.7 Hz, two C), 56.45 (three C). Anal. Calcd for C$_{17}$H$_{18}$F$_2$I N: C, 50.89; H, 4.52. Found: C, 51.10; H, 4.49.

Example 3

Synthesis of Biotinylated Analogs of Halogenated Stilbenes

In this example, several biologically active biotin-labeled halogenated stilbene analogs, in particular fluorinated N,N-dialkylaminostilbenes (FIDAS or FIDAS agents), where prepared. As shown in FIG. 4, several Biotin-FIDAS compounds with variable spacers between the FIDAS agent and the biotin were prepared. It was established, through the synthesis of other amides lacking the biotin heterocycle or possessing biotin alone, that activity resides in the stilbene and not in the biotin portion of these molecules. The optimal spacer length between the two termini was determined, and the binding and eluting conditions for Biotin-FlDAS and streptavidin beads were established.

Synthesis of (E)-4-(2,6-Difluorostyryl)-N,N-dimethyl-3-nitroaniline (6)

To a solution of 1.63 g (6.18 mmol, 1.2 equiv) of diethyl 2,6-difluorobenzylphosphonate in 15 mL of anhydrous DMF at 0° C. was added 310 mg (7.72 mmol, 1.5 equiv) of 60% NaH. The mixture was stirred for 30 min, and a solution of 1.0 g (5.15 mmol) of 4-(dimethylamino)-3-nitrobenzaldehyde in 8 mL of anhydrous DMF was added over a 10 min period. The mixture was stirred for 2 h at 0° C. and poured into cold water. The precipitate was collected by filtration and recrystallized from acetonitrile to afford 1.1 g (70%) of 6 as red crystals: mp 152-153° C. $^1$H NMR (acetone-d$_6$): δ 7.81 (d, 1H, J=8.8 Hz), 7.68 (d, 1H, J=16.4 Hz), 7.38-7.30 (m, 1H), 7.17 (d, 1H, J=3.2 Hz), 7.10-7.03 (m, 3H), 7.01 (d, 1H, J=16.8 Hz), 3.1 (s, 6H). $^{13}$C NMR (acetone-d$_6$): δ 160.76 (dd, J$_1$=248.3 Hz, J$_2$=7.5 Hz, two C), 150.56, 150.03, 129.66 (t, J=8.7 Hz), 128.73 (t, J=10.7 Hz), 128.08, 118.20, 116.16, 114.92 (t, J=1.6 Hz), 114.52 (t, J=15.1 Hz), 111.74 (dd, J$_1$=19.7 Hz, J$_2$=6.5 Hz, two C), 106.01, 39.31 (two C). HRMS (EI) Calcd for C$_{16}$H$_{14}$F$_2$N$_2$O$_2$: 304.1023. Found: 304.1016.

Synthesis of (E)-4-(2,6-Difluorostyryl)-N$^1$,N$^1$-dimethylbenzene-1,3-diamine (7)

A solution of 5 g (26.4 mmol, 8.5 equiv) of SnCl$_2$ in 7 mL of conc HCl was added dropwise to a solution of 0.95 g (3.1 mmol) of 6 in 100 mL of glacial acetic acid. The mixture was stirred for ca. 12 h at 25° C. A precipitate was collected by filtration, washed with 5 mL of glacial acetic acid, and suspended in 200 mL of water. The aqueous suspension was adjusted to pH 9-1° with NaOH and was extracted with Et$_2$O. The combined ethereal extracts were washed with water, dried over anhydrous MgSO$_4$ and concentrated. The residue was recrystallized from ethanol to afford 590 mg (69%) of 7 as yellow crystals: mp 97-98° C. $^1$H NMR (DMSO-d$_6$): δ 7.41 (d, 1H, J=16.4 Hz), 7.27 (d, 1H, J=8.8 Hz), 7.24-7.18 (m, 1H), 7.12-7.05 (m, 2H), 6.61 (d, 1H, J=16.4 Hz), 6.10 (dd, 1H, J$_1$=8.8 Hz, J$_2$=2.4 Hz), 6.03 (d, 1H, J=2.8 Hz), 5.05 (br.s, 2H), 2.87 (s, 6H). $^{13}$C NMR (DMSO-d$_6$): δ 160.25 (dd, J$_1$=246.0 Hz, J$_2$=7.9 Hz, two C), 151.95, 147.98, 132.39 (t, J=7.1 Hz), 127.45 (t, J=11.1 Hz), 127.06, 116.11 (t, J=15.1 Hz), 112.20 (dd, J$_1$=18.7 Hz, J$_2$=6.8 Hz, two C), 111.39, 108.21, 103.52, 99.07, 40.28 (two C). MS: m/z (%) 275 (21), 274 (100), 273 (33), 257 (15), 211 (16). Anal. Calcd for C$_{16}$H$_{16}$F$_2$N$_2$: C, 70.06; H, 5.88. Found: C, 70.18; H, 5.94.

Synthesis of (E)-1,3-Difluoro-2-(4-nitrostyryl)benzene (8)

To a solution of 956 mg (2 mmol) of (4-nitrobenzyl)triphenylphosphonium bromide and 284 mg (2 mmol) of 2,6-difluorobenzaldehyde in 20 mL of CH$_2$Cl$_2$ was added 5 mL of 0.48 M NaOH solution (2.4 mmol, 1.2 equiv) dropwise over a 10 min period. The red solution was heated at 50° C. for 1 h. The organic layer was separated, washed with a saturated aqueous NaHSO$_3$ solution and water, and dried over anhydrous MgSO$_4$. The residue was recrystallized from ethanol to afford 360 mg (69%) of 8 as light yellow crystals: mp 136-137° C. $^1$H NMR (DMSO-d$_6$): δ 8.23 (d, 2H, J=8.8 Hz), 7.93 (d, 2H, J=8.8 Hz), 7.50 (d, 1H, J=16.8 Hz), 7.46-7.40 (m, 1H), 7.37 (d, 1H, J=16.8 Hz), 7.23-7.17 (m, 2H). $^{13}$C NMR (DMSO-d$_6$): δ 160.79 (dd, J$_1$=249.4 Hz, J$_2$=7.3 Hz, two C), 147.27, 143.81, 133.35 (t, J=7.9 Hz), 130.82 (t, J=10.7 Hz), 128.21 (two C), 124.46 (two C), 119.70 (t, J=1.6 Hz), 113.79 (t, J=15.1 Hz), 112.65 (dd, J$_1$=19.5 Hz, J$_2$=5.9 Hz, two C). MS: m/z (%) 261 (61), 231 (67), 214 (45), 194 (34), 183 (100). Anal. Calcd for C$_{14}$H$_9$F$_2$NO: C, 64.37; H, 3.47. Found: C, 64.56; H, 3.42.

Synthesis of (E)-4-(2,6-Difluorostyryl)aniline (9)

The procedure described for the preparation of 7 was repeated using 300 mg (1.15 mmol) of 8 in 20 mL of glacial HOAc and 1.85 g (9.76 mmol, 8.5 equiv) of SnCl$_2$ in 3 mL of conc HCl to afford, after stirring ca. 12 h at 25° C. and quenching with water, a precipitate. The precipitate was collected by filtration, washed with 5 mL of glacial acetic acid and suspended in 80 mL of water. The aqueous suspension was adjusted to pH 9-10 with NaOH and was extracted with Et$_2$O. The combined ethereal extracts were washed with water, dried over anhydrous MgSO$_4$, and concentrated. The product was recrystallized from hexane to afford 220 mg (83%) of 9 as colorless crystals: mp 74-75° C. $^1$H NMR (DMSO-d$_6$): δ 7.28 (d, 2H, J=8.8 Hz), 7.27-7.22 (m, 1H), 7.21 (d, 1H, J=16.8 Hz), 7.13-7.06 (m, 2H), 6.77 (d, 1H, J=16.8 Hz), 6.57 (d, 2H, J=8.8 Hz), 5.43 (s, 2H). $^{13}$C NMR (DMSO-d$_6$): δ 160.35 (dd, J$_1$=246.8 Hz, J$_2$=8.0 Hz, two C), 150.06, 136.41 (t, J=7.9 Hz), 128.42 (two C), 127.99 (t, J=10.3 Hz), 124.68, 115.31 (t, J=15.1 Hz), 114.29 (two C), 112.33 (dd, J$_1$=19.1 Hz, J$_2$=6.3 Hz, two C), 108.84. MS: m/z (%) 232 (18), 231 (100), 183 (13). Anal. Calcd for C$_{14}$H$_{11}$F$_2$N: C, 72.72; H, 4.79. Found: C, 72.77; H, 4.83.

Synthesis of (E)-N-(2-(2,6-Difluorostyryl)-5-(dimethylamino)phenyl)-5-(2-oxohexahydro-1H-thieno[3,4-d]imidazol-4-yl)pentanamide (10)

To 200 mg (0.82 mmol) of biotin was added 8 mL (0.11 mol) of SOCl$_2$. The mixture was stirred for 1 h at 25° C. The mixture was concentrated and co-evaporated with benzene (two 15 mL portions) to give the acid chloride. To a solution of 186 mg (0.68 mmol) of 7 and 83 mg (0.82 mmol, 1.2 equiv) of Et$_3$N in 5 mL of anhydrous THF was added the acid chloride in 8 mL of anhydrous THF dropwise. The mixture was stirred for 2 h at 25° C., poured into water and extracted with CH$_2$Cl$_2$. The combined organic phases were dried over anhydrous MgSO$_4$ and evaporated to give a product that was purified by chromatography using 1:10 CH$_3$OH—CH$_2$Cl$_2$ to afford 200 mg (59%) of 10 as a yellow solid: mp 183-184° C. $^1$H NMR (DMSO-d$_6$): δ 9.51 (s, 1H), 7.61 (d, 1H, J=8.8 Hz), 7.40 (d, 1H, J=16.4 Hz), 7.32-7.24 (m, 1H), 7.15-7.09 (m, 2H), 6.80 (d, 1H, J=16.8 Hz), 6.67-6.61 (m, 2H), 6.45 (s, 1H), 6.36 (s, 1H), 4.31-4.28 (m, 1H), 4.15-4.11 (m, 1H), 3.12-3.07 (m, 1H), 2.93 (s, 6H), 2.80 (dd, 1H, J$_1$=12.4 Hz, J$_2$=5.2 Hz), 2.57 (d, 1H, J=12.4 Hz), 2.31 (t, 2H, J=7.2 Hz), 1.69-1.35 (m, 6H). $^{13}$C NMR (DMSO-d$_6$): δ 171.90, 163.14, 160.40 (dd, J$_1$=247.6 Hz, J$_2$=7.9 Hz, two C), 151.03, 137.35, 132.05 (t, J=8.0 Hz), 128.27 (t, J=11.0 Hz), 126.36, 120.44, 115.40 (t, J=15.0 Hz), 112.36 (dd, J$_1$=19.1 Hz, J$_2$=6.4 Hz, two C), 110.93, 110.65, 110.20, 61.47, 59.64, 55.86, 40.40 (two C), 40.31, 36.11, 28.70, 28.55, 25.84. HRMS (EI) Calcd for C$_{26}$H$_{30}$F$_2$N$_4$O$_2$S: 500.2057. Found: 500.2047.

Synthesis of (E)-N-(4-(2,6-Difluorostyryl)phenyl)-5-(2-oxohexahydro-1H-thieno[3,4-d]imidazol-4-yl)pentanamide (11)

To a suspension of 100 mg (0.41 mmol 1 equiv) of biotin in 3 mL of anhydrous DMF was added 66 mg (0.49 mmol, 1.2 equiv) of 1-hydroxybenzotriazole hydrate, 94 mg (0.49 mmol, 1.2 equiv) of N-(3-dimethylaminopropyl)-N'-ethyl-carbodiimide hydrochloride, and 79 mg (0.78 mmol, 1.9 equiv) of Et$_3$N. The mixture was stirred for 10 min, and 95 mg (0.41 mmol) of 9 was added. The mixture was stirred for 24 h at 25° C. and poured into water. The precipitate was collected by filtration and chromatographed using 1:1 EtOAc-MeOH to give 120 mg (66%) of 11 as white crystals: mp 278-280° C. $^1$H NMR (DMSO-d$_6$): δ 9.99 (s, 1H), 7.64 (d, 2H, J=8.8 Hz), 7.56 (d, 2H, J=8.8 Hz), 7.37-7.29 (m, 2H), 7.19-7.12 (m, 2H), 7.02 (d, 1H, J=16.4 Hz), 6.44 (s, 1H), 6.36 (s, 1H), 4.33-4.29 (m, 1H), 4.16-4.13 (m, 1H), 3.15-3.10 (m, 1H), 2.83 (dd, 1H, J$_1$=12.8 Hz, J$_2$=4.8 Hz), 2.58 (d, 1H, J=12.0 Hz), 2.33 (t, 2H, J=7.2 Hz), 1.70-1.33 (m, 6H). $^{13}$C NMR (DMSO-d$_6$): δ 171.70, 163.13, 160.53 (dd, J$_1$=247.8 Hz, J$_2$=7.7 Hz, two C), 140.09, 135.28 (t, J=7.9 Hz), 131.77, 129.18 (t, J=10.7 Hz), 127.69 (two C), 119.54 (two C), 114.61 (t, J=15.5 Hz), 113.25, 112.45 (dd, J$_1$=19.1 Hz, J$_2$=6.3 Hz, two C), 61.48, 59.63, 55.82, 40.28, 36.70, 28.67, 28.53, 25.50. HRMS (EI) Calcd for C$_{24}$H$_{25}$F$_2$N$_3$O$_2$S: 457.1636. Found: 457.1650. Anal. Calcd for C$_{24}$H$_{25}$F$_2$N$_3$O$_2$S: C, 63.00; H, 5.51. Found: C, 62.82; H, 5.47.

Synthesis of (E)-N-(4-(2,6-Difluorostyryl)phenyl)-N-methyl-5-(2-oxohexahydro-1H-thieno[3,4-d]imidazol-4-yl)pentanamide (12)

The procedure used to prepare 10 was repeated using 167 mg (0.68 mmol) of 4 cc and 200 mg (0.82 mmol, 1.2 equiv) of biotin to afford a product that was purified by chromatography using 1:10 CH$_3$OH—CH$_2$Cl$_2$ to afford 130 mg (41%) of 12 as a colorless solid: mp 91-93° C. $^1$H NMR (DMSO-d$_6$): δ 7.71 (d, 2H, J=8.0 Hz), 7.41-7.36 (m, 2H), 7.33 (d, 2H, J=8.4 Hz), 7.21-7.14 (m, 3H), 6.38 (s, 1H), 6.33 (s, 1H), 4.30-4.26 (m, 1H), 4.09-4.06 (m, 1H), 3.17 (s, 3H), 3.05-3.00 (m, 1H), 2.80 (dd, 1H, J$_1$=12.2 Hz, J$_2$=5.2 Hz), 2.56 (d, 1H, J=12.4 Hz), 2.09 (br.s, 2H), 1.58-1.18 (m, 6H). $^{13}$C NMR (DMSO-d$_6$): δ 171.96, 163.13, 160.61 (dd, J$_1$=248.0 Hz, J$_2$=7.6 Hz, two C), 144.40, 134.71 (t, J=7.9 Hz), 129.80 (t, J=11.1 Hz), 128.27 (two C), 128.07, 128.01, 115.70 (two C), 114.35 (t, J=15.1 Hz), 112.54 (dd, J$_1$=19.1 Hz, J$_2$=6.4 Hz, two C), 61.42, 59.62, 55.75, 40.27, 37.20, 33.64, 28.54, 28.43, 25.32. MALDI-TOFMS Calcd for C$_{25}$H$_{28}$F$_2$N$_3$O$_2$S [MH+]: 472.1870. Found 472.1872.

Synthesis of N-(2-(4-(2,6-Difluorostyryl)phenyl)-4-oxo-8,11-dioxa-2,5-diazamidecan-13-yl)-5-(2-oxo-hexahydro-1H-thieno[3,4-d]imidazol-4-yl)pentanamide (13)

To a solution of 34 mg (0.14 mmol, 1.5 equiv) of 4 cc in 1 mL of absolute ethanol was added 50 mg (0.092 mmol) of (+)-biotinyl-iodoacetamidyl-3,6-dioxaoctanediamine and 20 mg (0.14 mmol, 1.5 equiv) of anhydrous K$_2$CO$_3$. The mixture was refluxed for 12 h, filtered, and concentrated. The product was chromatographed using 1:10 CH$_3$OH—CH$_2$Cl$_2$ to afford 16 mg (26%) of 13 as a clear glass that resisted crystallization. The initial product isolated was the pure (E)-isomer but during concentration, even at low temperature, rapidly equilibrated to a mixture of (E/Z)-isomers. The ratio of isomers varied with solvent ranging from ca. 10:90 in acetone-d$_6$ to 60:40 in DMSO-d$_6$. This isomerization necessarily complicated the NMR spectra, and the data reported below is for the principal (E)-isomer: $^1$H NMR (acetone-d$_6$): 7.48 (d, 2H, J=8.8 Hz), 7.42-7.35 (m, 2H), 7.30-7.22 (m, 1H), 7.13 (br.s, 1H), 7.05-7.00 (m, 2H), 6.95 (d, 1H, J=16.8 Hz), 6.75 (d, 2H, J=9.2 Hz), 5.87 (s, 1H), 5.64 (s, 1H), 4.51-4.46 (m, 1H), 4.34-4.29 (m, 1H), 3.97 (s, 2H), 3.59-3.45 (m, 8H), 4.42-3.29 (m, 4H), 3.23-3.17 (m, 1H), 3.13 (s, 3H), 2.92 (dd, 1H, J$_1$=12.4 Hz, J$_2$=4.8 Hz), 2.69 (d, 1H, J=12.4 Hz), 2.18 (t, 2H, J=7.2 Hz) 1.81-1.39 (m, 6H). It was noted that the MALDI-TOFMS Calcd for C$_{33}$H$_{44}$F$_2$N$_5$O$_5$S [MH+]: 660.3030. Found 660.3040.

Example 4

Natural Stilbene Analogues Resveratrol and Pterostilbene Inhibit Wnt Signaling

Materials and Methods:
The following materials and methods have been used to generate the results in this and other examples in the application.

Cell Culture and Transfection.
HEK293T, HCT116 and SW480 cells were grown in DMEM medium (Mediatech) supplemented with 10% fetal bovine serum and 1% penicillin/streptomycin. LS 174T cells were grown in RPMI medium (Mediatech) supplemented with 5% fetal bovine serum and 1% penicillin/streptomycin. HEK293T cells were transiently transfected using the calcium phosphate method as described in Zhang, W. et al., Mol Cell Biol 2006, 26, 2055-2064 (incorporated herein by reference).

Western Blot.
Western blots were performed using the following antibodies: β-catenin (Sigma, C2206), c-Myc (Epitomics, 1472-1), Axin2 (Cell Signaling, 2151), β-Actin (Sigma, A1978), TCF4 (Epitomics, 2114-1) and pygopus2 (Santa Cruz, sc-74878), Cyclin D1 (Cell signaling, 2926).

RT-PCR.
LS174 cells were treated with DMSO or Wnt inhibitors. After 36 h, RNA was isolated using the RNeasy kit (Qiagen). RT-PCR was performed as described in Zhang et tal., Mol Cell Biol 2006, 26, 2055-2064. The following primers were used: β-actin: 5'-CAACCGCGAGAAGATGAC-3' (SEQ ID NO:01), 5'-AGGAAGGCTGGAAGAGTG-3' (SEQ ID NO:02); surivivin: 5'-CATTCGTCCGGTTGCGCTTTCC-3' (SEQ ID NO:03), 5'-GCGCACTTTCTCCGCAGTTTCC-3' (SEQ ID NO:04); c-Myc: 5'-TGGGCTGTGAGGAG-GTTTG-3' (SEQ ID NO:05), 5'-TATGTGGAGCGGCT-TCTCG-3' (SEQ ID NO:06); Axin2: 5'-CACCACCACCAC-CACCATTC-3' (SEQ ID NO:07), 5'-GCATCCACTGCCAGACATCC-3' (SEQ ID NO:08); TCF4: 5'-CACCACATCATACGCTACAC-3' (SEQ ID NO:09), 5'-CGACCTTTGCTCTCATTTCC-3' (SEQ ID NO:10); pygopus2: 5'-GGCCGGTCTGCAAATGAAG-3' (SEQ ID NO:11), 5'-TCCACCTCCAGTGCTGTAG-3' (SEQ ID NO:12); Lgr5: 5'-CCTGCTTGACTTTGAGGAAGAC-3' (SEQ ID NO:13), 5'-ATGTTCACTGCTGCGATGAC-3' (SEQ ID NO:14); CD44: 5'-CAGAATGGCTGAT-CATCTTG-3' (SEQ ID NO:15), 5'-CAAATGCACCATTTC-CTGAG-3' (SEQ ID NO:16); Ki67: 5'-ACAGAGTGCT-CAACAACTTC-3' (SEQ ID NO:17), 5'-GCTTGCAGAGCATTTATCAG-3' (SEQ ID NO:18).

Luciferase and Cell Proliferation Assay.
HEK293T cells were transiently transfected in a 12-well plate with 0.2 µg of the Super8xTOPFlash reporter and 0.05 µg of Renilla luciferase reporter. Culture medium was changed after 12 h. After 6 h, cells were treated with DMSO or Wnt inhibitors for 12 h, and then treated with 25 mM LiCl or Wnt conditioned medium. After 12 h, cells were harvested and luciferase activity measured by Dual-luciferase Reporter Assay System (Promega, Madison Wis.). All conditions were done in triplicate and each experiment was carried out at least two times. For cell proliferation assay, CRC cells were treated with DMSO or inhibitors for 2 d and 4 d. The cell numbers and viability were analyzed by Vi-Cell Cell Viability Analyzer.

Tumor Xenograft in Nude Mice.

LS174 or HT29 colon cancer cells ($2\times10^6$) were injected subcutaneously into both flanks of 6-8 week C57BL/6J athymic nude mice as described in Zhang et al., Mol Cell Biol 2006, 26, 2055-2064. Compound 4r or 4dd was dissolved in corn oil or PEG400. The mice were treated with 20 mg/kg/day of 4r by ip injection or gavage (50 μl/mouse). Control mice were treated with same volume of corn oil or PEG400. The body weight and tumor growth were analyzed twice weekly for one month. Tumor size was measured using digital caliper. The tumor volume was calculated by the formula: $V=1/2LW^2$ ($mm^3$).

Immunofluorescence.

Cells grown on cover glass were fixed by 4% paraformaldehyde for 20 min at room temperature. The cells were permeabilized with PBS containing 0.3% (w/v) Triton X-100 and blocked by 5% normal goat serum in PBS for 30 min Anti-β-catenin antibody (1:300, Sigma, St. Louis, Mo.) was diluted in blocking solution and incubated with cells overnight. The cells were washed 3 times with PBS and further incubated with Alexa-488-labeled anti-rabbit IgG (1:500) diluted in PBS for 40 min. The cover glasses were washed, mounted on glass slides, viewed and photographed with an Olympus FW1000 confocal microscope. Cells grown on cover glass were treated with fluorescent compounds for 2 h, 6 h, 12 h and 24 h respectively. Treated cells were fixed by 4% paraformaldehyde for 20 min at room temperature. Then cells were washed 3 times with PBS and mounted on glass slides, viewed under the fluorescence of 405 nm-wavelength and photographed with an Olympus FW1000 confocal microscope.

To identify Wnt pathway inhibitors for CRC prevention and treatment, a number of anti-cancer agents from plants were screened using the TopFlash reporter assay. The TopFlash reporter was transfected into HEK293T cells, and the cells were treated with Wnt3A-conditioned medium in order to activate the luciferase reporter. Resveratrol (100 μM) significantly inhibited Wnt-induced luciferase activity. To determine if resveratrol regulates β-catenin degradation, the cells were treated with 25 mM LiCl, which inhibits GSK-3 and stabilizes β-catenin. In this assay, LiCl activated the reporter more strongly than Wnt3A conditioned medium. Resveratrol strongly inhibited LiCl-induced Wnt signaling, suggesting that resveratrol inhibits Wnt signaling by regulating β-catenin activity, but not its degradation. Emodin is an anti-cancer agent from plants; it exists in many unpurified resveratrol products. Emodin had no effect on Wnt signaling. See Zhang et al., J. of Med. Chem. 54, 1288-1297 (2011).

To confirm these results, β-catenin target genes were analyzed in LS174 CRC cells by Western blot and RT-PCR. The protein levels of c-Myc and Cyclin D1, which are β-catenin targets, are reduced by resveratrol but not its isomer, cis- or (Z)-resveratrol. Cyclin B1 levels were decreased, whereas $p21^{WAF1/CIP1}$ levels increased, consistent with the fact that $p21^{WAF1/CIP1}$ expression is repressed by c-Myc. β-catenin levels were not affected by resveratrol. Next, the mRNA levels of β-catenin target genes were analyzed using RT-PCR. Expression of survivin, Lgr5, CD44, and c-Myc were decreased in resveratrol-treated cells. The cell proliferation marker, Ki67, also decreased. These results confirmed that resveratrol inhibits endogenous Wnt target genes in CRC cells.

Many stilbene derivatives also exhibit anti-cancer activity. To determine the structure/activity relationship of these compounds, several resveratrol analogs were tested. It was found that pterostilbene inhibits Wnt signaling. To determine the effects of resveratrol and pterostilbene on cell growth, LS 174 CRC cells were treated with resveratrol and pterostilbene for 2 d and 4 d. Both compounds inhibited cell proliferation. Similar results were observed with other CRC lines Pterostilbene was more active than resveratrol in these assays, suggesting that an assay involving Western blots to measure Wnt target protein level was effective to identify other resveratrol analogs for Wnt inhibition and CRC repression.

Example 5

Halogenated Stilbene Analogs are Potent Wnt Inhibitors

A panel of stilbene analogs was designed and synthesized (FIGS. 2, 3, 5A and 6A). Various monosubstituted hydroxyl, alkoxy, amino and N,N-dialkylaminostilbenes were analyzed using the Western blot assay (FIG. 5B, 5C), and of these substituents, (E)-4-styryl-N,N-dimethylaniline (4d) at 30 μM with an N,N-dimethylamino substituent strongly repressed Wnt target genes, Axin2 and c-Myc, in CRC cells (FIG. 5C). However, the solubility of 4d was poor and it was not effective below 10 μM concentrations (data not shown). To improve its solubility and activity, compound 4d was modified with 2'-fluoro 4e, 3'-fluoro 4f and 4'-fluoro 4g substituents (FIG. 5D). Both compounds 4e and 4f had good activity at 10 μM, (E)-4-(2-fluorostyryl)-N,N-dimethylaniline. Compound (4e) was best among all of the monofluoro-substituted compounds. Modifications of the N,N-dimethylamino group within compound 4e were also analyzed, and it was found that the N,N-diethylamino group in (E)-4-(2-fluorostyryl)-N,N-diethylaniline (4h) is also active at 10 μM, but not as potent as compound 4e and the N,N-diphenylamino group in compound 4i was inactive (FIG. 5E). These analogs had no effect on β-catenin levels, further indicating that they affect β-catenin activity, but not its stability. The effects of compound 4e, resveratrol, and pterostilbene on CRC cell growth were compared and it was found that 4e is a significantly better inhibitor in the cell proliferation assay (FIG. 5F).

Figure 6:
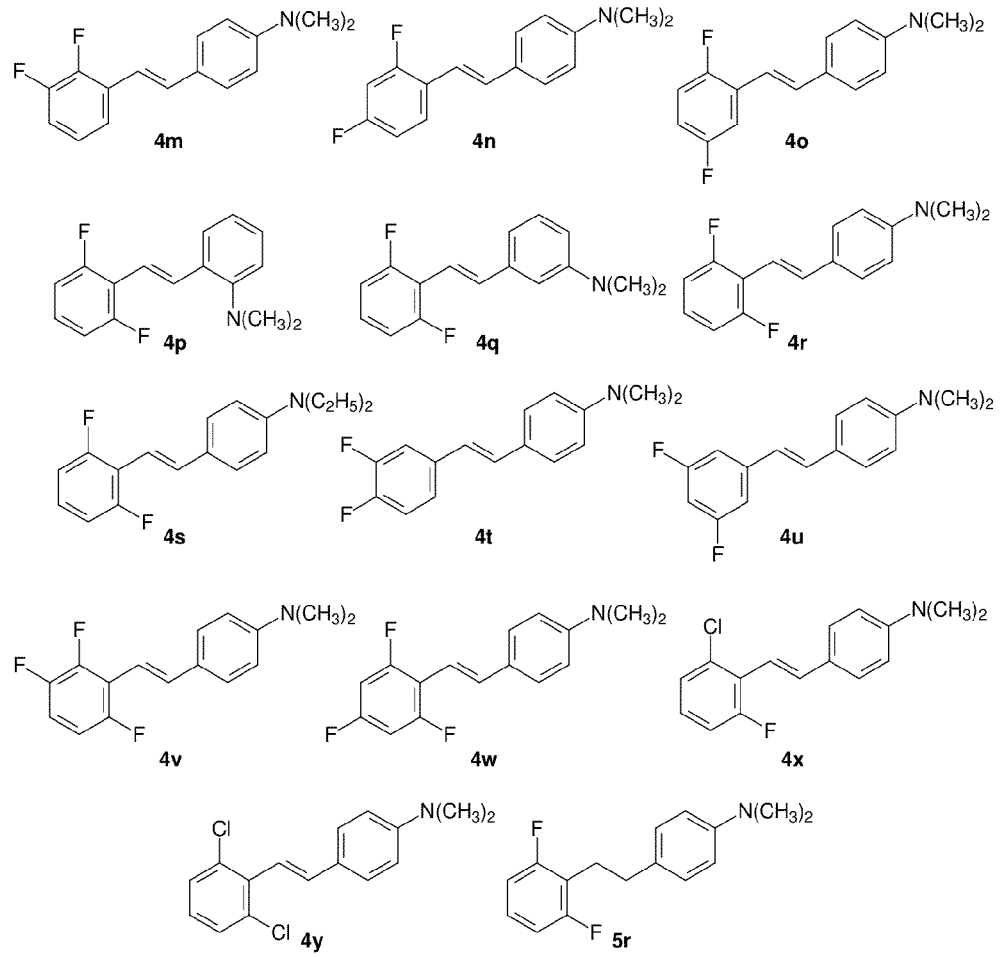
FIG. 6(A) provides the chemical structures of several dihalogenated N,N-dialkylaminostilbene analogs 4 and a saturated analog 5r of the disclosure.
FIG. 6(B) is a Western blot showing that dihalogenated N,N-dimethylaminostilbenes 4o, 4m and 4r, repress Wnt target genes at 10 µM.
FIG. 6(C) is a Western blot showing that the ortho- and meta-isomers of N,N-dimethylamino analogs (4p and 4q) are not as active as the para-isomer (4r).
FIG. 6(D) is a Western blot showing that trihalogenated N,N-dimethylaminostilbene analogs (4v and 4w) are active Wnt inhibitors.
FIG. 6(E) is a Western blot demonstrating that compound 4r represses Wnt target genes at 0.5 µM.
Figure 6:
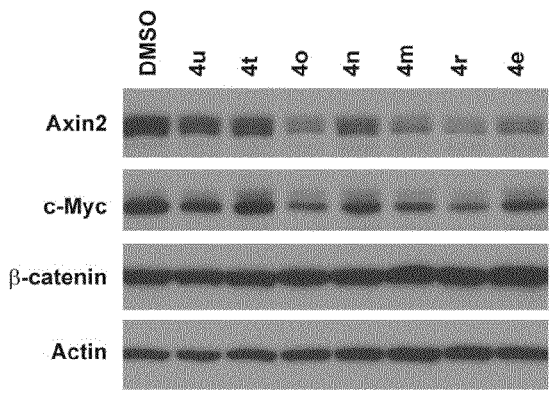
Figure 6:
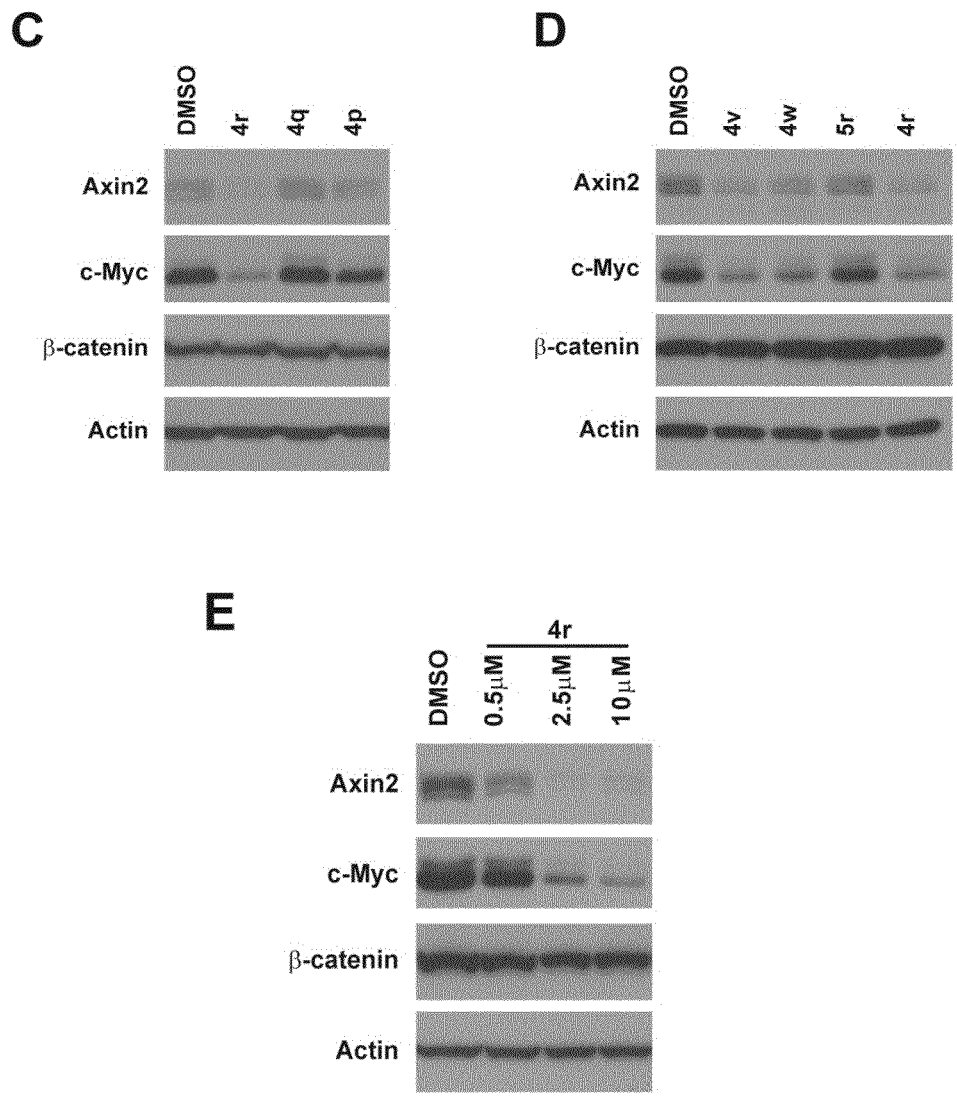

Based on the improved activity seen in compound 4e relative to compound 4d, dihalogenated N,N-dimethylaminostilbenes in which at least one of the fluorine substituents is in the 2'- or 3'-position were synthesized (FIG. 6A). The compounds with a 2'-fluoro and another fluoro ortho or meta to the double bond (compounds 4m, 4o and 4r) are more active than compound 4e (FIG. 6B). The (E)-4-(2,6-difluorostyryl)-N,N-dimethylaniline (compound 4r) had the best activity. The ortho- and meta-N,N-dimethylamino analogs of compound 4r (i.e., compounds 4p and 4q) are not as active as compound 4r, indicating that the para-dimethylamino in compound 4r is important for its activity (FIG. 6C). Based on the structure of compound 4r, two trihalogenated dimethylaminostilbenes were synthesized (compounds 4v and 4w) in which two of the fluorine substituents are in the 2'- and 6'-positions (FIG. 6D). Although compounds 4v and 4w were active at 10 μM, they showed no significant improvements over compound 4r. When the stilbene carbon-carbon double bond in compound 4r was reduced to a saturated, single bond in the 1,2-diarylethane compound 5r, the activity was lost, suggesting that the double bond is essential for biological activity (FIG. 6D). LS174 CRC cells were treated with different dosages of compound 4r and it was found that compound 4r significantly inhibited Wnt target genes at 2.5 μM and was even active at 0.5 µM (FIG. 6E). For example, based on the Western blot and cell proliferation assays, it was determined that stilbene 4r was 10- to 100-fold more potent than resveratrol and pterostilbene.

Example 6

Halogenated Stilbene Analogs Inhibit CRC In Vitro and In Vivo

Figure 7:
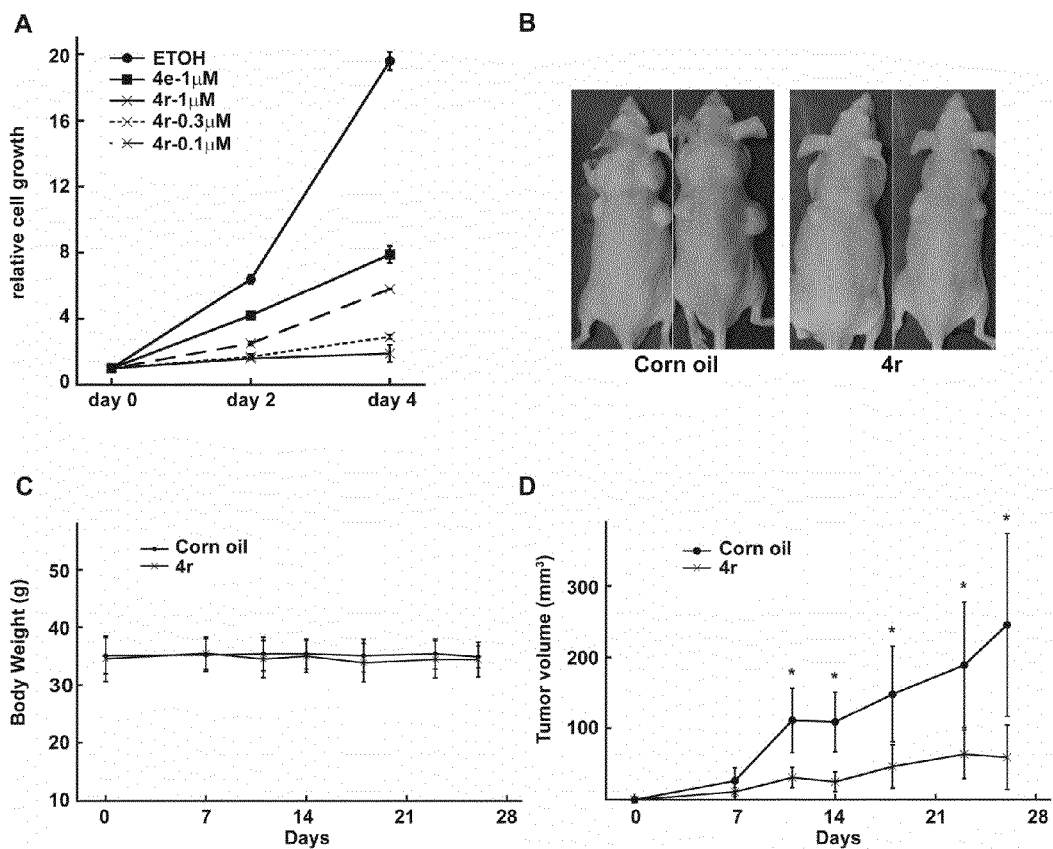
FIG. 7 demonstrates the effects of halogenated analogs of the present disclosure on CRC cell proliferation in vitro and in vivo.

In this example, the effects of the stilbene analogs of the present disclosure on CRC cells growth was analyzed. Consistent with the Western blot results, stilbene compound 4r was more potent than compound 4e in the cell proliferation assay; it inhibited LS 174 cell proliferation at nanomolar concentrations (FIG. 7A). To test the effects of compound 4r on tumor growth in vivo, LS174 cells were injected subcutaneously into the flanks of athymic nude mice, which had been randomized into two groups. One group of mice was treated with compound 4r (20 mg/kg/day) dissolved in corn oil by intraperitoneal (ip) injection. The control mice were treated with the same volume of corn oil (50 µL) by ip injection. The mice were weighted and tumors measured twice weekly. The compound 4r treated mice and control mice had no significant difference in body weight within one month (FIGS. 7B and 7C), suggesting that compound 4r has no significant toxic effect at this dosage. However, the growth of tumor xenografts were significantly inhibited by 4r treatment (FIG. 7D).

Therefore, as shown in this example, the halogenated stilbene analogs of the present disclosure are capable of inhibiting CRC both in vitro and in vivo. In another study, it was shown that mice could tolerate at least 200 mg/kg of a halogenated stilbene analog, FlDAS 4dd. The body weights in these mice were reduced after one week but were recovered to normal weight after stopping 4dd treatment (data not shown).

Example 7

Halogenated Stilbene Analogs Inhibit Wnt Signaling in the Nucleus

Figure 8:
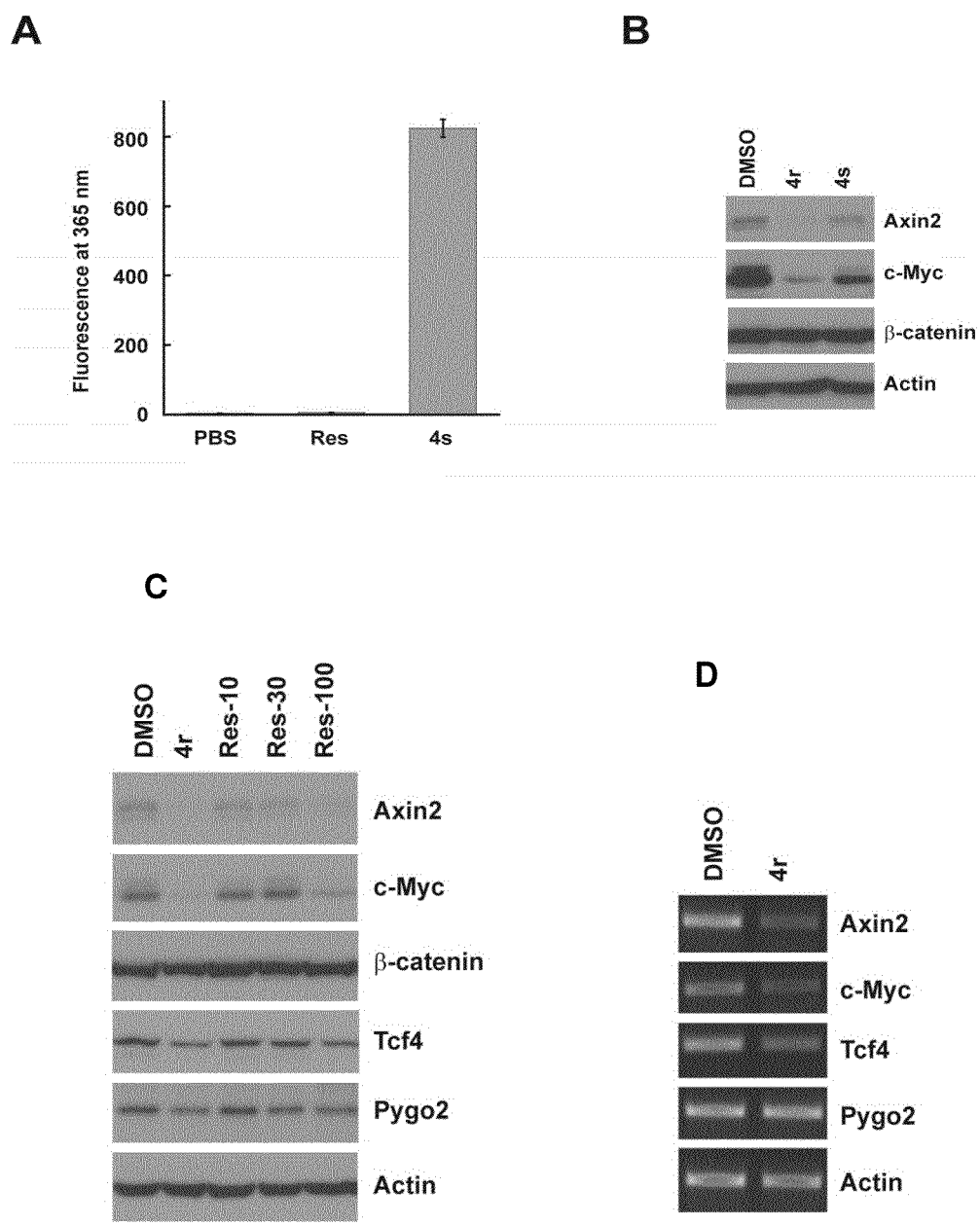
FIG. 8(A) is a bar graph showing fluorescence at 365 nM detected by Promega GloMax® Luminometer.
FIG. 8(B) is a Western blot showing compound 4s is an active Wnt inhibitor. 8(C) is a Western blot showing that compound 4r (10 µM) and resveratrol (100 µM) reduced the protein levels of Wnt/β-catenin targets in LS174 cells.
FIG. 8(D) is a Western blot showing that compound 4r represses transcription of Wnt target genes.

The stilbene analogs of the present disclosure and in particular, (E)-4-(2,6-difluorostyryl)-N,N-diethylaniline (compound 4s) (FIG. 8) exhibit strong fluorescence at 365 nm (FIG. 8A), albeit compound 4s is slightly less active than compound 4r (FIG. 8B). Nevertheless, compound 4s lends itself well to a mechanistic study of the site of action of these compounds. LS174 cells were treated with 10 µM of compound 4s for 2 h, 6 h, 12 h, and 24 h. The cells were fixed and analyzed by confocal fluorescence microscopy. It was found that compound 4s was localized throughout the nucleus and cytoplasm at 2 h. After 12 h, the nuclear levels of compound 4s were decreased (data not shown, see Zhang et al., J. of Med. Chem. 54, 1288-1297 (2011)). To study the effects of these compounds on β-catenin localization, LS174 cells were treated with 10 µM of compound 4r for 24 h. The cells were fixed and β-catenin localization analyzed by immunofluorescence. The nuclear β-catenin levels were decreased in compound 4r treated cells compared with the DMSO-treated cells. However, significant levels of nuclear β-catenin were still detected in the nucleus of compound 4r treated cells, suggesting that compound 4r may also inhibit Wnt signaling though mechanisms other than regulating β-catenin level and localization. The downstream factors of β-catenin were analyzed and it was found that the protein levels of TCF4 and pygopus2 were reduced by compound 4r and resveratrol in CRC cells (FIG. 8C). RT-PCR assay suggested that compound 4r strongly inhibited the transcription of Wnt target genes. It also inhibited TCF4 genes, but had no significant effects on pygopus2 genes, which suggests that these halogenated stilbene analogs inhibit Wnt/mediated transcription at multiple levels (FIG. 8D).

Example 8

Target Identification for Halogenated Stilbene Analogs

Materials and Methods:
The following materials and methods have been used to generate the results in this and other examples in the application.

Western Blot and Cell Proliferation Assay.
The activity of fluorinated N,N-dialkylaminostilbenes (FlDAS or FlDAS agents) on Wnt signaling activity in cancer cells were analyzed by Western blot with antibodies against Wnt target genes, such as c-Myc, Axin2 The effects of FlDAS agents on cancer cell growth were analyzed using Cell Viability Analyzer (Beckman Coulter, Vi-Cell XR). These assays have been described previously (see Zhang et al., J. of Med. Chem. 54, 1288-1297 (2011)).

Lentivirus-Mediated shRNA Assay.
ShRNA constructs for MAT2A and MAT2B were ordered from Sigma. 293T cells were transfected with lentivirus packaging plasmids psPAX2 and pMD2.G, as well as control or MAT2A/2B shRNA plasmids. Lentivirus stock was collected 48 h after transfection. HT29, LS174T and Hep3B cell lines were infected by the lentivirus stock for 12 h, followed by sustained growth in fresh medium for 36-48 h. Infected cell lines were seeded in 12-well plate for proliferation assay. ShRNA efficiency was tested by western blot using lysate from 293T cells co-transfected with pcDNA3.1-MAT2A/2B and pLKO.1-shRNA plasmids.

Protein Purification.
To purify the FlDAS target, LS174T cell lysates were incubated with streptavidin beads and biotinylated FlDAS reagent 13 (see FIGS. 4 and 10A) at 4° C. overnight. The beads were washed 3 times with cell lysis buffer. Binding proteins were elution with 2.5 mM D-Biotin. The purified samples were separated by 4-12% gradient SDS-PAGE and analyzed by silver staining or Sypro Ruby fluorescent staining. The protein bands specifically presented in the samples of the biotinylated analog were excised and analyzed by LC-MS/MS as previously described (See Zhang et al., Novel cross talk of Kruppel-like factor 4 and beta-catenin regulates normal intestinal homeostasis and tumor repression. *Mol Cell Biol* 2006, 26, 2055-64).

MAT2A and MAT2B were Cloned into pGEX6p3 Vector.
The constructs were transfected into *E. coli* BL21. The GST-fusion proteins were induced by IPTG and purified by glutathione beads as described previously (See Liu, beta-Trcp couples beta-catenin phosphorylation-degradation and regulates *Xenopus* axis formation. *Proc Natl Acad Sci USA* 1999, 96, 6273-8). For the binding assay, purified proteins were incubated with streptavidin beads and biotinylated FlDAS 13 described above. Eluted proteins were analyzed by western blot with antibodies against GST, MAT2A or MAT2B.

SAM and SAH Analysis by LC-MS/MS.
The LC-MS/MS system consisted of two Varian ProStar 210 LC Pumps coupled with a Varian 1200L triple quadrupole mass spectrometer. The separation was performed on a Hypercarb column (50 mm×2.1 mm, 3 mm, Thermo Scientific #35003-052130). Gradient elution started with 98% solution A (0.1% formic acid in water), followed by an increase to 38% solution B (0.1% formic acid in acetonitrile) in 8 min. The column was than flushed with 90% B for 5 min and regenerated with 98% A for another 8 min. The flow rate was 0.25 mL/min Between the 3rd and 11th min, the eluent was switched to the ion source of the mass spectrometer. The precursor product transitions for SAM (m/z 399→250), SAH (m/z 385→250) and [d-4]-SAH (m/z 389→436) were monitored. The optimized ion source parameters were: Capillary Voltage: 32 V for both SAM and SAH, Collision energy: 9 V and 7V for SAM and SAH, respectively, Needle voltage: 5000 V and the Shield voltage: 600V. Nitrogen was used as the drying gas at a temperature of 300° C. and the interface heater was set to 50° C. The drying gas and nebulizing gas were set to 20 and 50 psi, respectively.

Cell Based SAM Analysis.

LS174T cells were cultured in RPMI1640 medium containing 5% FBS. Cells were treated with FIDAS reagents for 24 h or 48 hours. Cells were harvested and weighted. Perchloric acid (0.4M) was added to cell pellet (100 µl/10 mg) for deproteinization. The sample was mixed vigorously and centrifuged at 10,000 g. 60 µl supernatant was mixed with 20 µl internal standard (5 µg/ml of SAH-$d_4$). Sample was adjusted to pH 5-7 with 2.5 M $K_2HPO_4$ and kept on ice for 15 min to precipitate potassium perchlorate. Samples were centrifuged twice at 10000 g for 15 min. 5 ul of supernatants were analyzed by LC-MS/MS using a modified method based on a previous publication (see Krijt et al., *J Chromatogr B Analyt Technol Biomed Life Sci* 877, 2061-6, (2009)). SAM and SAH standard were prepared by serial dilutions with 0.4 M perchloric acid (PCA), the individual calibration points were 0.05, 0.5, 5, 50 µg/ml.

SAM Synthesis.

5 mg purified MAT2A was incubated with 1 mM L-methionine and 1 mM ATP in 500 ml reaction solution (50 mM Tris.Cl, 50 mM KCl, 10 mM MgCl2) for 5 min at 25° C. The reaction was stopped with 500 ml 0.4 M Perchloric acid and neutralized with 2.5 M K2HPO4. The samples were kept on ice for 15 min to precipitate potassium perchlorate as described above. SAM was analyzed by LC-MS/MS.

In this example, by using the biotinylated compounds of the present disclosure, it was possible to purify and identify methionine adenosyltransferase 2A (MAT2A) as the direct target for the halogenated stilbene analogs described herein.

Figure 9:
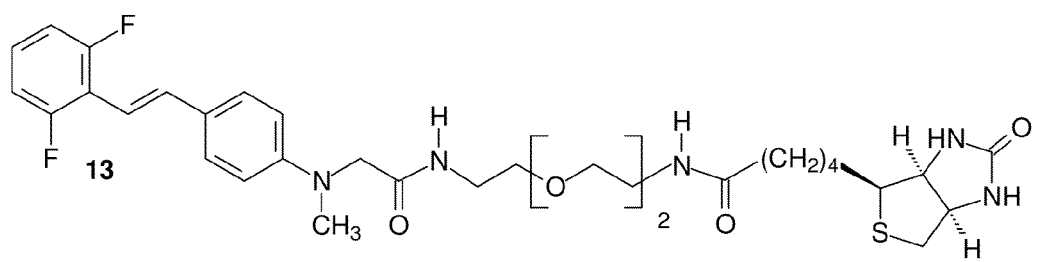
FIG. 9 relates to affinity purification of stilbene analog target.
Figure 9:
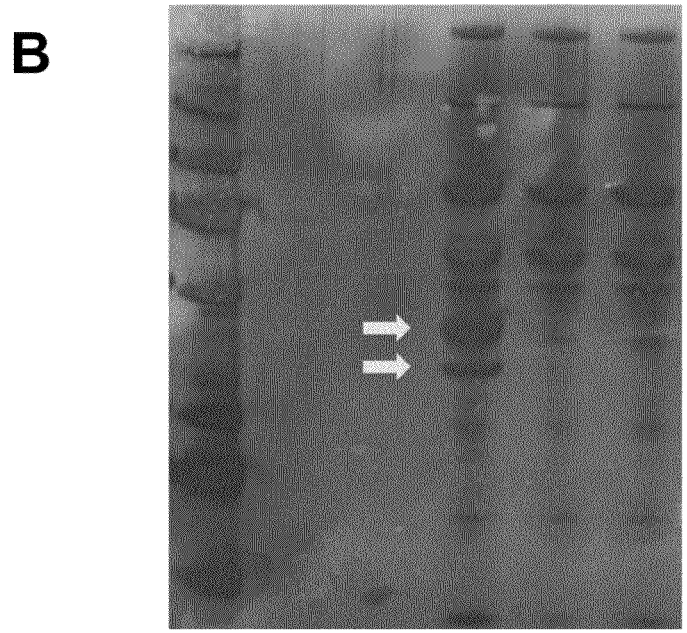

CRC cell lysates were incubated with streptavidin beads±biotin-FIDAS (FIG. 9A) and binding proteins were elution with 2.5 mM D-Biotin. The purified samples were separated by 4-12% gradient SDS-PAGE and analyzed by silver staining (FIG. 9B). Two specific protein bands were identified. These bands were analyzed by MALDI-TOF/TOF and LC-MS/MS mass spectrometry methods. These two bands were identified to be methionine adenosyltransferase 2A (MAT2A), the upper band, and methionine adenosyltransferase 2B (MAT2B), the lower band, by both methods (FIG. 9B).

Since MAT2A and MAT2B bind each other and form a complex, to determine which subunit directly interacts with FIDAS reagents, recombinant MAT2A and MAT2B were purified and tested for interaction with FIDAS. Briefly, GST-MAT2A and GST-MAT2B fusion proteins were expressed and purified from *E. coli*. These proteins were incubated with streptavidin beads with or without biotinylated derivative 13 (FIG. 9A). The binding proteins were eluted by 2.5 mM D-biotin and analyzed by Western blot with an anti-GST-Ab. It was found MAT2A directly binds to biotinylated FIDAS reagents; MAT2B binds FIDAS reagents indirectly through MAT2A (FIG. 10).

Example 9

The Effects of Halogenated Stilbene Analogs on MAT2A Enzyme Activity

Methionine adenosyltransferases catalyze the reaction of S-adenoslmethionine (SAM or AdoMet) synthesis from ATP and L-methionine. In mammals, there are three types of methionine adenosyltransferases, MATI/III and MATII. MATI and III are tetramer or dimer of al subunit (encoded by MAT1A) and are expressed in adult liver. MAT2A encodes the catalytic subunit (α2) of type II methionine adenosyltransferases. MAT2B encodes the regulating subunit of α2. MAT2A and MAT2B are widely expressed in proliferating cells and cancers. MAT2A controls the cellular levels of SAM, which is the major methyl donor for many cellular methylation reactions, including DNA methylation and protein methylation.

To test if FIDAS reagents inhibit the enzymatic activity of MAT2A, an LC-MS/MS method was developed to detect and analyze AdoMet (SAM) and SAH (S-adenosylhomocysteine) (data not shown). Furthermore, an in-vitro method was developed to synthesize SAM from L-methionine and ATP. The results show that both resveratrol and compound 4r inhibit MAT2A activity in SAM synthesis, and that 10 µM of compound 4r reduces MAT2A activity in LS174 cells more significantly than 30 µM of resveratrol. These data suggest that 4r is significantly more potent than resveratrol in MAT2A inhibition (FIG. 11A). A test of another halogenated stilbene analog in an assay for inhibition of SAM and SAH showed that compound 4dd was even more potent than 4r in inhibition of MAT2A and reduction of SAM and SAH (FIGS. 11B and 11C). In FIGS. 11B and 11C, the effects of 3 µM of 4dd was compared with the 10 uM of 4r and 30 uM of resveratrol in causing reduction in SAM and SAH concentrations, respectively. These results show that compound 4dd is even more potent than compound 4r which is significantly more potent than resveratrol.

Example 10

The Effects of MAT2A and MAT2B Genes Inhibition on Cell Proliferation

In this example, the effects of inhibition of MAT2A and MAT2B genes on cell proliferation were studied. To study the biological function of MAT2A and MAT2B in cell proliferation, the expression of MAT2A or MAT2B genes were knocked down by shRNAs (FIGS. 12A and 12B). Both MAT2A and MAT2B shRNAs inhibited proliferation of liver cancer cells Hep3B (FIG. 12C). To test if MAT2A and MAT2B are required for colon cancer cell proliferation, MAT2A and MAT2B genes were knocked down in colon cancer cells, LS174T and HT29. In a time-course study for the effects of MAT2A and MAT2B inhibition on cell proliferation in LS174T and HT29, it was determined that both MAT2A and MAT2B shRNAs inhibit proliferation of colon cancer cells, and that inhibition of MAT2A is more effective in inhibition of cancer cell proliferation than inhibition of MAT2B (FIGS. 13A and 13B).

Example 11

The Effects the Metabolites of the Halogenated Stilbene Analogs on Cell Proliferation In-Vitro As previously shown, several metabolites of the halogenated stilbenes of the present disclosure were synthesized (Example 2 and FIG. 3). In this study, the effects of some of these metabolites on cell proliferation were studied. Compounds 4aa, 4dd and 4ee were significantly more effective than resveratrol, as well as compound 4r (FIGS. 14 and 15).

Example 12

The Effects the Metabolites of the Halogenated Stilbene Analogs on Cell Proliferation In-Vivo in Mice In this study, the oral efficacy of the metabolites of halogenated stilbene analogs were tested in mice.

Xenografted nude mice were developed according to the protocol described above and in Zhang et al., J. of Med. Chem. 54, 1288-1297 (2011)). Briefly, HT29 cells were injected subcutaneously into the flanks of nude mice. The mice were then treated with 20 mg/kg compound 4dd dissolved in PEG400 by gavage. As described in Example 7, an IP injection of compound 4r dissolved in corn oil inhibited xenograft tumor growth. Here, it was also shown that the halogenated stilbenes of the present disclosure can also be dissolved in other solvents such as PEG400 and cycledextran.

The results show that 4dd significantly inhibits the growth of xenografted tumors without any adverse effect on body weight (FIG. 16).

Example 13

Halogenated Stilbene Analogs Inhibit Other Cancer Types

As discussed above, the halogenated stilbene analogs of the present disclosure bind to MAT2A and inhibit the enzyme function which leads to inhibition of colon cancer cell proliferation. Since, for example, in liver cancer, it has been shown that the expression of MAT1A is decreased while the expression of MAT2A is increased (see Cai et al., Hepatology 24, 1090-7 (1996)), Applicants hypothesized that the compound of the disclosure should inhibit proliferation of other types of cancers, particularly those in which the MAT2A activity or expression is increased.

To test this hypothesis, a number cancer cell lines were treated with the halogenated stilbene analogs of the present disclosure. The results show that the halogenated stilbene analogs are capable of inhibiting other cancer types as well. As shown in FIG. 17, the compounds of the present disclosure inhibited cell proliferation of breast cancer (FIG. 17A), lung cancer (FIGS. 17B and C), carcinoid tumor (FIG. 17D) and prostate cancer (FIG. 17E) cell lines.

Example 14

Binding Studies of MAT2A and Halogenated Stilbene Analogs

To test if the halogenated stilbene analogs of the present disclosure also bind MAT1A, a His-tagged MAT1A was cloned in and purified from E. coli. An in vitro binding assay was performed, and the results show that the compounds tested only bound to MAT2A but not MAT1A (FIG. 18B). According to published MAT structures, several key residues are involved in substrate binding and catalysis. Among these key residues, lysine 265 is conserved between MAT1A and MAT2A and among different species. When lysine 265 was mutated to leucine ($K_{265}L$, FIG. 18A), the binding between MAT2A and compound 13 was significantly decreased, suggesting that K265 is involved in binding with compounds of the present disclosure (FIG. 18C). Taken together, the FlDAS reagents are specific inhibitors of MAT2A, and are promising drug candidates for multiple cancers as well as metabolic diseases.

Example 15

The Efficacy of the Halogenated Stilbene Analogs in Inhibiting Other MAT2A-Related Diseases or Disorders It has also been shown that MAT2A is induced by hepatitis B infection in the liver Liu et al., J. Biol. Chem. 286, 17168-80 (2011)). Since the compounds of the present disclosure are effective in inhibiting MAT2A and reducing SAM, these compounds must be effective in treating any disease or condition in which MAT2A may be involved, including, but not limited to, metabolic disorders such as diabetes, heart disease, aging, obesity, and neurodegenerative disease, such as Alzheimer's and Parkinson diseases Only the preferred embodiment of the present disclosure and examples of its versatility are shown and described in the present disclosure. It is to be understood that the present disclosure is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this disclosure, and are covered by the following claims. Any or all patents and/or publications including journal articles cited in this disclosure are expressly incorporated herein by reference.

What is claimed is:

1. A method of treating liver cancer or colon cancer, the method comprising administering to a patient in need of such treatment an effective amount of a compound according to formula (I):

$$X-Ar_1-CR^a=CR^b-Ar_2 \qquad (I)$$

or a pharmaceutically acceptable salt thereof, wherein $R^a$ and $R^b$ are independently H, alkyl, halo, alkoxy, cyano; X represents at least one halogen on $Ar_1$; $Ar_1$ is phenyl and $Ar_2$ is pyridyl; provided that $Ar_2$ contains at least one $NR^cR^dZ$ substituent on $Ar_2$ where $R^c$ is H, alkyl, alkoxy, aryl, heteroaryl, $R^d$ is an unsubstituted alkyl group, Z is an unshared pair of electrons, H, alkyl, oxygen.

2. The method according to claim 1, wherein $Ar_2$ is pyridyl substituted with alkylamino, or dialkylamino.

3. The method according to claim 1, wherein X is one, two or three fluorine and/or chlorine on $Ar_1$.

4. The method according to claim 1, wherein X represents at least one fluorine and at least one chlorine on $Ar_1$.

5. The method according to claim 1, wherein, X is one or more fluorine and/or chlorine.

6. The method according to claim 1, wherein $R^c$ is H or a lower alkyl and $R^d$ is a lower unsubstituted alkyl.

7. The method according to claim 1, wherein X is one or more fluorine and/or chlorine and $R^c$ is H or a lower alkyl and $R^d$ is a lower unsubstituted alkyl.

* * * * *

SEQUENCE LISTING

<160> NUMBER OF SEQ ID NOS: 18

<210> SEQ ID NO 1
<211> LENGTH: 18
<212> TYPE: PRT
<213> ORGANISM: Artificial Sequence
<220> FEATURE:
<223> OTHER INFORMATION: B-Actin primer

<400> SEQUENCE: 1

Cys Ala Ala Cys Cys Gly Cys Gly Ala Gly Ala Ala Gly Ala Thr Gly
1               5                   10                  15

Ala Cys

<210> SEQ ID NO 2
<211> LENGTH: 18
<212> TYPE: PRT
<213> ORGANISM: Artificial Sequence
<220> FEATURE:
<223> OTHER INFORMATION: B-actin primer

<400> SEQUENCE: 2

Ala Gly Gly Ala Ala Gly Gly Cys Thr Gly Gly Ala Ala Gly Ala Gly
1               5                   10                  15

Thr Gly

<210> SEQ ID NO 3
<211> LENGTH: 22
<212> TYPE: PRT
<213> ORGANISM: Artificial Sequence
<220> FEATURE:
<223> OTHER INFORMATION: survivin primer

<400> SEQUENCE: 3

Cys Ala Thr Thr Cys Gly Thr Cys Cys Gly Gly Thr Thr Gly Cys Gly
1               5                   10                  15

Cys Thr Thr Thr Cys Cys
            20

<210> SEQ ID NO 4
<211> LENGTH: 22
<212> TYPE: PRT
<213> ORGANISM: Artificial Sequence
<220> FEATURE:
<223> OTHER INFORMATION: survivin primer

<400> SEQUENCE: 4

Gly Cys Gly Cys Ala Cys Thr Thr Thr Cys Thr Cys Cys Gly Cys Ala
1               5                   10                  15

Gly Thr Thr Thr Cys Cys
            20

<210> SEQ ID NO 5
<211> LENGTH: 19
<212> TYPE: PRT
<213> ORGANISM: Artificial Sequence
<220> FEATURE:
<223> OTHER INFORMATION: c-Myc primer

<400> SEQUENCE: 5

Thr Gly Gly Gly Cys Thr Gly Thr Gly Ala Gly Gly Ala Gly Gly Thr
1               5                   10                  15

Thr Thr Gly

<210> SEQ ID NO 6
<211> LENGTH: 19
<212> TYPE: PRT
<213> ORGANISM: Artificial Sequence
<220> FEATURE:
<223> OTHER INFORMATION: c-Myc primer

<400> SEQUENCE: 6

Thr Ala Thr Gly Thr Gly Gly Ala Gly Cys Gly Gly Cys Thr Thr Cys
1               5                   10                  15

Thr Cys Gly

<210> SEQ ID NO 7
<211> LENGTH: 20
<212> TYPE: PRT
<213> ORGANISM: Artificial Sequence
<220> FEATURE:
<223> OTHER INFORMATION: axin2 primer

<400> SEQUENCE: 7

Cys Ala Cys Cys Ala Cys Cys Ala Cys Cys Ala Cys Cys Ala Cys Cys
1               5                   10                  15

Ala Thr Thr Cys
            20

<210> SEQ ID NO 8
<211> LENGTH: 20
<212> TYPE: PRT
<213> ORGANISM: Artificial Sequence
<220> FEATURE:
<223> OTHER INFORMATION: axin2 primer

<400> SEQUENCE: 8

Gly Cys Ala Thr Cys Cys Ala Cys Thr Gly Cys Cys Ala Gly Ala Cys
1               5                   10                  15

Ala Thr Cys Cys
            20

<210> SEQ ID NO 9
<211> LENGTH: 20
<212> TYPE: PRT
<213> ORGANISM: Artificial Sequence
<220> FEATURE:
<223> OTHER INFORMATION: TCF4 primer

<400> SEQUENCE: 9

Cys Ala Cys Cys Ala Cys Ala Thr Cys Ala Thr Ala Cys Gly Cys Thr
1               5                   10                  15

Ala Cys Ala Cys
            20

<210> SEQ ID NO 10
<211> LENGTH: 20
<212> TYPE: PRT
<213> ORGANISM: Artificial Sequence
<220> FEATURE:
<223> OTHER INFORMATION: TCF4 primer

<400> SEQUENCE: 10

Cys Gly Ala Cys Cys Thr Thr Thr Gly Cys Thr Cys Thr Cys Ala Thr
1               5                   10                  15

Thr Thr Cys Cys
            20

<210> SEQ ID NO 11
<211> LENGTH: 19
<212> TYPE: PRT
<213> ORGANISM: Artificial Sequence
<220> FEATURE:
<223> OTHER INFORMATION: pygopus2 primer

<400> SEQUENCE: 11

Gly Gly Cys Cys Gly Gly Thr Cys Thr Gly Cys Ala Ala Ala Thr Gly
1               5                   10                  15

Ala Ala Gly

```
<210> SEQ ID NO 12
<211> LENGTH: 19
<212> TYPE: PRT
<213> ORGANISM: Artificial Sequence
<220> FEATURE:
<223> OTHER INFORMATION: pygopus2 primer

<400> SEQUENCE: 12

Thr Cys Cys Ala Cys Cys Thr Cys Cys Ala Gly Thr Gly Cys Thr Gly
1               5                   10                  15

Thr Ala Gly

<210> SEQ ID NO 13
<211> LENGTH: 22
<212> TYPE: PRT
<213> ORGANISM: Artificial Sequence
<220> FEATURE:
<223> OTHER INFORMATION: Lgr5 primer

<400> SEQUENCE: 13

Cys Cys Thr Gly Cys Thr Thr Gly Ala Cys Thr Thr Thr Gly Ala Gly
1               5                   10                  15

Gly Ala Ala Gly Ala Cys
            20

<210> SEQ ID NO 14
<211> LENGTH: 20
<212> TYPE: PRT
<213> ORGANISM: Artificial Sequence
<220> FEATURE:
<223> OTHER INFORMATION: Lgr5 primer

<400> SEQUENCE: 14

Ala Thr Gly Thr Thr Cys Ala Cys Thr Gly Cys Thr Gly Cys Gly Ala
1               5                   10                  15

Thr Gly Ala Cys
            20

<210> SEQ ID NO 15
<211> LENGTH: 20
<212> TYPE: PRT
<213> ORGANISM: Artificial Sequence
<220> FEATURE:
<223> OTHER INFORMATION: CD44 primer

<400> SEQUENCE: 15

Cys Ala Gly Ala Ala Thr Gly Gly Cys Thr Gly Ala Thr Cys Ala Thr
1               5                   10                  15

Cys Thr Thr Gly
            20

<210> SEQ ID NO 16
<211> LENGTH: 20
<212> TYPE: PRT
<213> ORGANISM: Artificial Sequence
<220> FEATURE:
<223> OTHER INFORMATION: CD44 primer

<400> SEQUENCE: 16

Cys Ala Ala Ala Thr Gly Cys Ala Cys Cys Ala Thr Thr Thr Cys Cys
1               5                   10                  15

Thr Gly Ala Gly
            20
```

```
<210> SEQ ID NO 17
<211> LENGTH: 20
<212> TYPE: PRT
<213> ORGANISM: Artificial Sequence
<220> FEATURE:
<223> OTHER INFORMATION: Ki67 primer

<400> SEQUENCE: 17

Ala Cys Ala Gly Ala Gly Thr Gly Cys Thr Cys Ala Ala Cys Ala Ala
1               5                   10                  15

Cys Thr Thr Cys
            20

<210> SEQ ID NO 18
<211> LENGTH: 20
<212> TYPE: PRT
<213> ORGANISM: Artificial Sequence
<220> FEATURE:
<223> OTHER INFORMATION: Ki67 primer

<400> SEQUENCE: 18

Gly Cys Thr Thr Gly Cys Ala Gly Ala Gly Cys Ala Thr Thr Thr Ala
1               5                   10                  15

Thr Cys Ala Gly
            20
```